US007235531B2

(12) United States Patent
Itoh et al.

(10) Patent No.: US 7,235,531 B2
(45) Date of Patent: Jun. 26, 2007

(54) TACHYKININ-LIKE POLYPEPTIDES AND USE THEREOF

(75) Inventors: Yasuaki Itoh, Tsuchiura (JP); Kazunori Nishi, London (GB); Chieko Kitada, Sakai (JP)

(73) Assignee: Takeda Pharmaceutical Company, Osaka (JP)

( * ) Notice: Subject to any disclaimer, the term of this patent is extended or adjusted under 35 U.S.C. 154(b) by 826 days.

(21) Appl. No.: 10/168,789

(22) PCT Filed: Dec. 21, 2000

(86) PCT No.: PCT/JP00/09083

§ 371 (c)(1),
(2), (4) Date: Jul. 10, 2002

(87) PCT Pub. No.: WO01/46415

PCT Pub. Date: Jun. 28, 2001

(65) Prior Publication Data

US 2003/0148943 A1    Aug. 7, 2003

(30) Foreign Application Priority Data

Dec. 21, 1999  (JP)  ................................. 11-362638
Mar. 10, 2000  (JP)  ............................. 2000-066714

(51) Int. Cl.
*A61K 38/04*  (2006.01)
*A61K 38/08*  (2006.01)
(52) U.S. Cl. ......................... 514/15; 530/314; 530/327
(58) Field of Classification Search ..................... None
See application file for complete search history.

(56) References Cited

U.S. PATENT DOCUMENTS

| 5,137,873 A | 8/1992 | Yankner |
| 5,350,836 A * | 9/1994 | Kopchick et al. ........... 530/399 |
| 5,876,948 A | 3/1999 | Yankner |
| 5,891,842 A | 4/1999 | Kream ........................... 514/2 |
| 6,774,219 B2 * | 8/2004 | Hostetter et al. ......... 530/388.5 |

FOREIGN PATENT DOCUMENTS

| EP | 0532456 | 8/1992 |
| JP | 05-163159 | 6/1993 |
| JP | 10-306099 | 11/1998 |
| WO | WO 86/03495 | 6/1986 |
| WO | WO 92/02248 | 2/1992 |
| WO | WO/9202248 * | 2/1992 |
| WO | WO 94/20500 | 9/1994 |
| WO | WO 98/22497 | 5/1998 |
| WO | WO 99/46367 | 9/1999 |
| WO | WO 99/53021 | 10/1999 |

OTHER PUBLICATIONS

Francklyn, C., Aminoacyl-tRNA Synthetases: Versatile Players in the Changing Theater of Translation, RNA, vol. 8, pp. 1363-1372 (2002).*

Goodman & Gilman's The Pharmacological Basis of Therapeutics, 9th Ed., McGraw-Hill, NY, (1996).*

T. Kempe, et al. "Multiple-copy Genes: Production and Modification of Monomeric Peptides From Large Multimeric Fusion Proteins" GENE 39:239-45 (1985).

A. Jeng, et al. "A Radioimmunoassay for Measuring α-Amidating Enzyme Activity" Analytical Biochemistry 185:213-19(1990).

G. Bitan, et al. "Synthesis and Biological Activity of Novel Backbone-Bicyclic Substance-P Analogs Containing Lactarn and Disulfide Bridges" Journal of Peptide Research 49:421-26(1997).

Kokyu 7[7] 764772(1988).

Y. Shimohigashi, et al. "Drug Design of Neuropeptides for Hypotensive Therapeutics"Study Report by Asahi-Glass Foundation 59:: 115-24(1991.

A. Dutta, et al. "Analogues of Substance P. Peptides Containing D-Amino Acid Residues in Various Positions of Substance P and Displaying Agonist or Receptor Selective Antagonist Effects" J. Med. Chem 29:1163-71(1986).

S. Nakanishi, et al. "Neuropeptides and Neuroendocrinological Control" Development of Medical Science 146[4]:223-230(1988).

Japanese Clinical 48[5]:98-104(1990).

C.J. Helke, et al. "Diversity in Mammalian Tachykinin Peptidergic Neurons: Multiple Peptides, Receptors, And Regulatory Mechanisms" The FASEB Journal 4:1606-15(1990).

Z. Gao, et al. "Recent Advances in Neurokinin Receptor Antagonists" Current Medicinal Chemistry 6:375-88(1999).

"Tachykinin" Kokyu (ASPRILATION), vol. 7[7], pp. 764-772(1988).

Y. Shimohigashi, et al. "Drug Design of Neuropeptides for Hypotensive Therapeutics" Study Report by Asahi-Glass Foundation, vol. 59, pp. 115-124(1992).

S. Nakanishi, et al. "Nervous Peptide and Neuroendocrine Regulation" Development of Medical Science, vol. 146[4], pp. 223-230(1988).

Japanese Clinical, vol. 48, No. 5, pp. 98-104(1990).

Waugh, D. et al., "Tachykinins with Unusual Structural Features from a Urodele, the Amphiuma, an Elasmobranch, the Hammerhead Shark, and a Agnathan, the River Lamprey", *Peptides*, (1995) vol. 16, No. 4, pp. 615-621.

Yue, K. et al., "Characterization of a Desmocollin Isoform (Bovine DSC3) Exclusively Expressed in Lower Layers of Stratified Epithelia", *Journal of Cell Science* (1995), vol. 108, pp. 2163-2173.

Legan, P.K. et al., "The Bovine Desmocollin Family: A New Gene and Expression Patterns Reflecting Epithelial Cell Proliferation and Differentiation", *The Journal of Cell Biology*, (1994), vol. 126, No. 2, pp. 507-518.

* cited by examiner

*Primary Examiner*—Eileen B. O'Hara
(74) *Attorney, Agent, or Firm*—Edwards Angell Palmer & Dodge LLP; David G. Conlin

(57) ABSTRACT

The present invention relates to amino acid sequences for novel tachykinin polypeptides and base sequences encoding them, agonists and antagonists of such polypeptides, pharmaceutical compositions comprising them, and the like.

7 Claims, 3 Drawing Sheets

Fig.1

```
TCAAGGAGCCAAAGAGCAAACCAAAGCCTGCAGGAGGCATCTTCAAGCTGAGAGGGGCTC  60

CCAGAGATTCCAGGACAGTGCAGGCTCACCATGCTGCCTTGCCTCGCCCTGCTTCTCCTG  120
                              MetLeuProCysLeuAlaLeuLeuLeuLeu

ATGGAGCTGTCCGTGTGCACTGTGGCAGGTGATGGTGGAGAGGAACAGACACTCAGCACT  180
MetGluLeuSerValCysThrValAlaGlyAspGlyGlyGluGluGlnThrLeuSerThr

GAAGCAGAGACCTGGGAAGGCGCTGGCCCCAGCATTCAGCTCCAGCTGCAGGAGGTGAAG  240
GluAlaGluThrTrpGluGlyAlaGlyProSerIleGlnLeuGlnLeuGlnGluValLys

ACGGGCAAGGCAAGCCAGTTCTTTGGGCTGATGGGGAAGCGAGTGGGAGGTGAGTGACAA  300
ThrGlyLysAlaSerGlnPhePheGlyLeuMetGlyLysArgValGlyGlyGlu

TGACAATGGAGCCCAGCAAGCAGGGGTTCTGAGTGGGTTCTGCAACATAAAGCAGAGGCC  360

CTAAGTCAAAGCC  373
```

Fig. 2

```
CAGCTGGAAGGACCAGAAAACAGGGGGAGTTTCCCCTATCTACACTCAAGGAGCCAAAGA   60

GCAAACCAAAGCCTGCAGGAGGCATCTTCAAGCTGAGAGGGGCTCCCAGAGATTCCAGGA  120

CAGTGCAGGCTCACCATGCTGCCTTGCCTCGCCCTGCTTCTCCTGATGGAGCTGTCCGTG  180
               MetLeuProCysLeuAlaLeuLeuLeuLeuMetGluLeuSerVal

TGCACTGTGGCAGGTGATGGTGGAGAGGAACAGACACTCAGCACTGAAGCAGAGACCTGG  240
CysThrValAlaGlyAspGlyGlyGluGluGlnThrLeuSerThrGluAlaGluThrTrp

GAAGGCGCTGGCCCCAGCATTCAGCTCCAGCTGCAGGAGGTGAAGACGGGCAAGGCAAGC  300
GluGlyAlaGlyProSerIleGlnLeuGlnLeuGlnGluValLysThrGlyLysAlaSer

CAGTTCTTTGGGCTGATGGGGAAGCGAGTGGGAGGCAGAGAGGATGAGGCCCAAGGTTCA  360
GlnPhePheGlyLeuMetGlyLysArgValGlyGlyArgGluAspGluAlaGlnGlySer

GAGTAAAAGCCCCCACCACAGACTTCCCAGAGGACACGGTGCCGCTTCTTCCTACCTGGA  420
Glu

TGTCACAGCTGACAAGCCGGCAGGCCAACTCTCTTCTCTGTGTCTCCTGTCCTCATCGCT  480

GGCACTTCACACAAGGCCCACACTGAACCCACTGGGCTTCTTCCTGGACTCTCAGTGTCA  540

AGCAGCAGTCCTGCATAAATGCACAGCTTCGCCGTAGCAAGCTGCACTGACTCTGCCCTC  600

CCTCACACTCAGAGTTGGCATCTCACTGCACAGCAGTGAGGAGACTCGCACACTCTGTAT  660

CCTGTGCCTAGCACACAGTAGGCACTCAATAAATGAGTGACCAGAAAAAAAAAAAAAAA   720
```

TACHYKININ-LIKE POLYPEPTIDES AND USE THEREOF

TECHNICAL FIELD

The present invention relates to novel tachykinin-like (poly)peptides (also referred to as "ATT" and "ATT polypeptides") and precursor polypeptides thereof (also referred to as "ATTα", "ATTβ," or "ATT#21F"), and to polynucleotides encoding them. The present invention also relates to recombinant vectors containing such polynucleotides, transformants containing these vectors, and non-human transgenic animals having genes containing such polynucleotides. The present invention furthermore relates to methods for producing such polypeptides, antibodies against such polypeptides, agonists and antagonists, and methods for identifying them. The present invention still furthermore relates to pharmaceutical compositions containing such polypeptides, polynucleotides, agonists, antagonists, or antibodies, as well as to methods for the treatment and/or prevention of diseases, etc.

BACKGROUND ART

In all organisms, the coordinated regulation of events such as genesis, differentiation, growth, and homeostatic maintenance is dependent on intercellular and intertissue communication. In most cases, these processes are mediated by protein factors. Many secretory factors (humoral factors) which have been discovered are involved in the immune system and hematopoietic system, for example, and are referred to as cytokines, which include lymphokines, monokines, interferons, colony-stimulating factors, tumor necrosis factors, and the like. Their relation to disease and their potential use as drugs continue to be the subject of considerable research.

Humoral factors such as growth factors or peptide hormones produced by endocrine tissue also play an extremely important role in growth and homeostatic maintenance, and their application as drugs is the subject of considerable research.

For example, "tachykinins" is the generic term for a group of physiologically active peptides included in this category, which consist of about 10 amino acids and share in common the following carboxyl terminal sequence motif:

Phe-Xaa-Gly-Leu-Met-NH$_2$ (the above sequence is an example in which the carboxyl group of the C terminal methionine is amidated, where Xaa can be any amino acid). Substance P, neurokinin A, and neurokinin B are known mammalian tachykinins, and are widely distributed in the central nervous and peripheral nervous systems. These peptides are generally released by the nerves, and in most cases are known to bind to various receptors (NK-1, NK-2, and NK-3) present in the body, thereby producing various forms of physiological activity depending on their activation. Particularly in terms of their pharmacological activity, it is clear from the literature, including Pernow et al., *Pharmacol. Rev.*, Vol. 35, pp. 85-141 (1983), that proteins with the aforementioned carboxyl terminal structure are shared. Examples of such activity are widely ranging, such as smooth muscle contraction, decreased blood pressure, enhanced exocrine function, and stimulated vasopermeability. The release of such peptides is known to induce respiratory diseases such as respiratory inflammation or bronchial contraction, and the release of histamines from mast cells. Substance P, in particular, is believed to be involved in the neurotransmission of pain, including pain associated with migraines and arthritis. These peptides may also be involved in gastrointestinal disorders and diseases such as inflammatory bowel disease, as well as other diseases. In view of the great number of clinical diseases characterized by tachykinin over-involvement, the development of tachykinin receptor antagonists may be useful in controlling such clinical pathologies, and a number of peptide and non-peptide tachykinin receptor antagonists have been developed thus far (*Nippon Rinsho*, Vol. 48, No. 5, p. 98-104 (1990), *The FASEB Journal*, Vol. 4, pp. 1606-1615 (1990), and *Current Medical Chemistry*, Vol. 6, pp. 1375-1388 (1999)).

These protein and peptide factors, which are essential to organisms, have conventionally been found on the basis of their inherent biological activity. Genes with high homology have then been discovered by means of cloning techniques based on homology for known physiologically active proteins. However, it is highly likely that, in addition to these known gene groups, humoral functional molecules, which have not been identified by conventional techniques and whose existence therefore remains unknown, also play a major physiological role in maintaining the health of higher organisms, especially mammals.

More recent research based on bioinformatics has attempted to make biological, medical, and veterinary use of novel gene products, which have been discovered on the basis of DNA sequence data, through the aid of data processing techniques using computers (*Trends in Biotechnology*), Vol. 14, pp. 294-298 (1996). With recent achievements in the large-scale screening of cDNA libraries, an enormous number of novel genes or candidates have continued to be discovered through the compilation of EST (expressed sequence tag) data. However, much of this sequence data is fragmentary and incomplete. A currently remaining, major issue is that various existing cDNA-related public databases do not always contain the complete expressed genes for various organisms. It can thus be a daunting matter to search for completely novel and useful gene products in such databases. Meanwhile, structural analysis of all the DNA of a given organism, that is, the genome, has currently been completed for several bacteria and fungi (such as yeasts). Although such research for the human genomes is expected to take several years, the number of human genes is estimated to be around a hundred thousand. The genes coding for many secretory proteins or secretory peptides have actually been isolated already. However, that number cannot be understood to include all the genes of the genome. Despite the intense desire to find novel useful products, the aforementioned data processing techniques alone cannot be considered adequate for the elucidation of such genes; proof must be based on more detailed biological or chemical analysis and experimentation.

DISCLOSURE OF THE INVENTION

An object of the present invention is thus to provide novel tachykinin-like polypeptides and their precursor polypeptides which are useful for biological, medical, and veterinarian purposes, as well as polynucleotides coding for them. Another object of the present invention is to provide recombinant vectors containing such polynucleotides, transformants transformed with such vectors, and transgenic animals having such genes containing such polynucleotides. The invention is also intended to provide a method for producing such polypeptides, antibodies against such polypeptides, agonists or antagonists, and a method for identifying them. Still another object of the present invention is to provide pharmaceutical compositions containing such polypeptides, polynucleotides, antagonists, or antibodies, as well as methods for treating or prevents diseases.

As a result of extensive research to resolve the above, the inventors succeeded in finding cDNA with a novel base sequence which is expressed in human fetuses (skeletal muscle, lungs, heart, etc.) or the human heart, human adipose tissue, human pituitary, or the like, and discovered that it coded for a precursor of a novel polypeptide ATT (atypical tachykinin). The inventors completed the present invention as a result of further research based on these findings.

That is, the present invention is intended to provide:

(1) polypeptides or amides or esters thereof, or their salts, or partial peptides or amides or esters thereof, or their salts, characterized by comprising an amino acid sequence that is the same as or substantially the same as the amino acid sequence represented by SEQ ID NO. 17.

(2) polypeptides or amides or esters thereof, or their salts, or partial peptides or amides or esters thereof, or their salts according to (1) above, characterized by comprising an amino acid sequence that is the same as or substantially the same as the amino acid sequence represented by SEQ ID NO. 7;

(3) polypeptides or amides or esters thereof, or their salts, or partial peptides or amides or esters thereof, or their salts according to (1) above, characterized by comprising an amino acid sequence that is the same as or substantially the same as the amino acid sequence represented by SEQ ID NOS. 3, 13, or 20;

(4) polypeptides or amides or esters thereof, or their salts, or partial peptides or amides or esters thereof, or their salts according to (1) above, wherein the amino acid sequence that is the same as or substantially the same as the amino acid sequence represented by SEQ ID NO. 17 is an amino acid sequence represented by SEQ ID NOS. 34, 35, 36, 37, or 38;

(5) polypeptides or amides or esters thereof, or their salts, or partial peptides or amides or esters thereof, or their salts, characterized by comprising an amino acid sequence that is the same as or substantially the same as the amino acid sequence represented by SEQ ID NO. 32;

(6) polypeptides or amides or esters thereof, or their salts, or partial peptides or amides or esters thereof, or their salts according to (5) above, characterized by comprising an amino acid sequence that is the same as or substantially the same as the amino acid sequence represented by SEQ ID NO. 22;

(7) polypeptides or amides or esters thereof, or their salts, or partial peptides or amides or esters thereof, or their salts according to (5) above, wherein the amino acid sequence that is the same as or substantially the same as the amino acid sequence represented by SEQ ID NO. 32 is an amino acid sequence represented by SEQ ID NOS. 23, 24, 25, 26, 27, or 39;

(8) polypeptides or amides or esters thereof, or their salts, or partial peptides or amides or esters thereof, or their salts according to (1) or (5) above, characterized by comprising an amino acid sequence that is the same as or substantially the same as the amino acid sequence represented by SEQ ID NO. 17 and an amino acid sequence that is the same as or substantially the same as the amino acid sequence represented by SEQ ID NO. 32;

(9) amides, or their salts, of polypeptides or partial polypeptides according to (1) or (5) above;

(10) polypeptides or partial peptides, or their salts according to (1) or (5), wherein the C terminal carboxyl group is amidated;

(11) polynucleotides comprising a polynucleotide coding for a polypeptide or partial peptide according to (1) or (5) above;

(12) polynucleotides according to (11) above, which are DNAs;

(13) polynucleotides according to (11) above, comprising a base sequence represented by SEQ ID NO. 4, 14, 21, 29, 30, 31, or 33;

(14) polynucleotides hybridizable with polynucleotides according to (11) above under stringent conditions;

(15) recombinant vectors comprising a polynucleotide according to (11) above;

(16) transformants transformed with vectors according to (15) above;

(17) a method for producing polypeptides or amides or esters thereof, or their salts, or partial peptides or amides or esters thereof, or their salts according to (1) or (5) above, characterized by culturing transformants according to (16) above to produce and accumulate polypeptides or partial peptides according to (1) or (5) above, and collecting the polypeptides or partial peptides;

(18) non-human transgenic animals into which a polynucleotide according to (11) above or a vector according to (15) above is introduced;

(19) antibodies against polypeptides or amides or esters thereof, or their salts, or partial peptides or amides or esters thereof, or their salts according to (1) or (5) above;

(20) diagnostic agents comprising antibodies according to (19) above;

(21) a method for assaying polypeptides or partial peptides according to (1) or (5) above, characterized by the use of antibodies according to (19) above;

(22) antagonists against polypeptides or amides or esters thereof, or their salts, or partial peptides or amides or esters thereof, or their salts according to (1) or (5) above;

(23) agonists for polypeptides or amides or esters thereof, or their salts, or partial peptides or amides or esters thereof, or their salts according to (1) or (5) above;

(24) agonists according to (23) above, which are agents for the prevention and/or treatment of hypertension;

(25) a method for screening antagonists according to (22) above or agonists according to (23) above, characterized by the use of polypeptides or amides or esters thereof, or their salts, or partial peptides or amides or esters thereof, or their salts according to (1) or (5) above;

(26) a screening kit for antagonists according to (22) above or agonists according to (23) above, characterized by comprising polypeptides or amides or esters thereof, or their salts, or partial peptides or amides or esters thereof, or their salts according to (1) or (5) above;

(27) pharmaceutical compositions comprising polypeptides or amides or esters thereof, or their salts, or partial peptides or amides or esters thereof, or their salts according to (1) or (5) above;

(28) pharmaceutical compositions according to (27) above, which are agents for the prevention and/or treatment of hypertension;

(29) polynucleotides comprising a base sequence, or a portion thereof, that is complementary to a polynucleotide according to (11) above;

(30) a method for assaying the mRNA of polypeptides or amides or esters thereof, or their salts, or partial peptides or amides or esters thereof, or their salts according to (1) or (5) above, characterized by the use of polynucleotides according to (11) above or portions thereof;

(31) the use of polypeptides or amides or esters thereof, or their salts, or partial peptides or amides or esters thereof, or their salts according to (1) or (5) above for the production of pharmaceutical compositions comprising polypeptides or amides or esters thereof, or their salts, or partial peptides or amides or esters thereof, or their salts according to (1) or (5) above;

(32) a method for preventing and/or treating hypertension, characterized by administering polypeptides or amides or esters thereof, or their salts, or partial peptides or amides or esters thereof, or their salts according to (1) or (5) above to mammals;

(33) the use of agonists according to (23) above for the production of drugs comprising an agonist according to (23) above; and

(34) a method for preventing and/or treating hypertension, characterized by administering an agonist according to (23) above to mammals.

SEQ ID NO. 6 from the N terminal of ATTα, ATTβ, or ATT#21F. At that time, the peptides may be subject to further limited degradation or modification. Polypeptides subject to such modification or limited degradation (referred to below as ATTshort1 (SEQ ID NO. 17) and ATTshort2 (SEQ ID NO. 22)) are included within the scope of the present invention (this polypeptide and partial peptide are sometimes referred to below as ATT or ATT polypeptide). The mature ATT produced from ATTα, ATTβ, and ATT#21F have the amino acid sequence represented by SEQ ID NO. 7, for example. Table 1 below compares the novel ATT sequence of the present invention (designated ATT in Table 1 below) and sequences of known peptides of the tachykinin family (in all examples, the carboxyl groups of the C terminal is amidated).

TABLE 1

Comparison of sequences with known peptides of tachykinin family

| | |
|---|---|
| RPKPQQFFGLM-NH₂ | Substance P |
| HKTDSFVGLM-NH₂ | Neurokinin A |
| DMHDFFVGLM-NH₂ | Neurokinin B |
| TVAGDGGEEQTLSTEAETWEGAGPSIQLQLQEVKTGKASQFFGLM-NH₂ | ATT |
| TGKASQFFGLM-NH2 | ATT-short |

BRIEF DESCRIPTION OF THE DRAWINGS

FIG. 1 illustrates the base sequence and amino acid sequence of the open reading frame of ATTα precursor;

FIG. 2 illustrates the base sequence and amino acid sequence of the open reading frame of ATTβ precursor.

Figure 3:
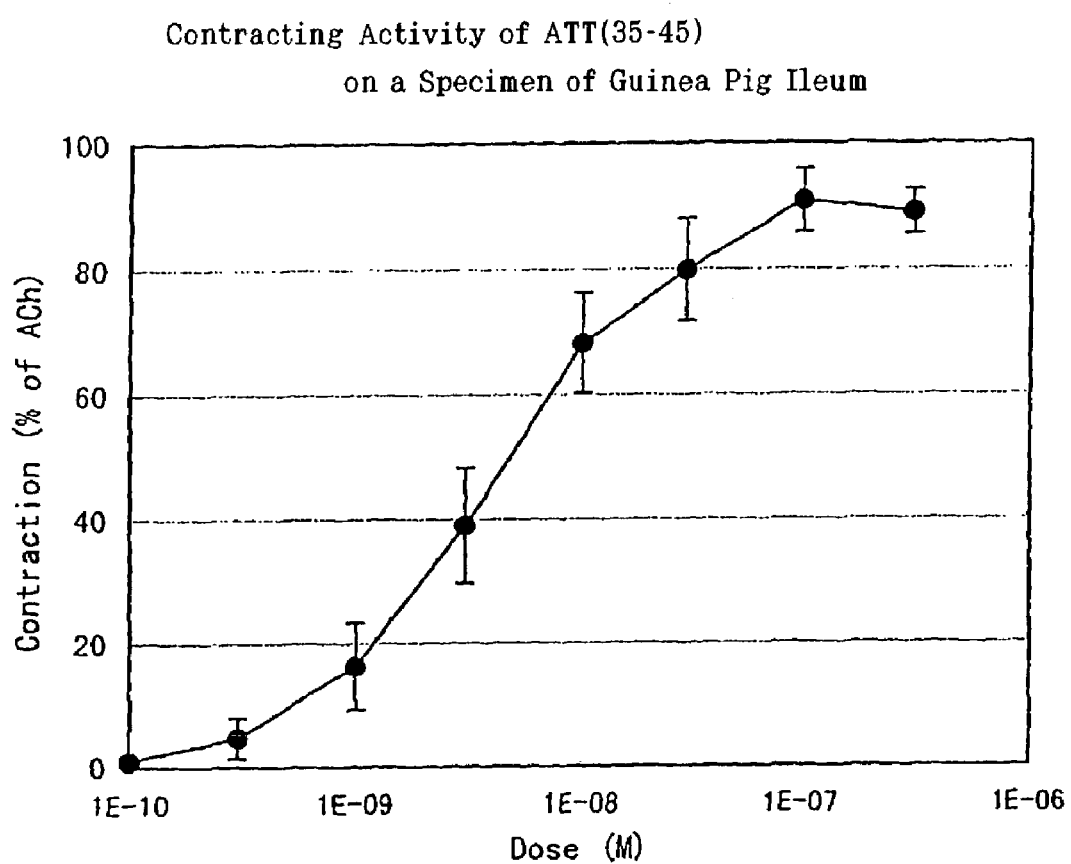
FIG. 3 illustrates the contracting action of ATT(35-45) on a specimen of guinea pig ileum.

The horizontal axis in the figure represents the dose (M) of ATT(35-45), and the vertical axis represents the rate of contraction relative to the contraction of the guinea pig ileum specimens induced by 10-6 M acetylcholine.

BEST MODE FOR CARRYING OUT THE INVENTION

There are at least three types of the novel ATT polypeptide of the present invention. The precursor designated ATTα in the present specification comprises the 68 amino acids represented by SEQ ID NO. 3. The precursor designated ATTβ in the present Specification comprises the 76 amino acids represented by SEQ ID NO. 13. ATTα and ATTβ share the same sequence up to the glycine at position 67 from the N terminal of the amino acid sequence. Based on comparison with the base sequence described below, these precursors are believed to be splice variants from the same gene.

Another precursor of the novel ATT polypeptide in the present invention is referred to as ATT#21F, comprising the 107 amino acids represented by SEQ ID NO. 20. ATT#21F shares the same sequence as ATTα and ATTβ up to the glycine at position 67 from the N terminal of the amino acid sequence.

The novel mature ATT of the present invention (SEQ ID NO. 7) (sometimes referred to below as ATT or ATT polypeptides) are produced upon the removal of the signal sequence consisting of the 16 amino acids represented by The aforementioned motif (FFGLM-NH₂) is present in the carboxyl terminal of the novel ATT of the present invention. Based on the sequence homology, the polypeptides of the present invention can be concluded to have physiological activity related to the tachykinins. The ATT of the present invention are believing to action and functions related to at least substance P, neurokinin A, and neurokinin B.

Furthermore, ATT#21F of the present invention (SEQ ID NO. 20) not only has the aforementioned motif represented by FFGLM-NH₂, but also has a carboxyl terminal sequence motif represented by Phe-Xaa-Gly-Leu-Met-NH₂ (specifically, Phe-Gln-Gly-Leu-Met-NH₂, where Xaa is any amino acid), which is not known in extant naturally occurring proteins and peptides. This physiologically active peptide precursor has a function, which has been completely unknown so far.

As used in the present specification, "polypeptides of the invention" is an expression used in a sense encompassing the aforementioned ATTα, ATTβ, ATT, ATT#21, ATTshort1, and ATTshort2. "Polypeptides of the invention" is also an expression used in a sense encompassing amides of the polypeptides of the invention, esters of polypeptides of the invention, and salts of polypeptides of the invention.

Polypeptides of the present invention and polynucleotides (such as DNA) coding for polypeptides of the present invention may be labeled by method that are well known per se. Specific examples include radioisotope-labeled types, fluorescent-labeled types (such as with fluorescein), and biotinylated types or enzyme-labeled types.

Examples of salts of polypeptides of the present invention include pharmaceutically acceptable salts with acids or bases, and especially pharmaceutically acceptable acid salts. Examples of such salts include salts of inorganic acids (such as hydrochloric acid, phosphoric acid, hydrobromic acid, and sulfuric acid), and salts of organic acids (such as acetic acid, formic acid, propionic acid, fumaric acid, maleic acid, succinic acid, tartaric acid, citric acid, malic acid, oxalic acid, benzoic acid, methanesulfonic acid, and benzenesulfonic acid).

"Polypeptides of the invention" are described in further detail below.

Polypeptides of the present invention may be synthetic polypeptides, or polypeptides derived from cells (such as spleen cells, nerve cells, glia cells, pancreatic β cells, marrow cells, mesangial cells, Langerhans' cells, epidermal cells, epithelial cells, endothelial cells, fibroblasts, fibrocytes, myocytes, adipose cells, immunocytes (such as macrophages, T cells, B cells, natural killer cells, mast cells, neutrophils, basophils, eosinophils, and monocytes), megakaryocytes, synovial cells, chondrocytes, osteocytes, osteoblasts, osteoclasts, mammary gland cells, liver cells, and interstitial cells, or their corresponding precursor cells, stem cells, cancer cells, and the like) or cells of the blood cell system, or any tissue in which such cells are present, such as the brain, regions of the brain (such as the olfactory bulb, amygdaloid nucleus, basal ganglia, hippocampus, thalamus, hypothalamus, subthalamic nucleus, cerebral cortex, medulla oblongata, cerebellum, occipital lobe, frontal lobe, temporal lobes, putamen, caudate nucleus, cerebral gland, and substantia nigra), spine, pituitary gland, stomach, pancreas, kidneys, liver, gonad, thyroid, gall bladder, bone marrow, adrenal gland, skin, muscle, lungs, gastrointestinal tract (such as the large intestine and small intestine), blood vessels, heart, thymus, spleen, submandibular gland, peripheral blood, peripheral blood cells, prostate gland, testes, ovaries, placenta, uterus, bone, joints, and skeletal muscle (and particularly the brain and regions of the brain) of humans or mammals (such as guinea pigs, rats, mice, rabbits, pigs, sheep, cows, and monkeys).

In the polypeptides of the invention, the left end is the N terminal (amino terminal) and the right end is the C terminal (carboxyl terminal), according to the usual practice for describing peptides. In the polypeptides of the present invention, including polypeptides with an amino acid sequence represented by SEQ ID No. 17 or 32, the C-terminal is usually a carboxyl group (—COOH) or a carboxylate (—COO$^-$), but the C-terminal may also be an amide (—CONH$_2$) or an ester (—COOR).

As used herein, R in such esters includes $C_1$ to $C_6$ alkyl such as methyl, ethyl, n-propyl, isopropyl, and n-butyl, $C_3$ to $C_8$ cycloalkyl such as cyclopentyl and cyclohexyl, $C_6$ to $C_{12}$ aryl such as phenyl and α-naphthyl, phenyl $C_1$ to $C_2$ alkyl such as benzyl or phenethyl, α-naphthyl-$C_1$ to $C_2$ alkyl such as α-naphthylmethyl, and other such $C_7$ to $C_{14}$ aralkyl, as well as pivaloyloxymethyl groups and the like which are commonly used as esters for oral purposes.

In cases where the polypeptides of the present invention have carboxyl groups (or carboxylates) other than at the C terminal, polypeptides in which such carboxyl groups have been converted to amides or esters are included in the polypeptides of the present invention. Esters with such C terminals may be used, for example, as esters in these cases.

The polypeptides of the present invention include such polypeptides in which the amino groups of the N terminal methionine residues are protected with protective groups (such as formyl, acetyl or other such $C_2$ to $C_6$ alkanoyl groups or similar $C_1$ to $C_6$ acyl groups), those in which the glutamyl produced upon in vivo cleavage of the N-terminal side is converted to pyroglutamate, those in which substituents (such as —OH, —SH, amino groups, imidazole groups, indole groups, and guanidine groups) on the side chains of the amino acids in the molecule are protected with suitable protective groups (such as formyl, acetyl or other such $C_2$ to $C_6$ alkanoyl groups or similar $C_1$ to $C_6$ acyl groups), and conjugated proteins such as what are referred to as glycoproteins comprising sugar linkages.

Detailed Description of Polypeptides of the Invention 1

Examples of polypeptides of the invention include:
(1) polypeptides comprising an amino acid sequence that is the same as or substantially the same as the amino acid sequence represented by SEQ ID NO. 17;
(2) polypeptides comprising an amino acid sequence that is the same as or substantially the same as the amino acid sequence represented by SEQ ID NO. 32;

Detailed Description of Polypeptides of the Invention 1-(1)

The amino acid sequence represented by SEQ ID NO. 17 is the amino acid sequence (Thr-Gly-Lys-Ala-Ser-Gln-Phe-Phe-Gly-Leu-Met) represented by positions 35 (Thr) to 45 (Met) from the N terminal of the aforementioned ATT (SEQ ID NO. 7) (the peptide comprising this sequence is sometimes referred to below as ATTshort1).

"Polypeptides comprising an amino acid sequence that is the same as or substantially the same as the amino acid sequence represented by SEQ ID NO. 17" can comprise any other amino acid sequence, provided that they also comprise an amino acid sequence that is the same as or substantially the same as the amino acid sequence represented by SEQ ID NO. 17. When the amino acid sequence that is the same as or substantially the same as the amino acid sequence represented by SEQ ID NO. 17 corresponds to the C terminal amino acid sequence of the polypeptide, the C terminal carboxyl group of the polypeptide is preferably amidated, or more specifically, the C terminal is represented by Thr-Gly-Lys-Ala-Ser-Gln-Phe-Phe-Gly-Leu-Met-NH$_2$.

Examples of amino acid sequences that are substantially the same as the amino acid sequence represented by SEQ ID NO. 17 include amino acid sequences with about at least 80%, more preferably about at least 90%, even more preferably about at least 95%, and still more preferably about at least 98% homology with the amino acid sequence represented by SEQ ID NO. 17.

As used in the present specification, homology refers to the extent of the match between two nucleotide sequences or two amino acid sequences as expressed in terms of a percentage. Computers are generally used to search homology, using the well-known Smith-Waterman algorithm and the FASTA or BLAST program, or the like.

Examples of amino acid sequences that are substantially the same as the amino acid sequence represented by SEQ ID NO. 17 include:
(i) amino acid sequences in which 1 or 2 or more (preferably 1 to about 5, and more preferably 1 to about 3, and even more preferably 1 or 2) of the amino acids in the amino acid sequence represented by SEQ ID NO. 17 have been deleted;
(ii) an amino acid sequence in which 1 or 2 or more (preferably 1 to about 5, and more preferably 1 to about 3, and even more preferably 1 or 2) amino acids have been added to the amino acid sequence represented by SEQ ID NO. 17;
(iii) an amino acid sequence in which 1 or 2 or more (preferably 1 to about 5, and more preferably 1 to about 3, and even more preferably 1 or 2) amino acids in the amino acid sequence represented by SEQ ID NO. 17 have been substituted with other amino acids;

(iv) amino acid sequences in which the amino acid sequences (i) through (iii) above are combined;

(v) amino acid sequences in which 1 to about 3, and preferably 1 or 2 amino acids other than those at positions 7 (Phe), 9 (Gly), 10 (Leu), and 11 (Met) from the N terminal in the amino acid sequence represented by SEQ ID NO. 17 have been deleted;

(vi) amino acid sequences in which 1 to about 3, and preferably 1 or 2 amino acids other than those at positions 7 (Phe), 9 (Gly), 10 (Leu), and 11 (Met) from the N terminal in the amino acid sequence represented by SEQ ID NO. 17 have been substituted with other amino acids; and (vii) amino acid sequences in which amino acid sequences (v) to (vi) above are combined.

Preferred examples of polypeptides with an amino acid sequence that is substantially the same as the amino acid sequence represented by SEQ ID NO. 17 include proteins which have an amino acid sequence that is substantially the same as the amino acid sequence represented by SEQ ID NO. 17, and which have substantially the same activity as the amino acid sequence represented by SEQ ID NO. 17.

Examples of substantially the same activity include receptor-binding activity, signal-transduction activity, the hypotensive activity described in Example 1 below, and the smooth muscle contracting activity described in Example 2 below. "Substantially the same" means that the activity is the same in terms of characteristics. As such, the receptor-binding activity, signal-transduction activity, or the like should be the same (for example, about 0.01 to 100-fold, preferably about 0.5 to 20-fold, and more preferably about 0.5 to 2-fold), although the quantitative factors such as the extent of the activity or the polypeptide molecular weight may vary.

Activity such as the receptor-binding activity or signal-transduction activity can be assayed in accordance with methods that are well known per se, such as the screening method described below.

Specific examples of polypeptides with an amino acid sequence that is the same as or substantially the same as the amino acid sequence represented by SEQ ID NO. 17 include the polypeptides described in "Detailed Description of Polypeptides of the Invention 2" and "Detailed Description of Polypeptides of the Invention 5" below, but specific preferred examples include:

(i) polypeptides consisting of an amino acid sequence represented by SEQ ID NO. 17;

(ii) polypeptides consisting of an amino acid sequence represented by SEQ ID NO. 34;

(iii) polypeptides consisting of an amino acid sequence represented by SEQ ID NO. 35;

(iv) polypeptides consisting of an amino acid sequence represented by SEQ ID NO. 36;

(v) polypeptides consisting of an amino acid sequence represented by SEQ ID NO. 37;

(vi) polypeptides consisting of an amino acid sequence represented by SEQ ID NO. 38; and (vii) polypeptides in which the C terminal carboxyl groups of the polypeptides in (i) through (vi) above are amidated.

Detailed Description of Polypeptides of the Invention 1-(2)

The amino acid sequence represented by SEQ ID NO. 32 is the amino acid sequence Phe-Xaa-Gly-Leu-Leu (where Xaa can be any amino acid) which includes the amino acid sequence from positions 85 (Phe) to 89 (Leu) from the N terminal (Phe-Gln-Gly-Leu-Leu: SEQ ID NO. 39) of the aforementioned ATT#21F (SEQ ID NO. 20).

Examples of amino acids represented by Xaa include glycine, alanine, valine, leucine, isoleucine, serine, threonine, cysteine, methionine, aspartic acid, glutamic acid, lysine, arginine, phenylalanine, tyrosine, histidine, tryptophan, asparagines, glutamine, and proline (same below).

"Polypeptides comprising an amino acid sequence that is the same as or substantially the same as the amino acid sequence represented by SEQ ID NO. 32" can comprise any other amino acid sequence, provided that they also comprise an amino acid sequence that is the same as or substantially the same as the amino acid sequence represented by SEQ ID NO. 32. When the amino acid sequence that is the same as or substantially the same as the amino acid sequence represented by SEQ ID NO. 32 corresponds to the C terminal amino acid sequence of the polypeptide, the C terminal carboxyl group of the polypeptide is preferably amidated. More specifically, the C terminal is represented by Phe-Xaa-Gly-Leu-Leu-NH$_2$ (where Xaa can be any amino acid).

Preferred examples of polypeptides with an amino acid sequence that is substantially the same as the amino acid sequence represented by SEQ ID NO. 32 include polypeptides which have an amino acid sequence that is substantially the same as the amino acid sequence represented by SEQ ID NO. 32, and which have substantially the same activity as the amino acid sequence represented by SEQ ID NO. 32.

Examples of substantially the same activity include receptor-binding activity, signal-transduction activity, the hypotensive activity described in Example 1 below, and the smooth muscle contracting activity described in Example 2 below. "Substantially the same" means that the activity is the same in terms of characteristics. As such, the receptor-binding activity, signal-transduction activity, or the like should be the same (for example, about 0.01 to 100-fold, preferably about 0.5 to 20-fold, and more preferably about 0.5 to 2-fold), although the quantitative factors such as the extent of the activity or the polypeptide molecular weight may vary.

Activity such as the receptor-binding activity or signal-transduction activity can be assayed in accordance with methods that are well known per se, such as the screening method described below.

Specific examples of polypeptides with an amino acid sequence that is the same as or substantially the same as the amino acid sequence represented by SEQ ID NO. 32 include the polypeptides described in "Detailed Description of Polypeptides of the Invention 3," "Detailed Description of Polypeptides of the Invention 4," and "Detailed Description of Polypeptides of the Invention 5" below, but specific preferred examples include:

(i) polypeptides consisting of an amino acid sequence represented by SEQ ID NO. 32;

(ii) polypeptides consisting of an amino acid sequence represented by SEQ ID NO. 39; and (iii) polypeptides in which the C terminal carboxyl groups of the polypeptides in (i) through (iii) above are amidated.

Detailed Description of Polypeptides of the
Invention 2

More specific examples of "polypeptides with an amino acid sequence that is the same as or substantially the same as the amino acid sequence represented by SEQ ID NO. 17" include:

(iii) polypeptides with an amino acid sequence that is the same as or substantially the same as the amino acid sequence represented by SEQ ID NO. 7; and (iv) polypeptides with an amino acid sequence that is the same as or substantially the same as the amino acid sequence represented by SEQ ID NO. 3, 13, or 20.

Detailed Description of Polypeptides of the
Invention 2-(1)

Polypeptides comprising an amino acid sequence represented by SEQ ID NO. 7 mean the aforementioned ATT.

"Polypeptides comprising an amino acid sequence represented by SEQ ID NO. 7" can comprise any other amino acid sequence, provided that they also comprise an amino acid sequence that is the same as or substantially the same as the amino acid sequence represented by SEQ ID NO. 7. When the amino acid sequence that is the same as or substantially the same as the amino acid sequence represented by SEQ ID NO. 7 corresponds to the C terminal amino acid sequence of the polypeptide, the C terminal carboxyl group of the polypeptide is preferably amidated, or more specifically, the C terminal is represented by Phe-Xaa-Gly-Leu-Met-NH$_2$ (where Xaa can be any amino acid).

Preferred examples of polypeptides with an amino acid sequence that is substantially the same as the amino acid sequence represented by SEQ ID NO. 7 include polypeptides which have an amino acid sequence that is the same as or substantially the same as the amino acid sequence represented by SEQ ID 17, and which have an amino acid sequence with about at least 80%, more preferably about at least 90%, even more preferably about at least 95%, and still more preferably about at least 98% homology with the amino acid sequence represented by SEQ ID NO. 7.

Examples of amino acid sequences that are substantially the same as the amino acid sequence represented by SEQ ID NO. 7 include:

(i) amino acid sequences comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) of the amino acids in the amino acid sequence represented by SEQ ID NO. 7 have been deleted;

(ii) an amino acid sequence comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) amino acids have been added to the amino acid sequence represented by SEQ ID NO. 7;

(iii) an amino acid sequence comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) amino acids in the amino acid sequence represented by SEQ ID NO. 7 have been substituted with other amino acids;

(iv) amino acid sequences in which amino acid sequences (i) through (iii) above are combined;

(v) amino acid sequences comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) amino acids from among amino acids (residues) other than those at positions 41 (Phe), 43 (Gly), 44 (Leu), and 45 (Met) from the N terminal in the amino acid sequence represented by SEQ ID NO. 7 have been deleted;

(vi) amino acid sequences comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) amino acids from among amino acids (residues) other than those at positions 41 (Phe), 43 (Gly), 44 (Leu), and 45 (Met) from the N terminal in the amino acid sequence represented by SEQ ID NO. 7 have been substituted with other amino acids; and (vii) amino acid sequences in which amino acid sequences (v) to (vi) above are combined.

Preferred examples of polypeptides with an amino acid sequence that is substantially the same as the amino acid sequence represented by SEQ ID NO. 7 include polypeptides which have an amino acid sequence that is substantially the same as the amino acid sequence represented by SEQ ID NO. 7, and which have substantially the same activity as the amino acid sequence represented by SEQ ID NO. 7.

Examples of substantially the same activity include receptor-binding activity, signal-transduction activity, the hypotensive activity described in Example 1 below, and the smooth muscle contracting activity described in Example 2 below. "Substantially the same" means that the activity is the same in terms of characteristics. As such, the receptor-binding activity, signal-transduction activity, or the like should be the same (for example, about 0.01 to 100-fold, preferably about 0.5 to 20-fold, and more preferably about 0.5 to 2-fold), although the quantitative factors such as the extent of the activity or the polypeptide molecular weight may vary.

Activity such as the receptor-binding activity or signal-transduction activity can be assayed in accordance with methods that are well known per se, such as the screening method described below.

Specific examples of polypeptides with an amino acid sequence that is the same as or substantially the same as the amino acid sequence represented by SEQ ID NO. 7 include the polypeptides described in "Detailed Description of Polypeptides of the Invention 2-(2)" below, but specific preferred examples include:

(i) polypeptides consisting of an amino acid sequence represented by SEQ ID NO. 7; and (ii) polypeptides in which the C terminal carboxyl groups of polypeptides consisting of the amino acid sequence represented by SEQ ID NO. 7 are amidated.

Detailed Description of Polypeptides of the
Invention 2-(2)

Polypeptides comprising an amino acid sequence represented by SEQ ID NO. 3 mean the aforementioned ATTα, Polypeptides comprising an amino acid sequence represented by SEQ ID NO. 13 mean the aforementioned ATTβ, and Polypeptides comprising an amino acid sequence represented by SEQ ID NO. 20 mean the aforementioned ATT#21F.

"Polypeptides comprising an amino acid sequence represented by SEQ ID NOS. 3, 13, or 20" can comprise any other amino acid sequence, provided that they also comprise an amino acid sequence that is the same as or substantially the same as the amino acid sequence represented by SEQ ID NOS. 3, 13, or 20.

Preferred examples of polypeptides with an amino acid sequence that is substantially the same as the amino acid sequences represented by SEQ ID NO. 3, 13, or 20 include polypeptides which have an amino acid sequence that is the same as or substantially the same as the amino acid sequence represented by SEQ ID 17, and which have an amino acid sequence with about at least 60%, more preferably about at least 70%, even more preferably about at least 80%, and still more preferably about at least 90% homology with the amino acid sequences represented by SEQ ID NO. 3, 13, or 20.

Examples of amino acid sequences that are substantially the same as the amino acid sequences represented by SEQ ID NOS. 3, 13, or 20 include:

(i) amino acid sequences comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) of the amino acids in the amino acid sequence represented by SEQ ID NOS. 3, 13, or 20 have been deleted;

(ii) an amino acid sequence comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) amino acids have been added to the amino acid sequence represented by SEQ ID NOS. 3, 13, or 20;

(iii) an amino acid sequence comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) amino acids in the amino acid sequence represented by SEQ ID NOS. 3, 13, or 20 have been substituted with other amino acids;

(iv) amino acid sequences in which amino acid sequences (i) through (iii) above are combined;

(v) amino acid sequences comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) amino acids from among amino acids (residues) other than those at positions 57 (Phe), 59 (Gly), 60 (Leu), and 61 (Met) from the N terminal in the amino acid sequences represented by SEQ ID NOS. 3, 13, or 20 have been deleted;

(vi) amino acid sequences comprising an amino acid sequence that is the same as or substantially the same as the amino acid sequence represented by SEQ ID NO. 17, in which 1 or 2 or more (preferably 1 to about 20, more preferably 1 to about 10, and even more preferably 1 to 5) amino acids from among amino acids (residues) other than those at positions 57 (Phe), 59 (Gly), 60 (Leu), and 61 (Met) from the N terminal in the amino acid sequences represented by SEQ ID NOS. 3, 13, or 20 have been substituted with other amino acids; and (vii) amino acid sequences in which amino acid sequences (v) to (vi) above are combined.

Preferred examples of polypeptides with an amino acid sequence that is substantially the same as the amino acid sequences represented by SEQ ID NOS. 3, 13, or 20 include polypeptides which have an amino acid sequence that is substantially the same as the amino acid sequences represented by SEQ ID NOS. 3, 13, or 20, and which have substantially the same activity as the amino acid sequences represented by SEQ ID NOS. 3, 13, or 20.

Examples of substantially the same activity include receptor-binding activity and signal-transduction activity. "Substantially the same" means that the activity is the same in terms of characteristics. However, because polypeptides which have an amino acid sequence that is substantially the same as the amino acid sequence represented by SEQ ID NOS. 3, 13, or 20 may also be obtained in the form of ATT, ATTshort1, and ATTshort2 precursor polypeptides, they need not necessarily have the physiological activity of ATT, ATTshort1, and ATTshort2 (such as the hypotensive activity described in Example 1 below or the smooth muscle contracting activity described in Example 2 below).

Specific preferred examples of polypeptides with an amino acid sequence that is the same as or substantially the same as the amino acid sequences represented by SEQ ID NOS. 3, 13, or 20 include:

(i) polypeptides consisting of an amino acid sequence represented by SEQ ID NO. 3;

(ii) polypeptides consisting of an amino acid sequence represented by SEQ ID NO. 13; and (iii) polypeptides consisting of an amino acid sequence represented by SEQ ID NO. 20.

Detailed Description of Polypeptides of the Invention 3

More specific examples of "polypeptides with an amino acid sequence that is the same as or substantially the same as the amino acid sequence represented by SEQ ID NO. 32" include:

(5) polypeptides with an amino acid sequence that is the same as or substantially the same as the amino acid sequence represented by SEQ ID NO. 22.

The amino acid sequence represented by SEQ ID NO. 22 is the amino acid sequence from positions 76 (Lys) through 89 (Leu) (Lys-Lys-Ala-Tyr-Gln-Leu-Glu-His-Thr-Phe-Gln-Gly-Leu-Leu) (the polypeptide consisting of this sequence is sometimes referred to below as "ATTshort2") from the N terminal of ATT#21F (SEQ ID NO. 20).

"Polypeptides comprising an amino acid sequence that is the same as or substantially the same as the amino acid sequence represented by SEQ ID NO. 22" can comprise any other amino acid sequence, provided that they also comprises an amino acid sequence that is the same as or substantially the same as the amino acid sequence represented by SEQ ID NO. 22. When the amino acid sequence that is the same as or substantially the same as the amino acid sequence represented by SEQ ID NO. 22 corresponds to the C terminal amino acid sequence of the polypeptide, the C terminal carboxyl group of the polypeptide is preferably amidated.

Examples of amino acid sequences that are substantially the same as the amino acid sequence represented by SEQ ID NO. 22 include amino acid sequences with about at least 80%, more preferably about at least 90%, even more preferably about at least 95%, and still more preferably about at least 98% homology with the amino acid sequence represented by SEQ ID NO. 22.

Examples of amino acid sequences that are substantially the same as the amino acid sequence represented by SEQ ID NO. 22 include:

(i) amino acid sequences comprising an amino acid sequence that is the same as or substantially the same as the amino acid sequence represented by SEQ ID NO. 32, in which 1 or 2 or more (preferably 1 to about 5, more preferably 1 to about 3, and even more preferably 1 or 2) of the amino acids in the amino acid sequence represented by SEQ ID NO. 22 have been deleted;

(ii) an amino acid sequence comprising an amino acid sequence that is the same as or substantially the same as the amino acid sequence represented by SEQ ID NO. 32, in which 1 or 2 or more (preferably 1 to about 5, more preferably 1 to about 3, and even more preferably 1 or 2) amino acids have been added to the amino acid sequence represented by SEQ ID NO. 22;

(iii) an amino acid sequence comprising an amino acid sequence that is the same as or substantially the same as the amino acid sequence represented by SEQ ID NO. 32, in which 1 or 2 or more (preferably 1 to about 5, more preferably 1 to about 3, and even more preferably 1 or 2) amino acids in the amino acid sequence represented by SEQ ID NO. 22 have been substituted with other amino acids;

(iv) amino acid sequences in which amino acid sequences (i) through (iii) above are combined;

(v) amino acid sequences comprising an amino acid sequence that is the same as or substantially the same as the amino acid sequence represented by SEQ ID NO. 32, in which 1 to about 3, and preferably 1 or 2 amino acids (residues) other than those at positions 10 (Phe), 12 (Gly), 13 (Leu), and 14 (Leu) from the N terminal in the amino acid sequence represented by SEQ ID NO. 22 have been deleted;

(vi) amino acid sequences comprising an amino acid sequence that is the same as or substantially the same as the amino acid sequence represented by SEQ ID NO. 32, in which 1 to about 3, and preferably 1 or 2 amino acids (residues) amino acids (residues) other than those at positions 10 (Phe), 12 (Gly), 13 (Leu), and 14 (Leu) from the N terminal in the amino acid sequence represented by SEQ ID NO. 22 have been substituted with other amino acids; and (vii) amino acid sequences in which amino acid sequences (v) to (vi) above are combined.

Preferred examples of polypeptides with an amino acid sequence that is substantially the same as the amino acid sequence represented by SEQ ID NO. 22 include proteins which have an amino acid sequence that is substantially the same as the amino acid sequence represented by SEQ ID NO. 22, and which have substantially the same activity as the amino acid sequence represented by SEQ ID NO. 22.

Examples of substantially the same activity include receptor-binding activity, signal-transduction activity, the hypotensive activity described in Example 1 below, and the smooth muscle contracting activity described in Example 2 below. "Substantially the same" means that the activity is the same in terms of characteristics. As such, the receptor-binding activity, signal-transduction activity, or the like should be the same (for example, about 0.01 to 100-fold, preferably about 0.5 to 20-fold, and more preferably about 0.5 to 2-fold), although the quantitative factors such as the extent of the activity or the polypeptide molecular weight may vary.

Activity such as the receptor-binding activity or signal-transduction activity can be assayed in accordance with methods that are well known per se, such as the screening method described below.

Specific examples of polypeptides with an amino acid sequence that is the same as or substantially the same as the amino acid sequence represented by SEQ ID NO. 22 include the polypeptides described in "Detailed Description of Polypeptides of the Invention 4" and "Detailed Description of Polypeptides of the Invention 5" below, but specific preferred examples include:

(i) polypeptides consisting of an amino acid sequence represented by SEQ ID NO. 22;

(ii) polypeptides consisting of an amino acid sequence represented by SEQ ID NO. 23;

(iii) polypeptides consisting of an amino acid sequence represented by SEQ ID NO. 24;

(iv) polypeptides consisting of an amino acid sequence represented by SEQ ID NO. 25;

(v) polypeptides consisting of an amino acid sequence represented by SEQ ID NO. 26;

(vi) polypeptides consisting of an amino acid sequence represented by SEQ ID NO. 27;

(vii) polypeptides consisting of an amino acid sequence represented by SEQ ID NO. 28; and (viii) polypeptides in which the C terminal carboxyl groups of the polypeptides in (i) through (vii) above are amidated.

Detailed Description of Polypeptides of the Invention 4

More specific examples of "polypeptides with an amino acid sequence that is the same as or substantially the same as the amino acid sequence represented by SEQ ID NO. 22" include:

(6) polypeptides with an amino acid sequence that is the same as or substantially the same as the amino acid sequence represented by SEQ ID NO. 20.

The polypeptide with an amino acid sequence represented by SEQ ID NO. 20 is ATT#21F.

"Polypeptides comprising an amino acid sequence that is the same as or substantially the same as the amino acid sequence represented by SEQ ID NO. 20" can comprise any other amino acid sequence, provided that they also comprise an amino acid sequence that is the same as or substantially the same as the amino acid sequence represented by SEQ ID NO. 20.

Examples of amino acid sequences that are substantially the same as the amino acid sequence represented by SEQ ID NO. 20 include amino acid sequences which comprise an amino acid sequence that is the same as or substantially the same as the amino acid sequence represented by SEQ ID NO. 22, and which have about at least 60%, more preferably about at least 70%, even more preferably about at least 80%, and still more preferably about at least 90% homology with the amino acid sequence represented by SEQ ID NO. 20.

Examples of amino acid sequences that are substantially the same as the amino acid sequence represented by SEQ ID NO. 20 include:

(i) amino acid sequences comprising an amino acid sequence that is the same as or substantially the same as the amino acid sequence represented by SEQ ID NO. 22, in which 1 or 2 or more (preferably 1 to about 20, more preferably 1 to about 10, and even more preferably 1 to 5) of the amino acids in the amino acid sequence represented by SEQ ID NO. 20 have been deleted;

(ii) an amino acid sequence comprising an amino acid sequence that is the same as or substantially the same as the amino acid sequence represented by SEQ ID No. 22, in which 1 or 2 or more (preferably 1 to about 20, more preferably 1 to about 10, and even more preferably 1 to 5) amino acids have been added to the amino acid sequence represented by SEQ ID NO. 20;

(iii) an amino acid sequence comprising an amino acid sequence that is the same as or substantially the same as the amino acid sequence represented by SEQ ID NO. 22, in which 1 or 2 or more (preferably 1 to about 20, more preferably 1 to about 10, and even more preferably 1 to 5) amino acids in the amino acid sequence represented by SEQ ID NO. 20 have been substituted with other amino acids;

(iv) amino acid sequences in which amino acid sequences (i) through (iii) above are combined;

(v) amino acid sequences comprising an amino acid sequence that is the same as or substantially the same as the amino acid sequence represented by SEQ ID NO. 22, in which 1 or 2 or more (preferably 1 to about 20, more preferably 1 to about 10, and even more preferably 1 to 5) amino acids (residues) other than those at positions 85 (Phe), 87 (Gly), 88 (Leu), and 89 (Leu) from the N terminal in the amino acid sequence represented by SEQ ID NO. 20 have been deleted;

(vi) amino acid sequences comprising an amino acid sequence that is the same as or substantially the same as the amino acid sequence represented by SEQ ID NO. 22, in which 1 or 2 or more (preferably 1 to about 20, more preferably 1 to about 10, and even more preferably 1 to 5) amino acids other than those at positions 85 (Phe), 87 (Gly), 88 (Leu), and 89 (Leu) from the N terminal in the amino acid sequence represented by SEQ ID NO. 20 have been substituted with other amino acids; and (vii) amino acid sequences in which amino acid sequences (v) to (vi) above are combined.

Preferred examples of polypeptides with an amino acid sequence that is substantially the same as the amino acid sequence represented by SEQ ID NO. 20 include peptides which have an amino acid sequence that is substantially the same as the amino acid sequence represented by SEQ ID NO. 22, and which have substantially the same activity as the amino acid sequence represented by SEQ ID NO. 20.

Examples of substantially the same activity include receptor-binding activity and signal-transduction activity. "Substantially the same" means that the activity is the same in terms of characteristics. However, because polypeptides which have an amino acid sequence that is substantially the same as the amino acid sequence represented by SEQ ID NO. 20 may also be obtained in the form of ATT, ATTshort1, as well as ATTshort2 precursor polypeptides, they need not necessarily have the physiological activity of ATT, ATTshort1, and ATTshort2 (such as the hypotensive activity described in Example 1 below or the smooth muscle contracting activity described in Example 2 below).

Specific preferred examples of polypeptides with an amino acid sequence that is the same as or substantially the same as the amino acid sequence represented by SEQ ID NO. 20 include polypeptides comprising an amino acid sequence represented by SEQ ID NO. 20.

Detailed Description of Polypeptides of the Invention 5

Specific examples of "polypeptides with an amino acid sequence that is the same as or substantially the same as the amino acid sequence represented by SEQ ID NO. 17" and "polypeptides with an amino acid sequence that is the same as or substantially the same as the amino acid sequence represented by SEQ ID NO. 32":

(7) polypeptides with an amino acid sequence that is the same as or substantially the same as the amino acid sequence represented by SEQ ID NO. 17 and an amino acid sequence that is the same as or substantially the same as the amino acid sequence represented by SEQ ID NO. 32.

"Amino acid sequences that are the same as or substantially the same as the amino acid sequence represented by SEQ ID NO. 17," "amino acid sequences that are the same as or substantially the same as the amino acid sequence represented by SEQ ID NO. 32," and polypeptides comprising those amino acid sequences are as described above.

Specific preferred examples of polypeptides comprising an amino acid sequence that is the same as or substantially the same as the amino acid sequence represented by SEQ ID NO. 17 and an amino acid sequence that is the same as or substantially the same as the amino acid sequence represented by SEQ ID NO. 32 include polypeptides consisting of the amino acid sequence represented by SEQ ID NO. 20.

Method for Producing Polypeptides of the Invention

Polypeptides of the invention can be produced from the aforementioned human and mammal cells or tissue by polypeptide purification methods that are well known per se, and can be produced by culturing transformants that have been transformed with polynucleotides (DNA) coding for polypeptides of the invention as described below. They can also be produced by the following methods of protein (polypeptide) synthesis or methods based thereon.

When the polypeptides are produced from the cells or tissue of humans or mammals, the human or mammal cells or tissue can be homogenized and then extracted with an acid or the like, and the extract can be purified and isolated by a combination of reverse phase chromatography, ion exchange chromatography, or the like.

Commercially available protein synthesis resins can be used in the synthesis of polypeptide amides in the present invention (as noted above, polypeptide amides of the invention are sometimes referred to for the sake of convenience as "polypeptides of the invention"). Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenyl-hydroxymethyl)phenoxy resin, and 4-(2',4'-dimethoxyphenyl-Fmoc aminoethyl)phenoxy resin. The use of such resins allows amino acids having α-amino groups and side chain functional groups protected by suitable protective groups to be condensed on the resin according to the sequence of the target peptide by any of various methods of condensation, which are well-known per se. After the reaction, the polypeptide can ultimately be cut out of the resin, the various protective groups can be simultaneously removed, and a reaction can be brought about to form intramolecular disulfide bonds in a highly diluted solution, giving the target polypeptides or amides thereof.

Various activating reagents which can be used for peptide synthesis can be employed in the condensation of the aforementioned protected amino acids, although carbodiimides are particularly preferred. Examples of such carbodiimides include DCC, N,N'-diisopropylcarbodiimide, and N-ethyl-N'-(3-dimethylaminopropyl)carbodiimide. To activate synthesis with such a reagent, a racemization inhibitor additive (such as HOBt or HOOBt) and the protected amino acids can be added to the resin directly, or the inhibitor can be added to the resin after the activation of the protected amino acids, in the form of a symmetric acid anhydride or an HOBt ester or HOOBt ester.

Solvents which can be used for the activation of protected amino acids or their condensation with the resin may be selected from known solvents which can be used in peptide condensation. Examples of such solvents include acid amides such as N,N-dimethyl formamide, N,N-dimethyl acetamide, and N-methyl pyrrolidone, halohydrocarbons such as methylene chloride and chloroform, alcohols such as trifluoroethanol, sulfoxides such as dimethyl sulfoxide, ethers such as pyridine, dioxane, and tetrahydrofuran, nitriles such as acetonitrile and propionitrile, esters such as methyl acetate and ethyl acetate, or suitable mixtures thereof. The reaction temperature is selected from within the known range known to allow the formation of protein bonds, which is usually between about −20° C. to 50° C. Activated amino acid derivatives are generally used in a proportion of 1.5- to 4-fold excess. When tests employing a common ninhydrin reaction reveal insufficient condensation, the condensation reaction can be repeated without removing the protective groups until sufficient condensation has been achieved. When repeated condensation fails to result in sufficient condensation, the unreacted amino acids can be acetylated using acetic anhydride or acetylimidazole.

Protective groups for the starting material amino groups include Z, Boc, tert-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, and Fmoc.

Carboxyl groups can be protected, for example, by alkyl esterification (such as methyl, ethyl propyl, butyl, t-butyl, cyclopentyl, cyclohexyl, cycloheptyl, cyclooctyl, 2-adamantyl or similar linear, branched, or cyclic alkyl esterification), aralkyl esterification (such as benzyl ester, 4-nitrobenzyl ester, 4-methoxybenzyl ester, 4-chlorobenzyl ester, and benzhydryl esterification), and phenacyl esterification, benzyloxycarbonyl hydrazidation, tert-butoxycarbonyl hydrazidation, and trityl hydrazidation.

Hydroxyl groups of serine can be protected, for example, through esterification or etherification. Groups suitable for such esterification include lower alkanoyl groups such as acetyl, aroyl groups such as benzoyl, and carbonic acid-derived groups such as benzyloxycarbonyl and ethoxycarbonyl. Groups suitable for etherification include benzyl, tetrahydropyranyl, and t-butyl.

Protective groups for the phenolic hydroxyl group of tyrosine include Bzl, $Cl_2$-Bzl, 2-nitrobenzyl, Br-Z, and t-butyl.

Examples of protective groups for the imidazole of histidine include Tos, 4-methoxy-2,3,6-trimethylbenzenesulfonyl, DNP, benzyloxymethyl, Bum, Boc, Trt, and Fmoc.

Examples of activated starting material carboxyl groups include the corresponding acid anhydrides, azides, and activated esters (esters of alcohols (such as pentachlorophenol, 2,4,5-trichlorophenol, 2,4-dinitrophenol, cyanomethyl alcohol, para-nitrophenol, HONB, N-hydroxysuccimide, N-hydroxyphthalimide, and HOBt)). Examples of activated starting material amino groups include the corresponding phosphoric amides.

Methods for eliminating (removing) protective groups include catalytic reduction in a hydrogen current in the presence of a catalyst such as Pd black or Pd-carbon, acid treatment with anhydrous hydrogen fluoride, methanesulfonic acid, trifluoromethanesulfonic acid, trifluoroacetic acid or mixtures thereof, treatment with a base such as diisopropylethylamine, triethylamine, piperidine, or piperazine, or reduction with sodium in liquid ammonia. Elimination reactions by the aforementioned acid treatment are generally brought about at a temperature of about −20 to 40° C., but it is effective to add a cation scavenger such as anisole, phenol, thioanisole, meta-cresol, para-cresol, dimethylsulfide, 1,4-butanedithiol or 1,2-ethanedithiol during the acid treatment. The 2,4-dinitrophenyl group used as a protective group for the imidazole of histidine is eliminated by thiophenol treatment, and the formyl group used as the protective group for the indole of tryptophan may be deprotected by acid treatment in the presence of the aforementioned 1,2-ethanedithiol, 1,4-butanedithiol, or the like, and can also be removed by alkali treatment with dilute sodium hydroxide solution, dilute ammonia, or the like.

The protection and deprotection of functional groups which cannot be involved in the reaction of the starting materials, the elimination of the protective groups, the activation of functional groups involved in the reaction, and the like can be selected from the appropriate known groups and methods.

Another method for obtaining polypeptide amides is to first protect the α-carboxyl groups of the carboxyl terminal amino acids by amidation, and to then extend the peptide (protein) chain on the amino group side to the desired length, producing proteins in which only the protective groups for the α-amino groups of the N terminal of the peptide chain have been removed and polypeptides in which only the protective groups of the carboxyl groups of the C terminal have been removed in order to condense both proteins in the aforementioned solvent mixture. The details of condensation are the same as above. The protected polypeptides obtained by condensation are purified, and all the protective groups can be removed by the aforementioned methods to obtain the desired crude polypeptides. The crude polypeptides can be purified by a number of well known techniques for that purpose, and the primary fractions can be lyophilized to give the desired polypeptide amides.

An example of a way to obtain polypeptide esters (as noted above, polypeptide esters of the present invention are sometimes referred to for the sake of convenience as "polypeptides of the invention" in the present Specification) is to condense the α-carboxyl groups of the carboxyl terminal amino acids with a desired alcohol to form an amino acid ester, and to then obtain the desired polypeptide ester in the same manner as polypeptide amides.

Polypeptides of the present invention can be produced by methods of peptide synthesis that are well-known per se. The peptides can be synthesized in either the solid or liquid phase, for example. In other words, the target peptide can be produced upon the condensation of a partial polypeptide or amino acid capable of forming a polypeptide of the invention with the remainder, and the subsequent elimination of any protective groups when the product has protective groups. The methods in (1) through (5) below are examples of commonly known methods of condensation and methods for eliminating protective groups in such cases.

(1) M. Bodanszky and M. A. Ondetti: *Peptide Synthesis*, Interscience Publishers, New York (1966);

(2) Schroeder and Luebke: *The Peptide*, Academic Press, New York (1965);

(3) Nobuo Izumiya et al.: *Fundamentals and Experiments in Peptide Synthesis*, Maruzen (1975);

(4) Haru'aki Yajima and Shunpei Sakakibara: *Biochemical Experiment Series* 1: *Protein Chemistry IV*, 205 (1977); and (5) Haru'aki Yajima (ed.), *Development of Drugs-Continued*, 14, Peptide Synthesis, Hirokawa Shoten.

Following the reaction, the partial peptides of the present invention can be purified and isolated by a combination of common methods of purification such as solvent extraction, distillation, column chromatography, liquid chromatography, and recrystallization. Polypeptides obtained in free form by the above method can be converted to a suitable salt by a common method. Conversely, polypeptides obtained in the form of salts can be converted to free form by a common method.

Description of Polynucleotides of the Invention

Examples of polynucleotides coding for polypeptides of the invention include any comprising a base sequence (DNA or RNA, and preferably DNA) coding for the aforementioned polypeptides of the invention. Examples of such polynucleotides include DNA or RNA, such as mRNA, coding for polypeptides of the present invention, and may be either double- or single-stranded. Double-stranded examples include double-stranded DNA, double-stranded RNA, or DNA:RNA hybrids. Single-stranded examples include sense strands (that is, coding strands) and antisense strands (non-coding strands).

mRNA of polypeptides of the present invention can be assayed by a method known in the literature ("New PCR and Applications" 15(7) (1997)) or a method based thereon using polynucleotides, or portions thereof, that code for polypeptides of the invention.

Examples of DNA coding for polypeptides of the invention include genomic DNA, genomic DNA libraries, cDNA of the aforementioned tissue and cells, cDNA libraries of such tissue and cells, and synthetic DNA. Vectors used in libraries may be any from among bacteriophages, plasmids, cosmids, phagemids, and the like. Total RNA and mRNA fractions prepared from such tissue and cells can also be amplified directly by reverse transcriptase polymerase chain reaction (RT-PCR).

Examples of DNA coding for polypeptides of the present invention include DNA with the base sequence represented by SEQ ID NO. 30 or 33, or DNA which has a base sequence hybridizable under highly stringent conditions with the base sequence represented by SEQ ID NO. 30 or 33, and which codes for a receptor having substantially the same activity (such as receptor-binding activity, signal-transduction activity, the hypotensive activity described in Example 1 below, or the smooth muscle contracting activity described in Example 2 below) as polypeptides of the present invention.

Examples of DNA capable of hybridizing under highly stringent conditions with the base sequence represented by SEQ ID NO. 30 or 33 include DNA containing a base sequence with at least about 70%, preferably at least about 80%, more preferably at least 90%, and even more preferably at least 95% homology with the base sequence represented by SEQ ID NO. 30 or 33.

Hybridization can be managed in accordance with methods that are well-known per se or methods based thereon, such as the methods given in *Molecular Cloning* 2$^{nd}$ Ed. (J. Sambrook et al., Cold Spring Harbor Lab. Press (1989)). When a commercially available library is used, the method given in the accompanying protocol should be followed. Hybridization is more preferably capable of being managed under highly stringent conditions.

Highly stringent conditions refer to conditions involving, for example, a sodium concentration of about 19 to 40 mM, and preferably about 19 to 20 mM, and a temperature of about 50 to 70° C., and preferably about 60 to 65° C. A sodium concentration of about 19 mM and a temperature of about 65° C. are ideal.

More specific examples of polynucleotides (DNA) coding for polypeptides of the invention include the following:

(1) DNA with a base sequence represented by SEQ ID NO. 30 may be used as DNA coding for polypeptides of the invention having an amino acid sequence represented by SEQ ID NO. 17;

(2) DNA with a base sequence represented by SEQ ID NO. 33 may be used as DNA coding for polypeptides of the invention having an amino acid sequence represented by SEQ ID NO. 32;

(3) DNA with a base sequence represented by SEQ ID NO. 29 may be used as DNA coding for polypeptides of the invention having an amino acid sequence represented by SEQ ID NO. 7;

(4) DNA with a base sequence represented by SEQ ID NO. 4 may be used as DNA coding for polypeptides of the invention having an amino acid sequence represented by SEQ ID NO. 3;

(5) DNA with a base sequence represented by SEQ ID NO. 14 may be used as DNA coding for polypeptides of the invention having an amino acid sequence represented by SEQ ID NO. 13;

(6) DNA with a base sequence represented by SEQ ID NO. 21 may be used as DNA coding for polypeptides of the invention having an amino acid sequence represented by SEQ ID NO. 20;

(7) DNA with a base sequence represented by SEQ ID NO. 31 may be used as DNA coding for polypeptides of the invention having an amino acid sequence represented by SEQ ID NO. 22;

(8) DNA with a base sequence represented by SEQ ID NO. 40 may be used as DNA coding for polypeptides of the invention having an amino acid sequence represented by SEQ ID NO. 23;

(9) DNA with a base sequence represented by SEQ ID NO. 41 may be used as DNA coding for polypeptides of the invention having an amino acid sequence represented by SEQ ID NO. 24;

(10) DNA with a base sequence represented by SEQ ID NO. 42 may be used as DNA coding for polypeptides of the invention having an amino acid sequence represented by SEQ ID NO. 25;

(11) DNA with a base sequence represented by SEQ ID NO. 43 may be used as DNA coding for polypeptides of the invention having an amino acid sequence represented by SEQ ID NO. 26;

(12) DNA with a base sequence represented by SEQ ID NO. 44 may be used as DNA coding for polypeptides of the invention having an amino acid sequence represented by SEQ ID NO. 27;

(13) DNA with a base sequence represented by SEQ ID NO. 45 may be used as DNA coding for polypeptides of the invention having an amino acid sequence represented by SEQ ID NO. 28;

(14) DNA with a base sequence represented by SEQ ID NO. 46 may be used as DNA coding for polypeptides of the invention having an amino acid sequence represented by SEQ ID NO. 34;

(15) DNA with a base sequence represented by SEQ ID NO. 47 may be used as DNA coding for polypeptides of the invention having an amino acid sequence represented by SEQ ID NO. 35;

(16) DNA with a base sequence represented by SEQ ID NO. 48 may be used as DNA coding for polypeptides of the invention having an amino acid sequence represented by SEQ ID NO. 36;

(17) DNA with a base sequence represented by SEQ ID NO. 49 may be used as DNA coding for polypeptides of the invention having an amino acid sequence represented by SEQ ID NO. 37;

(18) DNA with a base sequence represented by SEQ ID NO. 50 may be used as DNA coding for polypeptides of the invention having an amino acid sequence represented by SEQ ID NO. 38; and

(19) DNA with a base sequence represented by SEQ ID NO. 51 may be used as DNA coding for polypeptides of the invention having an amino acid sequence represented by SEQ ID NO. 39.

Polynucleotides comprising a portion of the base sequence of DNA coding for polypeptides of the invention or a portion of a base sequence complementary to such DNA is used in the sense including both DNA as well as RNA coding for partial peptides of polypeptides in the invention.

According to the present invention, antisense polynucleotides (nucleic acid) capable of inhibiting the replication or expression of polypeptide genes of the invention can be designed and synthesized on the basis of cloned or sequenced inventive polypeptide-encoding DNA base sequence data. Such polynucleotides (nucleic acids) can hybridize with the RNA of polypeptide genes of the invention and can inhibit RNA synthesis or function or can interact with polypeptide-related RNA of the invention to regulate and inhibit the expression of polypeptide gene in the invention. Polynucleotides complementary to the selected base sequence of polypeptide-associated RNA in the invention or polynucleotides capable of specifically hybridizing with polypeptide-associated RNA in the invention are useful in regulating and inhibiting the in vivo and in vitro expression of polypeptide genes of the invention, which can be useful for the treatment or diagnosis of various diseases. The term "corresponding" means complementary to or having homology with a specific sequence of nucleic acids, base sequences, or nucleotides, including genes. "To correspond" between nucleotides, base sequences, or nucleic acid and peptides (proteins) generally indicates amino acids of the target peptide (proteins) induced from the nucleotide (nucleic acid) sequence or complement. The inventive polypeptide gene 5' end hairpin loop, 5' end 6-base-pair repeats, 5' end untranslated region, polypeptide translation initiation codon, protein coding region, ORF translation initiation codon, 3' untranslated region, 3' end palindrome region, and 3' end hairpin loop can be selected as preferred target regions, although any region within the polypeptide genes of the invention can be selected as targets.

"Antisense" refers to the relationship between the target nucleic acid and polynucleotides that are complementary to at least a portion of the target region, that is, the relationship between targets and hybridizable polynucleotides. Examples of antisense polynucleotides include polydeoxynucleotides containing 2-deoxy-D-ribose, polydeoxynucleotides containing D-ribose, and other types of polynucleotides comprising N-glycosides of purine or pyrimidine bases, or other polymers with non-nucleotide skeletons (such as commercially available protein nucleic acids and synthetic sequence-specific nucleic acid polymers) or other polymers with special linkages (provided that the polymers contain nucleotides with configurations permitting the kind of base pairing or base stacking found in DNA and RNA). They may include double- and single-stranded DNA, double- and single-stranded RNA, and DNA:RNA hybrids, as well as unmodified polynucleotides (or unmodified oligonucleotides) and those with known modifications, such as those with labels which are known in the art, those that are capped, those that have been methylated, those in which one or more natural nucleotides have been substituted with analogues, those with intramolecular nucleotide modifications such as those with uncharged linkages (for example, methyl phosphonates, phosphotriesters, phosphoramidates, and carbamates) and those with charged linkages or sulfur-containing linkages (for example, phosphorothioates and phosphorodithioates), those with pendant moieties, such as proteins (including nucleases, nuclease inhibitors, toxins, antibodies, signal peptides, and poly-L-lysine) and saccharides (such as monosaccharides), those with intercalators (such as acridine and psoralen), those containing chelators (such as metals, radioactive metals, boron, and oxidative metals), those containing alkylators, and those with modified linkages (such as a anomeric nucleic acids). "Nucleosides," "nucleotides," and "nucleic acids" include those with purine and pyrimidine bases as well as other modified heterocyclic bases. Such modifications include methylated purines and pyrimidines, acylated purines and pyrimidines, and other heterocycles. The sugar moieties of modified nucleosides or nucleotides may also be modified, such as the substitution of one or more hydroxyl with halogens, aliphatic groups, or the like, or their conversion to functional groups such as ethers or amines.

The antisense polynucleotides (nucleic acids) of the present invention comprise RNA, DNA, or modified nucleic acids (RNA, DNA). Specific examples of modified nucleic acids include, but are not limited to, nucleic acid sulfur derivatives or thiophosphate derivatives and polynucleoside amides or oligonucleoside amides resistant to degradation. The antisense nucleic acids in the present invention should be designed to achieve the following. Specifically, the antisense nucleic acids should have greater intracellular stability, the antisense nucleic acids should have higher cell permeability, they should have greater affinity for the target sense strand, and the toxicity of any toxic antisense nucleic acids should be minimized.

Many such modifications are known in the art. Examples can be found in J. Kawakami et al., *Pharm Tech Japan*, Vol. 8, pp. 247 (1992) and Vol. 8, pp. 395 (1992), and S. T. Crooke et al. ed., *Antisense Research and Applications*, CRC Press (1993).

The antisense nucleic acids of the invention can contain altered or modified sugars, bases, or linkages, they can be delivered in special systems such as liposomes and microspheres, they can be employed in gene therapy, or they can be given in conjugated form. Examples of those used in conjugated form include those conjugated to polycations such as polylysine which serve to neutralize the charge of phosphate skeletons, and substances (such as phospholipids and cholesterol) which enhance interaction with cell membranes or bring about greater nucleic acid uptake. Preferred lipids for conjugation include cholesterol or derivatives thereof (such as cholesteryl chloroformate and cholic acid). These can be conjugated to the 3' or 5' ends of nucleic acids, and can also be conjugated through bases, sugars, or intramolecular nucleoside linkages. Examples of other groups include capping groups specifically configured to the 3' or 5' ends of nucleic acids, preventing degradation by nucleases such as exonuclease or RNase. Such capping groups include, but are not limited to, hydroxyl protecting groups known in the art, including glycols such as polyethylene glycol and tetraethylene glycol.

The inhibiting activity of antisense nucleic acids can be studied using transformants of the invention, in vivo or in vitro gene expression systems of the invention, and in vivo or in vitro translation systems of polypeptides in the invention. Such nucleic acids can be applied to cells by a variety of methods that are well known per se.

The aforementioned antisense nucleic acids include those that inhibit the synthesis or function of DNA or RNA of the polypeptide genes in the invention upon hybridization with such DNA or RNA as well as upon hybridization with the untranslated regions (such as polynucleotides represented by the base sequence from positions 1 through 135 or positions 364 through 720 from the 5' end of the base sequence represented by SEQ ID NO. 5) of polypeptides of the invention.

DNA Cloning

Procedures for cloning DNA coding for polypeptides of the present invention include using synthetic DNA primers containing a portion of a base sequence of a polypeptide in the invention for amplification by PCR, or screening DNA incorporated in suitable vectors by hybridization with labeled synthetic DNA or DNA fragments coding for some or all regions of polypeptides of the present invention. Hybridization should be managed in accordance with the methods given, for example, in *Molecular Cloning* $2^{nd}$ Ed. (J. Sambrook et al., Cold Spring Harbor Lab. Press (1989)). When a commercially available library is used, the method given in the accompanying protocol should be followed.

The DNA base sequence can be modified by methods that are known per se or methods based on them, such as ODA-LA PCR, the gapped duplex method, or the Kunkel method, using a common kit such as Mutan™-Super Express Km (Takara Shuzo) or Mutan™-K (Takara Shuzo).

The cloned DNA coding for a polypeptide of the invention can be used as such or after being digested with the desired restriction enzymes or after the addition of linker DNA, depending on the intended purpose. The DNA may have ATG as the translation initiation codon on the 5' terminal side, and TAA, TGA, or TAG as the translation termination codon on the 3' terminal side. The translation initiation and termination codons can be added using suitable synthetic DNA adapters.

Expression vectors for polypeptides in the present invention can be prepared, for example, by (a) cutting out the target DNA fragment from DNA coding for a polypeptide of the present invention, and (b) ligating the DNA fragment downstream of a promoter in a suitable expression vector.

Examples of vectors which can be used include *E. coli* plasmids (such as pBR322, pBR325, pUC12, and pUC13), *Bacillus subtilis* plasmids (such as pUB110, pTP5, and pC194), yeast plasmids (such as pSH19 and pSH15), bacteriophages such as λ phages, and animal viruses such as retroviruses, vaccinia viruses, and baculoviruses, as well as pA1-11, pXT1, pRc/CMV, pRc/RSV, and pcDNA I/Neo.

Promoters that can be used in the present invention include any that are suitable for the host which is used to express the gene. Examples for animal cell hosts include SRα promoters, SV40 promoters, LTR promoters, CMV promoters, and HSV-TK promoters.

CMV promoters and SRα promoters are preferred among these. Promoters that are preferred for *E. coli* hosts include trp promoters, lac promoters, recA promoters, $\lambda P_L$ promoters, and lpp promoters; examples that are preferred for *Bacillus* hosts include SPO1 promoters, SPO2 promoters, and penp promoters; and examples that are preferred for yeast hosts include PHO5 promoters, PGK promoters, GAP promoters, and ADH promoters. Examples that are preferred for insect cell hosts include polyhedrin and P10 promoters.

In addition to the above, expression vectors can also contain enhancers, splicing signals, poly A linker signals, selection markers, SV40 replication origins (sometimes referred to below as SV40ori), and the like as needed. Examples of selection markers include the dihydrofolate reductase (sometimes referred to below simply as dhfr) gene {methotrexate (MTX) resistance}, ampicillin resistance gene (sometimes referred to below simply as Amp$^r$), and neomycin resistance gene (G418 resistance, sometimes referred to below simply as Neo$^r$). In particular, the target gene can also be selected with thymidine-free medium when the dhfr gene is used as the selection marker with CHO (dhfr⁻) cells.

A signal sequence compatible with the host can be attached to the N-terminal side of polypeptides in the present invention if needed. Examples of signal sequences for *Escherichia* hosts include PhoA signal sequences and OmpA signal sequences; examples for *Bacillus* hosts include α-amylase signal sequences and subtilisin signal sequences; examples for yeast hosts include MFα signal sequences and SUC2 signal sequences; and examples for animal cell hosts include insulin signal sequences, α-interferon signal sequences, and antibody molecule signal sequences.

The resulting vectors containing DNA coding for polypeptides of the present invention can be used to produce transformants.

Examples of hosts that can be used include *Escherichia* microorganisms, Bacillus microorganisms, yeasts, insect cells, insects, and animal cells.

Specific examples of *Escherichia* microorganisms include *Escherichia coli* K12-DH1 (*Proc. Natl. Acad. Sci. USA*, Vol. 60, 160 (1968)), JM103 (*Nucleic Acids Research*, Vol. 9, 309 (1981)), JA221 (*Journal of Molecular Biology*, Vol. 120, 517 (1978)), HB101 (*Journal of Molecular Biology*, Vol. 41, 459 (1969)), and C600 (*Genetics*, Vol. 39, 440 (1954)).

Examples of *Bacillus* microorganisms include *Bacillus subtilis* MI114 (*Gene*, Vol. 24, 255 (1983)) and 207-21 (*Journal of Biochemistry*, Vol. 95, 87 (1984)).

Examples of yeasts include *Saccharomyces cerevisiae* AH22, AH22R⁻, NA87-11A, DKD-5D, 20B-12, *Schizosaccharomyces pombe* NCYC1913 and NCYC2036, and *Pichia pastoris*.

Examples of insect cells for the AcNPV virus include established cell lines from the larvae of *Spodoptera frugiperda* (Sf cells), MG1 cells from the interior lining of the gut of *Trichoplusia ni*, High Five™ cells from *Trichoplusia ni* ova, *Mamestra brassicae* cells, and *Estigmena acrea* cells. Examples for the BmNPV virus include the *Bombyx mori* cell line (*Bombyx mori* N; BmN cells). Examples of Sf cells include Sf9 cells (ATCC CRL 1711) and Sf21 cells (both by J. L. Vaughn et al., In Vivo, 13, 213-217(1977)).

Examples of insects include silkworm larvae (Maeda et al, *Nature*, Vol. 315, 592 (1985)).

Examples of animal cells include monkey cells COS-7, Vero, Chinese hamster ovary cells (CHO cells), dhfr gene-deficient Chinese hamster ovary cells (CHO (dhfr⁻) cells) mouse L cells, mouse AtT-20, mouse myeloma cells, rat GH3, and human FL cells.

*Escherichia* microorganisms can be transformed in accordance with methods as disclosed in, for example, *Proc. Natl. Acad. Sci. USA*, Vol. 69, 2110 (1972), and *Gene*, Vol. 17, 107 (1982). *Bacillus* microorganisms can be transformed in accordance with methods as disclosed in, for example, *Molecular & General Genetics*, Vol. 168, 111 (1979).

Yeasts can be transformed in accordance with methods as disclosed in, for example, *Methods in Enzymology*, Vol. 194, 182-187 (1991), and *Proc. Natl. Acad. Sci. USA*, Vol. 75, 1929 (1978).

Insect cells or insects can be transformed in accordance with methods as disclosed in, for example, *Bio/Technology*, Vol. 6, 47-55 (1988).

Animal cells can be transformed by methods as disclosed in, for example, *Saibo Kogaku [Cell Engineering]* Special Edition No. 8: *Shin Saibo Kogaku Jikken Purotokoru [New Cell Engineering Experimental Protocols]*, 263-267, published by Shujunsha (1995), and *Virology*, Vol. 52, 456 (1973).

In this manner it is possible to obtain transformants which have been transformed in expression vectors that contain DNA coding for polypeptides of the invention.

Liquid media are preferred for the culture of transformants obtained with *Escherichia* or *Bacillus* hosts, and should be prepared with the carbon sources, nitrogen sources, minerals, and the like which are needed for the growth of the transformants. Examples of carbon sources include glucose, dextrin, soluble starch, and sucrose. Examples of nitrogen sources include organic or inorganic substances such as ammonium salts, nitrates, corn steep liquor, peptone, casein, meat extract, soybean cake, and potato extract. Examples of minerals include calcium chloride, sodium dihydrogen phosphate, and magnesium chloride. Yeast extract, vitamins, growth-promoting factors, and the like may also be added. The medium pH is preferably about 5 to 8.

The preferred medium for culturing *Escherichia* microorganisms is M9 medium containing, for example, glucose and casamino acid (Miller, *Journal of Experiments in Molecular Genetics*, pp. 431-433, Cold Spring Harbor Laboratory, New York (1972)). The medium may be supplemented as needed with drugs such as 3β-indolyl acrylic acid in order to ensure promoter efficiency. *Escherichia* hosts can usually be cultured for about 3 to 24 hours at about 15 to 43° C., while stirred and aerated as needed.

*Bacillus* hosts can usually be cultured for about 6 to 24 hours at about 30 to 40° C., while aerated or stirred as needed.

Examples of media for the culture of transformants using yeast hosts include Burkholder minimum medium (K. L. Bostian et al., *Proc. Natl. Acad. Sci. USA*, Vol. 77, 4505 (1980)), and SD medium containing 0.5% casamino acid (G. A. Bitter et al., *Proc. Natl. Acad. Sci. USA*, Vol. 81, 5330 (1984)). The medium pH should be adjusted to between about 5 and 8. Culture usually lasts about 24 to 72 hours at about 20 to 35° C., while aerated and stirred as needed.

Examples of media for the culture of transformants using insect cell hosts or insect hosts include Grace's insect medium (T. C. C. Grace, *Nature*, 195, 788 (1962)) suitably supplemented with an additive such as 10% inactivated bovine serum. The medium pH should be adjusted to between about 6.2 and 6.4. Culture usually lasts about 3 to 5 days at about 27° C., while aerated and stirred as needed.

Examples of media for the culture of transformants using animal cell hosts include MEM medium supplemented with about 5 to 20% fetal calf serum (*Science*, Vol. 122, 501 (1952)), DMEM medium (*Virology*, Vol. 8, 396 (1959)), RPMI 1640 medium (*Journal of the American Medical Association*, Vol. 199, 519 (1967)), and 199 medium (Proceedings of the Society for the Biological Medicines, Vol. 73, 1 (1950)). The pH should be between about 6 and 8. Culture usually lasts about 15 to 60 hours at about 30 to 40° C., while aerated and stirred as needed.

In this manner it is possible to produce polypeptides of the present invention inside or outside the cells or cell membranes of transformants.

The cloning and selection of cells obtained upon the chromosomal incorporation of expression vectors introduced to the aforementioned animal cells is one way of ensuring the stable expression of polypeptides of the invention using animal cells. Specifically, transformants are selected using the aforementioned selection markers as indicators. Repeated cloning and selection of animal cells thus obtained using selection markers can result in stable animal cell lines with a high capacity for expressing polypeptides of the invention. When the dhfr gene is used as the selection marker, the culture can be managed as the MTX concentration is gradually increased to select for resistance, allowing animal cell lines of even higher expression to be obtained upon the intracellular amplification of DNA coding for polypeptides of the invention together with the dhfr gene.

Polypeptides of the present invention can be isolated and purified from the above cultures in the following manner.

When polypeptides of the invention are extracted from cultured bacterial cells or cultured cells, the bacterial cells or cells are collected in the usual manner after the culture and are suspended in a suitable buffer, the cells are then disrupted by common ultrasonic treatment, lysozyme treatment, and/or freeze-thawing or the like, and a crude extract of the polypeptides is then obtained by common centrifugation, filtration, or the like. The buffer may be supplemented with protein denaturants such as urea or guanidine hydrochloride, or surfactant such as Triton X-100™. When polypeptides of the invention are secreted in the culture, the cultured bacterial cells or cultured cells are separated in the usual manner from the supernatant, and the supernatant is collected.

The polypeptides of the invention contained in the resulting culture supernatant or extract can be purified by a suitable combination of isolation and purification methods that are well-known per se. Examples of such methods include: methods exploiting solubility, such as salting out or solvent precipitation; methods primarily exploiting differences in molecular weight, such as dialysis, ultrafiltration, gel filtration and SDS-polyacrylamide gel electrophoresis; methods exploiting differences in electrical charge, such as ion-exchange chromatography; methods exploiting specific affinity, such as affinity chromatography; methods exploiting differences in hydrophobicity, such as reverse-phase high-performance liquid chromatography; and methods exploiting differences in isoelectric point, such as isoelectric focusing.

Polypeptides of the invention obtained in free form can be converted to a salt by a method that is well-known per se, or a method based thereon. Conversely, polypeptides obtained in the form of salts can be converted to free form or to another salt by a method that is well-known per se, or a method based thereon.

Either before or after the purification of a polypeptide produced with recombinants, a suitable protein-modifying enzyme can be allowed to act thereon in the usual manner to add any modifications or to remove portions of the polypeptide. Examples of such protein-modifying enzymes include trypsin, chymotrypsin, arginyl endopeptidase, protein kinase, and glycosidase. In polypeptides of the invention produced by recombinants, the C terminal methionine may or may not be amidated, depending on the cells that are used. Those that are not amidated can be amidated by methods which are well known in the art.

The activity of the resulting polypeptides or their salts in the invention can be assayed enzyme immunoassay or the like using specific antibodies and binding assays with labeled receptors.

Antibodies Against Polypeptides of the Invention

Antibodies against polypeptides in the invention can be any of monoclonal or polyclonal antibodies, provided that they can recognize polypeptides of the invention.

Antibodies against polypeptides of the invention can be produced by using polypeptides of the invention as antigen according to methods that are well-known per se for producing antibodies and antiserum.

[Preparation of Monoclonal Antibodies]

(a) Preparation of Monoclonal Antibody-Producing Cells

Polypeptides of the present invention are administered, either alone or along with a carrier and diluent, to mammals at a site permitting the production of antibodies. Freund's complete adjuvant or incomplete adjuvant may also be given in order to potentiate the production of antibodies during administration. Administration is usually once every 2 to 6 weeks, for a total of about 2 to 10 times. Mammals that can be used include monkeys, rabbits, dogs, guinea pigs, mice, rats, sheep, and goats, although the use of mice and rats is preferred.

In the preparation of cells which produce monoclonal antibodies, individual animals with suitable antibody titer can be selected from the warm-blooded animals such as mice which have been immunized with antigen, the spleens or lymph nodes can be harvested 2 to 5 days after final immunization, and the antibody-producing cells obtained therefrom can be fused with myeloma cells so as to prepare monoclonal antibody-producing hybridomas. The antibody titer in antiserum can be assayed, for example, by conducting a reaction between antiserum and labeled polypeptides as described below, and by then assaying the activity of the label binding to the antibody. Fusion can be managed, for example, in accordance with the method of Koehler and Milstein (*Nature*, Vol. 256, 495, (1975)). Examples of fusion promoters include polyethylene glycol (PEG) and the Sendai virus, although the use of PEG is preferred.

Examples of myeloma cells include NS-1, P3U1, and SP2/0, although the use of P3U1 is preferred. The proportion between the number of antibody-producing cells (spleen cells) and the number of myeloma cells is preferably about 1:1 to 20:1. Efficient cell fusion can be achieved by 1 to 10 minutes of incubation at about 20 to 40° C., and preferably about 30 to 37° C., with the addition of PEG (preferably, PEG 1000 to PEG 6000) in a concentration of about 10 to 80%.

A variety of methods can be employed to screen monoclonal antibody-producing hybridomas, such as methods in which hybridoma culture supernatant is added to a solid phase (such as a microplate) to which the polypeptide antigen is adsorbed, either directly or with a carrier, and protein A or anti-immunoglobulin antibody (anti-mouse immunoglobulin antibody when the cells used for cell fusion are from a mouse) labeled with a radioactive substance, an enzyme, or the like is added to detect monoclonal antibodies binding to the solid phase; or methods in which hybridoma supernatant liquid is added to a solid phase to which anti-immunoglobulin or protein A is adsorbed, and polypeptides labeled with a radioactive substance, an enzyme, or the like are added to detect monoclonal antibodies binding to the solid phase.

Monoclonal antibodies can be selected according to methods that are well-known per se or methods based thereon. This can usually be done in animal cell media containing HAT (hypoxanthine, aminopterin, and thymidine). Any medium allowing hybridomas to grow can be used for selection and growth. Examples include RPMI 1640 medium containing 1 to 20%, and preferably 10 to 20%, fetal calf serum; GIT medium (Wako Pure Chemicals) containing 1 to 10% fetal calf serum; and serum-free medium (SFM-101, by Nissui Seiyaku) for hybridoma culture. The culture temperature is usually 20 to 40° C., and preferably about 37° C. The culture usually lasts from 5 days to 3 weeks, and preferably 1 to 2 weeks. The culture can usually take place with 5% carbon dioxide gas. The antibody titer of the hybridoma culture supernatant can be assayed in the same manner as in the aforementioned assay of the antibody titer in antiserum.

(b) Purification of Monoclonal Antibodies

The monoclonal antibodies can be isolated and purified by common methods for isolating and purifying immunoglobulin in the same manner as the isolation and purification of polyclonal antibodies (such as salting-out, precipitation with alcohol, isoelectric precipitation, electrophoresis, adsorption and desorption using ion exchangers (such as DEAE), ultracentrifugation, gel filtration, and specific methods of purification in which only antibodies are collected using an active adsorbent such as protein A or protein G, or an antigen-binding solid phase, and antibodies are obtained upon the dissociation of the bonds).

[Preparation of Polyclonal Antibodies]

Polyclonal antibodies of the present invention (meaning polyclonal antibodies against polypeptides of the invention) can be produced by methods that are well-known per se or methods based thereon. For example, an immunogen (polypeptide antigen of the invention) and carrier protein conjugate can be prepared, mammals can be immunized in the same manner as in the production of monoclonal antibodies, substances containing antibody against polypeptides of the invention can be harvested from the immunized animals, and the antibodies can be isolated and purified.

Any type of carrier protein can be crosslinked in any proportion in the immunogen-carrier protein conjugate used to immunize mammals, as long as they result in the efficient production of antibodies against hapten when crosslinked with the carrier for immunization. For example, bovine serum albumin, bovine thyroglobulin, or keyhole limpet hemocyanin can be coupled in a weight ratio of about 0.1 to 20, and preferably about 1 to about 5, per unit hapten.

Various condensation agents can be used to couple the hapten and carrier. Glutaraldehyde, carbodiimides, maleimide active esters, and active ester reagents with thiol and dithiopyridyl groups can be used.

The condensation reaction product is administered, either alone or along with a carrier and diluent, to warm-blooded animals at a site permitting the production of antibodies. Freund's complete adjuvant or incomplete adjuvant may also be given in order to potentiate the production of antibodies during administration. Administration is usually once every 2 to 6 weeks, for a total of about 3 to 10 times.

Polyclonal antibodies can be harvested from the blood, ascites fluid, or the like of mammals immunized in the manner described above, and are preferably harvested from the blood.

The antibody titer of the polyclonal antibodies in antiserum can be assayed in the same manner as in the assay of the antibody titer in serum described above. The polyclonal antibodies can be isolated and purified in accordance with methods for the isolation and purification of immunoglobulin in the same manner as the isolation and purification of the aforementioned monoclonal antibodies.

Applications of Polypeptides and the Like of the Invention

The following are applications of (i) polypeptides of the invention, (ii) polynucleotides (DNA) coding for polypeptides of the invention (sometimes referred to below simply as polynucleotide (DNA)), (iii) antibodies against polypeptides of the invention (sometimes referred to below as antibodies of the invention), and (iv) antisense DNA.

(1) Treatment and/or Prevention of Diseases in which Polypeptides of the Invention are Involved Polypeptides of the invention have physiological activity such as hypotensive activity or smooth muscle contracting activity, as noted in Examples 1 and 2 below.

Accordingly, it is highly possible that abnormal or missing DNA coding for polypeptides of the present invention or abnormal or missing DNA coding for receptor proteins of polypeptides in the invention are highly could result in the onset of various diseases such as blood pressure disorders (hypertension, for example), exocrine disorders, and cardiovascular disorders.

Polypeptides of the invention and polynucleotides (DNA) of the invention can therefore be used as drugs for the treatment and/or prevention of such diseases, for example.

For example, in patients who lack or suffer from low levels of a polypeptide of the invention, the polypeptide and DNA of the invention can be returned to normal levels by (a) administering DNA of the invention to the patient to bring about the in vivo expression of the polypeptide of the invention, (b) inserting DNA of the invention into cells to bring about expression of the polypeptide of the invention, and the cells can then be implanted in the patient, or (c) administering the polypeptide of the invention to the patient to ensure that the polypeptide functions satisfactorily or normally in the patient.

When DNA of the invention is used for the aforementioned therapeutic or prophylactic purposes, the DNA can be administered in the usual manner to humans or warm-blooded animals, either on its own or after being inserted in a suitable vector such as a retrovirus vector, adenovirus vector, or adenovirus-associated virus vector. The DNA of the invention can be given, either as such or in the form of a preparation with a physiologically acceptable carrier such as an adjuvant to enhance ingestion, using a catheter such as a hydrogel catheter or gene gun.

When polypeptides of the present invention are used for the therapeutic and prophylactic purposes described above, they should be purified to at least 90%, preferably to at least 95%, more preferably to at least 98%, and even more preferably to at least 99%.

The polypeptides of the present invention can be used, for example, orally in the form of optionally sugar-coated tablets, capsules, elixirs, microcapsules or the like, or they can be used parenterally in the form of injections such as sterile solutions or suspensions with water or other pharmaceutically acceptable liquids. These preparations can be produced, for example, by mixing a polypeptide of the invention with physiologically acceptable carriers, flavoring agents, excipients, vehicles, antiseptics, stabilizers, binders, or the like, in the unit dose forms required in generally accepted pharmaceutical practice. The content of the active ingredient in these preparations should give the appropriate dose within the specified range.

Examples of additives which can be mixed with tablets, capsules, and the like include binders such as gelatin, corn starch, tragacanth, and gum arabic; excipients such as crystalline cellulose; extenders such as corn starch, gelatin, and alginic acid; lubricants such as magnesium stearate; sweetening agents such as sucrose, lactose, and saccharin; and flavoring agents such as peppermint, akamono oil, and cherry. In the case of capsule unit dose forms, the aforementioned types of materials can also include liquid carriers such as oils and fats. Sterile compositions for injection can be formulated according to ordinary pharmaceutical practice such as the dissolution or suspension of active ingredients and naturally occurring vegetable oils such as sesame oil or coconut oil in a vehicle such as water for injection.

Aqueous liquids for injection include physiological saline and isotonic solutions containing glucose or other adjuvants (such as D-sorbitol, D-mannitol, and sodium chloride), and may be used in combination with appropriate dissolution aids such as alcohols (such as ethanol), polyalcohols (such as propylene glycol and polyethylene glycol), and nonionic surfactants (such as Polysorbate 80™ and HCO-50). Oleaginous liquids include sesame oil and soybean oil, and may be used in combination with benzyl benzoate, benzyl alcohol, or the like as dissolution aids. The above may also be blended with buffers (such as phosphate buffer and sodium acetate buffer), soothing agents (such as benzalkonium chloride and procaine hydrochloride), stabilizers (such as human serum albumin and polyethylene glycol), preservatives (such as benzyl alcohol and phenol), antioxidants, and the like. Suitable ampules are usually aseptically filled with the resulting injection liquid.

Vectors having DNA of the invention may also be similarly prepared, and are usually used parenterally.

Because such preparations are safe and have low toxicity, they can be administered, for example, to humans and warm-blooded animals (such as rats, mice, guinea pigs, rabbits, birds, sheep, pigs, cows, horses, cats, dogs, and monkeys).

The dosage of polypeptides of the present invention will vary depending on the target disease, purpose of administration, route of administration or the like, but the daily adult oral dosage of polypeptides of the invention for the treatment of hypertension, for example, may generally range from about 0.1 to 100 mg, preferably from about 1.0 to 50 mg, and even more preferably from about 1.0 to 20 mg, in terms of polypeptides (per 60 kg body weight). The single parenteral dose of polypeptides will vary depending on the purpose of administration, target disease, and the like, but in the form of an injection for adults, for example, the daily dosage of polypeptides of the invention for treatment of hypertension may usually range from about 0.01 to about 30 mg, preferably about 0.1 to about 20 mg, and even more preferably about 0.1 to about 10 mg at a time, in terms of the polypeptide of the present invention (per 60 kg body weight), given by injection to the affected site. Doses for animals can be given as calculated per 60 kg body weight.

(2) Screening of Candidate Drug Compounds for Diseases

As shown in Examples 1 and 2 below, the polypeptides of the present invention have physiological activity such as hypotensive activity and smooth muscle contracting activity, and compounds or their salts in the invention promoting these functions (specifically, agonists of polypeptides in the invention) can thus be used as drugs for the treatment and/or prevention of diseases such as blood pressure disorders (such as hypertensions), exocrine disorders, and cardiovascular diseases.

Compounds or their salts inhibiting such functions in the invention (specifically, antagonists of polypeptides in the invention) can be used, for example, as drugs for the treatment and/or prevention of allergic diseases, asthma, angina pectoris, atherosclerosis, diabetes, hyperlipemia, emesis, bone diseases, pollakiuria, AIDS, and blood pressure disorders.

Polypeptides of the invention can be used or recombinant polypeptide expression systems of the present invention can be constructed for use in receptor or binding assay systems to screen compounds or their salts which modify binding between polypeptides of the present invention and their receptors (compounds that promote or inhibit the activity of the polypeptides in the present invention) (such as peptides, proteins, non-peptide compounds, synthetic compounds, and fermented products) as agonists and antagonists. Such compounds or their salts include compounds or their salts with polypeptide receptor-mediated cell-stimulating activity (such as activity in promoting arachidonic acid release, acetylcholine release, intracellular $Ca^{2+}$ release, intracellular cAMP production, intracellular cGMP production, inositol phosphate production, changes in cell membrane potential, intracellular protein phosphorylation, c-fos activation, and decreases in pH) (that is, agonists of polypeptides in the present invention), and compounds or their salts with no such cell-stimulating activity (that is, antagonists of polypeptides in the present invention). To "modify binding with receptors" means to either inhibit or promote receptor binding.

That is, the present invention is intended to provide:

a method for screening compounds, or their salts, that promote or inhibit the activity of polypeptides of the invention, characterized by the use of a polypeptide of the invention, specifically, a method for screening compounds (compounds that promote or inhibit the activity of polypeptides in the invention: agonists or antagonists of polypeptides in the invention) or their salts which modify binding between polypeptides of the present invention and receptors of polypeptides of the invention, characterized by comparing (i) cases in which a polypeptide of the present invention is brought into contact with a polypeptide receptor or salt thereof in the invention, or a partial peptide or its salt of a polypeptide receptor in the present invention, and (ii) cases in which a polypeptide of the present invention and a test compound are brought into contact with a polypeptide receptor or salt thereof in the invention, or a partial peptide or its salt of a polypeptide receptor in the present invention.

The screening method of the present invention entails, for example, comparing assays of cell-stimulating activity or the extent to which polypeptides of the invention bind to polypeptide receptors or salts thereof in the invention, or partial peptides or their salts of polypeptide receptors in the present invention between (i) cases in which a polypeptide of the present invention is brought into contact with a polypeptide receptor or salt thereof in the invention, or a partial peptide or its salt of a polypeptide receptor in the present invention, and (ii) cases in which a polypeptide of the present invention and a test compound are brought into contact with a polypeptide receptor or salt thereof in the invention, or a partial peptide or its salt of a polypeptide receptor in the present invention.

Examples of receptors for polypeptides of the present invention include those among a variety of receptors, which have binding activity with polypeptides of the present invention, and through which the polypeptides of the present invention are found to have cell-stimulating activity on cells expressing such receptors (such as activity in promoting arachidonic acid release, acetylcholine release, intracellular $Ca^{2+}$ release, intracellular cAMP production, intracellular cGMP production, inositol phosphate production, changes in cell membrane potential, intracellular protein phosphorylation, c-fos activation, and decreases in pH).

Specific examples include:
(i) NK-1;
(ii) NK-2;
(iii) NK-3; and
(iv) NK-4.

Specific examples of such a screening method include:

(i) methods for screening compounds or their salts which modify binding between polypeptides of the present invention and polypeptide receptors of the present invention (compounds that promote or inhibit the activity of polypeptides of the present invention: agonists or antagonists of polypeptides in the invention), characterized by comparative assay of the extent to which labeled polypeptides of the present invention bind to polypeptide receptors or their salts, or partial peptides or their salts, between cases in which the labeled polypeptides of the present invention are brought into contact with polypeptide receptors or salts thereof in the invention, or partial peptides or their salts of polypeptide receptors in the present invention, and cases in which labeled polypeptides of the present invention and test compounds are brought into contact with polypeptide receptors or salts thereof in the invention, or partial peptides or their salts of polypeptide receptors in the present invention;

(ii) methods for screening compounds or their salts which modify binding between polypeptides of the present invention and polypeptide receptors of the present invention (compounds that promote or inhibit the activity of polypeptides of the present invention: agonists or antagonists of polypeptides in the invention), characterized by comparative assay of the extent to which labeled polypeptides of the present invention bind to cells or membrane fractions between cases in which labeled polypeptides of the present invention are brought into contact with cells or cell membrane fractions containing the polypeptide receptors of the present invention, and cases in which labeled polypeptides of the present invention and test compounds are brought into contact with cells or cell membrane fractions containing the polypeptide receptors of the present invention;

(iii) methods for screening compounds or their salts which modify binding between polypeptides of the present invention and polypeptide receptors of the present invention (compounds that promote or inhibit the activity of polypeptides of the present invention: agonists or antagonists of polypeptides in the invention), characterized by comparative assay of the extent to which labeled polypeptides of the present invention bind to polypeptide receptors of the present invention between cases in which labeled polypeptides of the present invention are brought into contact with polypeptide receptors of the invention expressed on cell membranes through the culture of transformants containing DNA coding for polypeptide receptors of the present invention, and cases in which labeled polypeptides of the present invention and test compounds are brought into contact with polypeptide receptors of the present invention expressed on cell membranes through the culture of transformants containing DNA coding for the polypeptide receptors of the present invention;

(iv) methods for screening compounds or their salts which modify binding between polypeptides of the present invention and polypeptide receptors of the present invention (compounds that promote or inhibit the activity of polypeptides of the present invention: agonists or antagonists of polypeptides in the invention), characterized by comparative assay of polypeptide receptor-mediated cell-stimulating activity (such as activity in promoting or inhibiting arachidonic acid release, acetylcholine release, intracellular $Ca^{2+}$ release, intracellular cAMP production, intracellular cGMP production, inositol phosphate production, changes in cell membrane potential, intracellular protein phosphorylation, c-fos activation, and decreases in pH) between cases in which compounds that activate polypeptide receptors of the present invention (such as polypeptides of the present invention) are brought into contact with cells containing polypeptide receptors of the present invention, and cases in which compounds that activate polypeptide receptors of the present invention and test compounds are brought into contact with cells containing polypeptide receptors of the present invention; and (v) methods for screening compounds or their salts which modify binding between polypeptides of the present invention and polypeptide receptors of the present invention (compounds that promote or inhibit the activity of polypeptides of the present invention: agonists or antagonists of polypeptides in the invention), characterized by comparative assay of polypeptide receptor-mediated cell-stimulating activity (such as activity in promoting or inhibiting arachidonic acid release, acetylcholine release, intracellular $Ca^{2+}$ release, intracellular cAMP production, intracellular cGMP production, inositol phosphate production, changes in cell membrane potential, intracellular protein phosphorylation, c-fos activation, and decreases in pH) between cases in which compounds that activate polypeptide receptors of the present invention (such as polypeptides of the present invention) are brought into contact with polypeptide receptors of the invention expressed on cell membranes through the culture of transformants containing DNA coding for polypeptide receptors of the present invention, and cases in which compounds that activate polypeptide receptors of the present invention and test compounds are brought into contact with polypeptide receptors of the present invention expressed on cell membranes through the culture of transformants containing DNA coding for the polypeptide receptors of the present invention.

Screening methods of the present invention are described in detail below.

The polypeptide receptors of the present invention used in the screening method of the invention may be any that recognize polypeptides of the invention as ligands, although membrane fractions and the like of human or warm-blooded animal organs are preferred. However, because of the extreme difficulties involved in procuring human organs in particular, polypeptide receptors of the present invention which have been expressed in large amounts using recombinants are suitable for use in screening.

The same methods as the aforementioned methods for producing polypeptides of the present invention can be used to produce polypeptide receptors of the invention.

The following methods of preparation should be followed when cells or cell membrane fractions containing polypeptide receptors of the present invention are used in the screening methods of the present invention.

When cells containing polypeptide receptors of the present invention are used, the cells may be immobilized with glutaraldehyde, formalin, or the like. The cells can be immobilized in accordance with a method that is well-known per se.

Cells containing polypeptide receptors of the present invention refer to host cells in which such polypeptide receptors are expressed. Desirable examples of such host cells include *Escherichia coli, Bacillus subtilis*, yeasts, insect cells, and animal cells. Host cells expressing polypeptide receptors of the present invention can be obtained in the same manner as methods for producing transformants obtained with expression vectors containing polypeptides of the invention, as described above.

Cell membrane fractions refer to fractions containing an abundance of cell membranes, which are obtained by methods that are well-known per se after the cells have been disrupted. Methods for disrupting cells include methods for crushing cells with a Potter-Elvehjem homogenizer, disruption with a Waring blender or a Polytron (manufactured by Kinematica), ultrasonic disruption, and disruption using a French press or the like, where the cells are discharged under pressure through narrow nozzles. Fractions of cell membranes are obtained primarily through fractionation with centrifugal force, such as fraction centrifugation or density gradient centrifugation. For example, cell lysates are centrifuged for a short period of time (usually about 1 to 10 minutes) at low speed (500 to 3,000 rpm), and the supernatant is then usually further centrifuged for 30 minutes to 2 hours at high speed (15,000 to 30,000 rpm), giving membrane fractions in the form of precipitate. Such membrane fractions contain an abundance of the expressed polypeptide receptors of the present invention and membrane components such as cell phospholipids or membrane proteins.

The amount of the polypeptide receptors of the invention contained in the cells or membrane fractions which contain such polypeptide receptors should be $10^3$ to $10^8$ molecules, and more preferably $10^5$ to $10^7$ molecules, per cell. The greater the amount expressed, the higher the polypeptide receptor binding activity (specific activity) per membrane fraction, which not only allows the construction of highly sensitive screening systems but also allows the assay of large amounts of sample per lot.

Suitable polypeptide receptor fractions and labeled polypeptides of the present invention, for example, can be used in methods (i) through (iii) above to screen for compounds that modify binding between polypeptides of the present invention and polypeptide receptors of the present invention (compounds that promote or inhibit the activity of polypeptides in the present invention: agonists or antagonists of polypeptides in the invention). Preferred examples of polypeptide receptor fractions of the present invention include native polypeptide receptor fractions, and recombinant polypeptide receptor fractions with equivalent activity. As used herein, "equivalent activity" means equivalent polypeptide binding activity and the like. Labeled ligands of the invention include both labeled ligands and labeled polypeptide analog compounds. Examples include ligands labeled with $[^3H]$, $[^{125}I]$, $[^{14}C]$ and $[^{35}S]$.

Specifically, in order to screen compounds that modify binding between polypeptides of the present invention and polypeptide receptors of the present invention, a receptor preparation can first be prepared by suspending cells or cell membrane fractions containing polypeptide receptors of the present invention in buffer suitable for screening. Examples of buffer include any that will not inhibit binding between polypeptides of the present invention and receptors, such as Tris-HCl buffer or phosphate buffer with a pH of 4 to 10 (and preferably a pH of 6 to 8). Surfactant such as CHAPS, Tween-80™ (by Kao-Atlas), digitonin, and deoxycholate can be added to the buffer to reduce non-specific binding. A protease inhibitor such as PMSF, leupeptin, E-64 (manufactured by Peptide Institute, Inc.), or pepstatin can also be added to inhibit the degradation of polypeptides or receptors of the invention by proteases. A certain amount (5,000 cpm to 500,000 cpm) of labeled polypeptide in the present invention is added to 0.01 to 10 mL of the above receptor solution in the presence of $10^{-10}$ M to $10^{-7}$ M test compound. A reaction tube with an excess of unlabeled polypeptide of the invention is also prepared to determine the non-specific binding (NSB). The reaction is carried out for about 20 minutes to 24 hours, and preferably about 30 minutes to 3 hours, at a temperature of about 0° C. to 50° C., and preferably about 40° C. to 37° C. After the reaction, the reaction mixture is filtered through glass fiber filter paper or the like and is washed with a suitable amount of the same buffer, and the radioactivity remaining on the glass fiber filter paper is measured with a liquid scintillation counter or γ-counter. Candidates with antagonist-inhibiting capacity can be selected from test compounds with a specific binding (B-NSB) of no more than 50%, for example, where 100% is the count ($B_0$-NSB) calculated by subtracting the non-specific binding (NSB) from the count prevailing in the absence of any competing substances ($B_0$).

Cell-stimulating activity mediated by polypeptide receptors in the present invention (such as activity in promoting arachidonic acid release, acetylcholine release, intracellular $Ca^{2+}$ release, intracellular cAMP production, intracellular cGMP production, inositol phosphate production, changes in cell membrane potential, intracellular protein phosphorylation, c-fos activation, and decreases in pH) can be assayed using a common method or a commercially available kit in methods (iv) and (v) above to screen for compounds that modify binding between polypeptides of the present invention and polypeptide receptors of the present invention (compounds that promote or inhibit the activity of polypeptides in the present invention: agonists and antagonists of polypeptides in the invention). Specifically, cells containing polypeptide receptors of the invention are first cultured in multi-well plates or the like. In performing the screening, the medium is replaced with fresh medium or a suitable buffer that is not toxic to the cells, test compound or the like is added, the mixture is incubated for a certain period of time, the cells are then extracted or the supernatant is collected, and the product is quantified according to a variety of methods. When the production of a substance serving as an indicator of cell-stimulating activity (such as arachidonic acid) proves difficult to detect because of degrading enzymes in the cells, the assay may be performed with the addition of an inhibitor for such enzymes. Activity such as the inhibition of cAMP production can be detected in terms of the inhibited production of cells whose basic production is increased with forskolin or the like.

Cells expressing suitable polypeptide receptors of the present invention are necessary for screening by assay of cell-stimulating activity. Preferred cells for expressing polypeptide receptors of the present invention include cell lines expressing such polypeptide receptors.

Examples of test compounds include peptides, proteins, non-peptide compounds, synthetic compounds, fermented products, cell extracts, plant extracts, and animal tissue extracts.

Screening kits for compounds or their salts that modify binding between polypeptides of the present invention or their precursor proteins and polypeptide receptors of the present invention (compounds that promote or inhibit the activity of polypeptides of the invention: agonists and antagonists of polypeptides in the invention) can include polypeptide receptors of the present invention or their salts, partial peptides or their salts of polypeptide receptors of the invention, cells containing polypeptide receptors of the present invention, cell membrane fractions containing polypeptide receptors of the present invention, and polypeptides of the invention.

The following are examples of such screening kits.

1. Screening Reagents (i) Assay Buffer and Washing Buffer

Hanks' balanced salt solution (by Gibco) supplemented with 0.05% bovine serum albumin (by Sigma).

This can be sterilized by filtration with a filter having a pore size of 0.45 μm, and stored at 4° C., or it can be prepared at the time of use.

(ii) Polypeptide Receptor Preparation

CHO cells expressing polypeptide receptors of the present invention are subcultured with $5 \times 10^5$ cells/well in 12-well plates, and are cultured for 2 days at 37° C. in 5% $CO_2$ and 95% air.

(iii) Labeled Ligands

Polypeptides of the present invention labeled with $[^3H]$, $[^{125}I]$, $[^{14}C]$, $[^{35}S]$ or the like.

Stored dissolved in a suitable solvent or buffer at 4° C. or −20° C., and diluted with assay buffer to 1 μM at the time of use.

(iv) Ligand Label Solution

The polypeptides of the present invention are dissolved to a concentration of 1 mM in PBS containing 0.1% bovine serum albumin (by Sigma), and stored at −20° C.

2. Assay (i) Cells expressing the polypeptide receptors of the present invention, which have been cultured in 12-well tissue culture plates, are washed twice with 1 mL assay buffer, and 490 μL assay buffer is then added per well.

(ii) 5 μL of $10^{-3}$ to $10^{-10}$ M test compound solution is added, 5 μL labeled polypeptide of the invention is then added, and a reaction is brought about for 1 hour at ambient temperature. 5 μL of $10^{-3}$ M polypeptide of the invention is added instead of test compound to determine the non-specific binding.

(iii) The reaction solution is removed, and the cells are washed 3 times with 1 mL washing buffer. The labeled polypeptide of the invention binding to the cells is dissolved in 0.2 N NaOH-1% SDS and mixed with 4 mL liquid Scintillator A (Wako Pure Chemicals).

(iv) The radioactivity is assayed using a liquid scintillation counter (Beckman), and the percent maximum binding (PMB) is determined using the following equation.

$$PMB = \{(B\text{-}NSB)/(B_0\text{-}NSB)\} \times 100$$

PMB: percent maximum binding

B: value when sample added

NSB: non-specific binding $B_0$: maximum binding {Equation 1}

Compounds or their salts obtained using the screening methods or screening kits of the invention are compounds that modify (promote or inhibit) binding between polypeptides of the invention and polypeptide receptors of the invention (compounds that promote or inhibit the activity of polypeptides of the invention: agonists and antagonists of the invention), specifically, compounds or their salts with cell-stimulating activity mediated by polypeptide receptors of the present invention (referred to as polypeptide agonists of the invention), or compounds with no such cell-stimulating activity (referred to as polypeptide antagonists of the invention). Examples of such compounds include peptides, proteins, non-peptide compounds, synthetic compounds, and fermented products. Such compounds may be novel compounds or known compounds.

The following specific methods (i) or (ii) should be followed to evaluate whether the compounds are agonists or antagonists of the polypeptides of the present invention.

(i) Binding assay is performed as indicated in the screening methods of (i) through (iii) above to obtain compounds that modify (and inhibit, in particular) binding between polypeptides of the invention and polypeptide receptors of the invention, and it is then determined whether or not the compounds have cell-stimulating activity mediated by the aforementioned polypeptide receptors of the invention. Compounds or salts with cell-stimulating activity are polypeptide agonists of the invention, while compounds or salts with no such activity are polypeptide antagonists of the invention.

(ii) (a) Test compounds are brought into contact with cells containing polypeptide receptors of the invention to assay the cell-stimulating activity mediated by the aforementioned polypeptide receptors of the invention. Compounds or their salts with cell-stimulating activity are polypeptide agonists of the invention.

(b) Cell-stimulating activity mediated by polypeptide receptors of the invention is comparatively assayed between cases in which compounds that activate polypeptide receptors of the invention (such as polypeptides of the invention or agonists of polypeptide in the invention) are brought into contact with cells containing polypeptide receptors of the invention, and cases in which test compounds and compounds that activate polypeptide receptors of the invention are brought into contact with cells containing polypeptide receptors of the invention. Compounds or their salts that are capable of reducing the cell-stimulating activity caused by compounds that activate polypeptide receptors of the invention are polypeptide antagonists of the invention.

Polypeptide agonists of the invention have action similar to the physiological activity of polypeptides of the invention on polypeptide receptors of the invention, and are therefore useful as safe drugs with low toxicity in the same manner as polypeptides of the invention (such as drugs for the treatment and/or prevention of blood pressure disorders (such as hypertension), exocrine disorders, endocrine disorders, lipid dysmetabolism, and cardiovascular diseases).

Conversely, polypeptide agonists of the invention are capable of inhibiting the physiological activity of polypeptides of the invention on polypeptide receptors of the invention, and are therefore useful as safe drugs with low toxicity in inhibiting such receptor activity (such as drugs for the treatment and/or prevention of allergic diseases, asthma, angina pectoris, atherosclerosis, diabetes, hyperlipemia, emesis, bone diseases, pollakiuria, AIDS, and blood pressure disorders).

Compounds or their salts obtained using the screening methods or screening kits of the invention can be selected from peptides, proteins, non-peptide compounds, synthetic compounds, fermented products, cell extracts, plant extracts, animal tissue extracts, plasma, or the like, and are compounds that promote or inhibit functions of the polypeptides of the invention.

Examples of salts of such compounds are the same as the examples of salts given for polypeptides of the present invention above.

Common procedures can be followed when compounds obtained using the screening methods or kits of the invention are used as the remedies and prophylactics described above. For example, they can be used in the form of tablets, capsules, elixirs, microcapsules, sterile solutions, suspensions, or the like in the same manner as drugs containing polypeptides of the invention, as described above.

Because such preparations are safe and have low toxicity, they can be administered orally and parenterally, for example, to humans and warm-blooded animals (such as mice, rats, rabbits, sheep, pigs, cows, horses, birds, cats, dogs, monkeys, and chimpanzees).

The dosage of such compounds and salts will vary depending on their activity, the target disease, purpose of administration, route of administration or the like, but the daily adult oral dosage of compounds that promote the functions of polypeptides of the invention for the treatment of hypertensions, for example, may generally range from about 0.1 to 100 mg, preferably from about 1.0 to 50 mg, and even more preferably from about 1.0 to 20 mg, in terms of compound (per 60 kg body weight). The single parenteral dose of such compounds will vary depending on the purpose of administration, target disease, and the like, but in the form of an injection for adults, for example, the daily dosage of compounds that promote the functions of polypeptides of the invention for treatment of hypertension may usually range from about 0.01 to about 30 mg, preferably about 0.1 to about 20 mg, and even more preferably about 0.1 to about 10 mg at a time, in terms of compound (per 60 kg body weight), given by intravenous injection. Doses for animals can be given as calculated per 60 kg body weight.

(3) Quantification of Polypeptides of the Invention

Antibodies against polypeptides of the invention (sometimes referred to below simply as antibodies of the invention) specifically recognize polypeptides of the invention, and can therefore be used to quantify polypeptides of the invention in analyte, particularly assay by sandwich immunoassay.

Specifically, the invention is intended to provide:

(i) a method for quantifying polypeptides of the invention in analyte, characterized by conducting a competitive reaction of antibody of the invention with analyte and labeled polypeptides of the invention to determine the proportion of labeled polypeptides of the invention binding to the antibody; and (ii) a method for quantifying polypeptides of the invention in analyte, characterized by conducting simultaneous or continuous reaction of analyte with antibody of the present invention insolubilized on a carrier and other labeled antibody of the invention, and then assaying the activity of the label on the insolubilization carrier.

In the method of quantification in (ii), one antibody should recognize the N terminal of polypeptides of the invention, and the other antibody should react with the C terminal of polypeptides of the invention.

Polypeptides of the invention can be quantified using monoclonal antibodies against polypeptides of the invention, but they can also be detected by tissue staining, or the like. For that purpose, the antibody molecules themselves may be used, and $F(ab')_2$, Fab', or Fab fractions of antibody molecules may also be used.

Quantification of polypeptides of the present invention using antibodies of the invention is not particularly limited. Any method of quantification can be used in which the amount of antibody, antigen, or antibody-antigen complex relative to the amount of antigen (such as the amount of polypeptide) in the analyte is detected by chemical or physical means, and is calculated from a standard curve prepared using a standard containing a known amount of antigen. For example, nephrometry, competitive methods, immunometric methods, and sandwich methods are suitable for use, although the use of a sandwich method, as described below, is preferred in terms of sensitivity and specificity.

Examples of labels for use in assays using labeled substances include radioisotopes, enzymes, fluorescent substances, and luminescent substances. Examples of radioisotopes include [$^{125}$I], [$^{131}$I], [$^{3}$H] and [$^{14}$C]. Examples of enzymes include those that are stable and that have high specific activity, such as β-galactosidase, β-glucosidase, alkali phosphatase, peroxidase, and malate dehydrogenase. Examples of fluorescent substances include fluorescamine and fluorescein isothiocyanate. Examples of luminescent substances include luminol, luminol derivatives, luciferin, and lucigenin. A biotin-avidin system may also be used for binding between antibody or antigen and a label.

Physical adsorption may be employed for the insolubilization of antigens or antibodies. Methods employing chemical bonding may also normally be used for the insolubilization or immobilization of polypeptides, enzymes, or the like. Examples of carriers include insoluble polysaccharides such as agarose, dextran and cellulose, synthetic resins such as polystyrene, polyacrylamide and silicone, and glass or the like.

In a sandwich method, the test liquid is allowed to react with insolubilized monoclonal antibody of the present invention (primary reaction), separate labeled monoclonal antibody of the present invention is allowed to react (secondary reaction), and the activity of the label on the insoluble carrier is then assayed so as to quantify the amount of polypeptides of the present invention in the analyte. The primary and secondary reactions may be carried out in reverse order, simultaneously, or while staggered. The label and method of insolubilization can be based on those described above. In sandwich immunoassay, the antibody used for the labeled antibody or solid phase antibody need not necessarily be one type; a mixture of two or more types of antibody may be used to improve assay sensitivity or the like.

The monoclonal antibodies of the present invention which are used in the primary and secondary reactions in the sandwich assay of polypeptides of the invention should have different binding sites for polypeptides of the invention. Specifically, the antibodies used in the primary reaction should recognize a region other than the C terminal region, such as the N terminal region, for example, whenever the antibody used in the secondary reaction recognizes the C terminal region of polypeptides in the invention.

Monoclonal antibodies of the present invention may be used in assay systems other than sandwich assay, such as competitive methods, immunometric methods, and nephrometry.

In competitive methods, labeled antigen and antigen in an analyte are allowed to undergo competitive reaction with antibody, the unreacted labeled antigen (F) and the labeled antigen (B) binding to the antibody are then separated (B/F separation), and the amount of label in either B or F is determined so as to quantify the amount of antigen in the analyte. This method of reaction can entail the use of a liquid phase method in which soluble antibody is used as the antibody. Polyethylene glycol and secondary antibody against the aforementioned antibody are used in the B/F separation. A solid phase method in which immobilized antibody is used as primary antibody, or the primary antibody is soluble and immobilized antibody is used as the secondary antibody.

In immunometric methods, immobilized antigen and antigen in analyte are allowed to undergo competitive reaction with a given amount of labeled antibody. The solid and liquid phases are then separated, or the antigen in the analyte is allowed to react with an excess of labeled antibody. The immobilized antigen is then added to allow the unreacted labeled antibody bind to the solid phase. The solid and liquid phases are then separated. The amount of label in either phase is then determined to quantify the amount of antigen in the analyte.

In nephrometry, the amount of insoluble precipitate produced as a result of an antigen-antibody reaction in gel or solution is measured. Laser nephrometry based on laser scattering or the like is suitable for use in cases involving trace amounts of antigen in analyte which result in only minute amounts of precipitate.

No special conditions, operations or the like need to be established in order to apply these individual immunoassay methods to the quantification method of the present invention. The polypeptide assay system of the present invention should be constructed based on common technical considerations known to those having ordinary skill in the art for the usual conditions and operations in the individual methods above. The general technical details can be found in references, documents, and the like.

Examples include Hiroshi Irie, Ed., *Radioimmunoassay* (published by Kodansha (1974)); Hiroshi Irie, Ed., *Radioimmunoassay, Part II* (published by Kodansha (1979)); Eiji Ishikawa et al., Ed., *Enzyme Immunoassay* (published by Igaku Shoin (1978)); Eiji Ishikawa et al., Ed., *Enzyme Immunoassay* (Second Edition) (published by Igaku Shoin (1982)); Eiji Ishikawa et al., Ed., *Enzyme Immunoassay* (Third Edition) (published by Igaku Shoin (1987)); *Methods in Enzymology* Vol. 70 (Immunochemical Techniques (Part A)); ibid. Vol. 73 (Immunochemical Techniques (Part B)); ibid. Vol. 74 (Immunochemical Techniques (Part C)); ibid. Vol. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press).

Antibodies of the present invention can be used in the manner described above for the sensitive quantification of polypeptides of the present invention.

Decreases or increases in the concentration of polypeptides of the invention can be detected through the quantification of the concentration of polypeptides of the present invention using antibodies of the present invention in order to permit the diagnosis of the presence or the high possibility of future onset of diseases such as blood pressure disorders (such as hypertension), exocrine disorders, and cardiovascular diseases.

The antibodies of the invention can also be used to detect polypeptides of the invention present in analytes such as bodily fluids and tissue. They can also be used to prepare antibody columns for use in the purification of polypeptides of the invention, to detect polypeptides of the invention in fractions during purification, to analyze the behavior of polypeptides of the invention in analyte cells, and so forth.

(4) Genetic Diagnostic Agents

Polynucleotides (DNA) of the present invention can be used as probe, for example, to detect abnormalities (genetic abnormalities) in DNA or mRNA coding for polypeptides of the invention in humans or warm-blooded animals (such as rats, mice, guinea pigs, rabbits, birds, sheep, pigs, cows, horses, cats, dogs, and monkeys), and can thus be useful as genetic diagnostic agents for ascertaining damage to, variation in, or under-expression of DNA or mRNA, or increases in or over-expression of DNA or mRNA.

Such genetic diagnostics using DNA of the invention can be managed by methods that are known per se, such as Northern hybridization or PCR-SSCP (*Genomics*, Vol. 5, 874-879 (1989); and *Proceedings of the National Academy of Sciences of the United States of America*, Vol. 86, 2766-2770 (1989)).

Under-expression revealed by Northern hybridization can permit the diagnosis of the presence or the possibility of future onset of diseases such as blood pressure disorders (hypertension), exocrine disorders, or cardiovascular diseases.

Conversely, over-expression revealed by Northern hybridization can permit the diagnosis of the presence or the possibility of future onset of diseases such as allergic diseases, asthma, angina pectoris, atherosclerosis, diabetes, hyperlipemia, emesis, bone diseases, pollakiuria, AIDS, and blood pressure disorders.

The nucleotide (DNA) sequences of the invention are also useful for identifying the chromosomes of organisms. Hybridization with certain locations on the chromosomes of a target organism can allow chromosomes related to genes of the invention to be identified and mapped. Genes involved in diseases associated with polypeptides of the invention can thus be identified by such mapping.

When polynucleotides (DNA) of the invention are used as tools to identify genes involved in diseases associated with polypeptides of the invention, the use of polynucleotides (DNA) containing base sequences coding for ATT, ATTshort1, and ATTshort2 is particularly preferred, although the use of polynucleotides (DNA) containing a base sequence coding for an amino acid sequence that included the C terminal amidation consensus (Gly-Lys-Arg) (ATT-Gly-Lys-Arg, ATTshort1-Gly-Lys-Arg, and ATTshort2-Gly-Lys-Arg) is even more preferable.

Cells from organisms having variation or diversity (or allele variation) among the polynucleotides and/or polypeptides of the invention can be detected at the level of DNA by various techniques which permit serotyping, for example. Variation in RNA can be detected using RT-PCR, for example. RT-PCR should especially be used in combination with an automatic detection system such as a commercially available image analyzer. RNA, cDNA, or genomic DNA can all be used in PCR or RT-PCR for the same purpose. An example is the ability to identify and analyze variation using PCR primers complementary to the nucleic acids coding for polypeptides of the invention.

(5) Drugs Containing Antisense DNA

Antisense DNA capable of complementarily binding to DNA of the present invention to inhibit the expression of such DNA can be used as an agent in the treatment and/or prevention of diseases such as allergic diseases, asthma, angina pectoris, atherosclerosis, diabetes, hyperlipemia, emesis, bone diseases, pollakiuria, AIDS, and blood pressure disorders.

In such antisense DNA applications, the antisense DNA can be used according to common methods, either by itself or after being incorporated into suitable vectors such as retrovirus vectors, adenovirus vectors, and adenovirus-associated virus vectors. Such antisense DNA can be given, either as such or in the form of a preparation combined with a physiologically acceptable carrier such as an adjuvant to facilitate ingestion, by means of a gene gun or a catheter such as a hydrogel catheter.

Antisense DNA can also be used as a diagnostic oligonucleotide probe to check for the presence or the expression of DNA of the present invention in tissue or cells.

(6) Drugs Containing Antibodies of the Invention

Antibodies of the invention which have activity to neutralize polypeptides of the invention can be used as drugs for the treatment and/or prevention of diseases such as allergic diseases, asthma, angina pectoris, atherosclerosis, diabetes, hyperlipemia, emesis, bone diseases, pollakiuria, AIDS, and blood pressure disorders.

Such agents containing antibodies of the present invention for the treatment and/or prevention of the aforementioned diseases can be given orally or parenterally in unmodified liquid form or in the form of suitable pharmaceutical compositions to humans or mammals (such as rats, rabbits, sheep, pigs, cows, cats, dogs, and monkeys). The dosage of will vary depending on the purpose of administration, target disease, symptoms, route of administration or the like, but the single adult dosage of antibodies of the present invention for the treatment of allergic diseases, for example, may generally range from about 0.01 to 20 mg/kg, preferably from about 0.1 to 10 mg/kg, and even more preferably from about 0.1 to 5 mg, to be given by intravenous injection about 1 to 5 times a day, and preferably about 1 to 3 times a day. A dosage based on this can be given for other types of parenteral administration or oral administration. Doses based on this can be given in other form so parenteral administration and oral administration. The dosage may be increased if symptoms are particularly serious.

Antibodies of the invention can be given as such or in the form of suitable pharmaceutical compositions. Pharmaceutical compositions used for the administration described above include the above or their salts with pharmaceutically acceptable carriers, diluents, or excipients. Such compositions may be provided in the form of preparations suitable for oral or parenteral administration.

That is, they can be used in the form of compositions for oral administration, specifically, tablets (including sugar-coated tablets and film-coated tablets), pills, granules, dispersions, capsules (including soft capsules), syrups, emulsions, and suspensions. Such compositions can be produced by methods that are known per se, and can include carriers, diluents, or excipients commonly used in the pharmaceutical field. Examples of carriers and excipients for tablets include lactose, starch, sucrose, and magnesium stearate.

Examples of compositions for parenteral use include injections, and suppositories. Injections include intravenous injections, subcutaneous injections, intracutaneous injections, intramuscular injections, and drip infusions. Such injections can be produced in accordance with methods that are known per se, such as by dissolving, suspending, or emulsifying the aforementioned antibodies or their salts in sterile aqueous or oleaginous liquids commonly used in injections. Aqueous liquids for injection include physiological saline and isotonic solutions containing glucose or other adjuvants, and may be used in combination with appropriate dissolution aids such as alcohols (such as ethanol), polyalcohols (such as propylene glycol and polyethylene glycol), and nonionic surfactants (such as Polysorbate 80™ and HCO-50 (polyoxyethylene (50 mol) adduct of hydrogenated castor oil)). Oleaginous liquids include sesame oil and soybean oil, and may be used in combination with benzyl benzoate, benzyl alcohol, and the like as dissolution aids. Suitable ampules are usually aseptically filled with the resulting injection liquid. Suppositories for rectal administration may be prepared by mixing the aforementioned antibodies or salts with a common suppository base.

The aforementioned oral and parenteral pharmaceutical compositions may be prepared in the unit dose forms suitable for the dosage of active ingredient. Such unit dose forms include tablets, pills, capsules, injections (ampules), and suppositories, and should usually contain antibody in an amount of 5 to 500 mg per unit dose form, and more preferably 5 to 100 mg in injections and 10 to 250 mg in other formulations.

The aforementioned compositions may contain other active ingredients, provided that their combination with the aforementioned antibodies does not result in any undesirable interaction.

(7) Transgenic Animals

The invention is also intended to provide non-human mammals with exogenous DNA coding for polypeptides of the present invention (sometimes referred to below simply as exogenous DNA) or mutant DNA thereof (sometimes referred to below simply as exogenous mutant DNA).

Specifically, the present invention is intended to provide:

(1) non-human mammals with exogenous DNA of the present invention or mutant DNA thereof;

(2) animals as described in (1) above, wherein the non-human mammal is a rodent;

(3) animals as described in (2) above, wherein the rodent is a mouse or rat; and (4) recombinant vectors which contain exogenous DNA or mutant DNA of the present invention, and which are capable of expression in mammals.

Non-human mammals with exogenous DNA or mutant DNA thereof in the invention (referred to below as transgenic animals of the invention) can be prepared by introducing the target DNA by means of calcium phosphate, electroporation, lipofection, agglutination, microinjection, particle gun, or DEAE-dextran or the like into germinal cells or the like, including fertilized or unfertilized eggs, or spermatozoa or their primordial cells, preferably at the embryonic stage (and more preferably at the single cell or fertilized egg cell stage, or generally within the 8-cell stage) in the development of non-human mammals. Such methods for introducing DNA can be employed to introduce target exogenous DNA of the invention into somatic cells, the organs of organisms, tissue cells, or the like for use in cell culture, tissue culture, or the like. The cells can be fused by common methods of cell fusion with the aforementioned germinal cells to create transgenic animals of the invention.

Examples of non-human mammals include cows, pigs, sheep, goats, rabbits, dogs, cats, guinea pigs, hamsters, mice, and rats. Animals that are preferred among these for the purposes of preparing disease animal models include rodents, which are characterized by relatively rapid ontogeny and life cycle, and are easy to breed, particularly mice (such as pure strains like C57BL/6 and DBA2, and hybrid strains like B6C3F$_1$, BDF$_1$, B6D2F$_1$, BALB/c, and ICR) or rats (such as Wistar and SD).

"Mammals," as used in the context of recombinant vectors capable of expression in mammals, include the non-human mammals noted above, as well as humans.

The exogenous DNA of the present invention refers not to DNA of the present invention which is inherent to non-human mammals, but refers to DNA of the present invention which has been isolated and extracted from mammals.

Examples of variant DNA in the present invention include that produced by variations (such as mutations) in the base sequence of the original DNA in the present invention, specifically, DNA with added or deleted bases, substitutions with other bases, or the like, as well as abnormal DNA.

Abnormal DNA means DNA causing the expression of abnormal polypeptides in the present invention, such as DNA causing the expression of polypeptides inhibiting the function of normal polypeptides of the invention.

Exogenous DNA of the invention may be from a mammal of either the same or different species of the target animal. To introduce DNA of the invention into a target animal, it is generally beneficial to use DNA in the form of a DNA construct which is ligated downstream of a promoter that enables expression of the DNA in animal cells. During the introduction of the human DNA of the present invention, for example, DNA constructs (such as vectors) which comprise the human DNA of the present invention ligated downstream of various promoters that enable expression of the DNA of various mammals (such as rabbits, dogs, cats, guinea pigs, hamsters, rats, and mice) that have DNA of the present invention possessing high homology with the above can be microinjected to fertilized eggs of the target mammals, such as mouse fertilized eggs, so as to construct a transgenic mammal with high expression of DNA in the present invention.

Examples of expression vectors for polypeptides of the invention include *E. coli* plasmids, *B. subtilis* plasmids, yeast plasmids, λ-phages and other bacteriophages, retroviruses such as Moloney leukemia virus, and animal viruses such as vaccinia virus and baculovirus. Preferred plasmids include *E. coli* plasmids, *B. subtilis* plasmids, and yeast plasmids.

Examples of promoters that regulate the expression of such DNA include (i) virus (such as simian virus, cytomegalovirus, Moloney leukemia virus, JC virus, papilloma virus, and poliovirus) DNA promoters; (ii) mammal (such as human, rabbit, dog, cat, guinea pig, hamster, rat, and mouse) promoters, such as albumin, insulin II, uroplakin II, elastase, erythropoietin, endothelin, muscle creatine kinase, glial fibrillary acidic protein, glutathione S-transferase, platelet-derived growth factor β, keratin K1, K10, and K14, collagen type I and type II, cyclic AMP-dependent protein kinase βI subunit, dystrophin, tartaric acid-resistant alkaline phosphatase, atrial natriuretic factor, endothelial receptor tyrosine kinase (commonly abbreviated as Tie2), sodium/potassium-exchanging adenosine triphosphatase (Na, K-ATPase), neurofilament light chain, metallothionein I and IIA, metalloprotease I tissue inhibitor, MHC Class I antigen (H-2L), H-ras, renin, dopamine β-hydroxylase, thyroid peroxidase (TPO), polypeptide chain elongation factor 1α (EF-1α), β actin, α and β-myosin heavy chain, myosin light chains 1 and 2, myelin basic protein, thyroglobulin, Thy-1, immunoglobulin, H chain variable region (VNP), serum amyloid P component, myoglobin, troponin C, smooth muscle α-actin, preproenkephalin A, and vasopressin. Preferable promoters are promoters conducive to high expression throughout the entire body, such as cytomegalovirus promoter, human polypeptide chain elongation factor 1α (EF-1α) promoter, and human and chicken β-actin promoters.

The aforementioned vectors should have a sequence for terminating the transcription of the target mRNA (generally called the terminator) in the transgenic mammal, examples of which include DNA sequences of viruses and various mammals, preferably simian virus SV40 promoter or the like.

A splicing signal, enhancer region, a portion of eukaryotic DNA intron, or the like can be ligated upstream of the 5'-end of the promoter region, between the promoter region and the translated region, or downstream of the 3'-end of the translated region, depending on the purpose, in order to ensure higher expression of the target exogenous DNA.

The translated region of normal polypeptides of the present invention can be obtained in the form of either all or part of genomic DNA from a variety of commercially available genomic DNA libraries and DNA from the liver, kidneys, thyroid cells, or fibroblasts of humans or various mammals (such as rabbits, dogs, cats, guinea pigs, hamsters, rats, and mice), or by using as starting material complementary DNA prepared by a common method from RNA of liver, kidneys, thyroid cells or fibroblasts. Exogenous abnormal DNA can be obtained by preparing translated regions in which point mutations have been induced in the translated region of normal polypeptides obtained from the aforementioned cells or tissue.

The translated region can be prepared by common DNA engineering methods in which a DNA construct capable of expression in transgenic animals is ligated downstream of the aforementioned promoter such as the above and upstream of the transcription termination site as desired.

The introduction of exogenous DNA of the present invention into the fertilized egg cell stage can be managed in such a way as to ensure its presence in all germinal cells and somatic cells of the target mammal. The presence of exogenous DNA of the invention in the germinal cells of the transgenic animal means that all offspring of the transgenic animal will have the exogenous DNA of the invention in all their germinal cells and somatic cells. The offspring of animals of this line inheriting the exogenous DNA of the invention will have the exogenous DNA of the present invention in all their germinal cells and somatic cells.

Non-human mammals with the normal exogenous DNA of the present invention can be mated to verify stable retention of the exogenous DNA, and can be bred and raised in the usual breeding environment as animals conserving the DNA.

The introduction of exogenous DNA of the invention into the fertilized oocyte stage can be managed in such a way as to ensure its excess presence in all germinal cells and somatic cells of the target mammal. The excess presence of exogenous DNA of the invention in the germinal cells of the transgenic animal means that all the offspring of the transgenic animal will have an excess of the exogenous DNA of the invention in all their germinal cells and somatic cells. The offspring of animals of this line inheriting the exogenous DNA of the invention will have an excess of the exogenous DNA of the present invention in all their germinal cells and somatic cells.

Homozygous animals having the DNA in both homologous chromosomes can be mated and bred in such a way as to ensure all offspring have an excess of such DNA.

Non-human mammals with normal DNA of the present invention are characterized by high expression of the normal DNA, and may ultimately develop disorders involving polypeptide hyperfunction as a result of the promotion of the function of normal endogenous DNA, making them useful as disease model animals. For example, normal transgenic animals of the present invention can be used to elucidate the mechanisms of disorders associated with polypeptides of the invention or hyperfunction of polypeptides of the invention, and to study methods for treating such diseases.

Mammals with normal exogenous DNA of the invention may also have exacerbated symptoms associated with free polypeptides of the invention, and can thus be used to screen drugs for the treatment of diseases associated with polypeptides of the invention.

Non-human mammals with abnormal exogenous DNA of the present invention, meanwhile, can be mated to verify stable retention of the exogenous DNA, and can be bred and raised in the usual breeding environment as animals conserving the DNA. The target exogenous DNA can also be incorporated in the aforementioned plasmids for use as starting material. DNA constructs with promoters can be prepared by common DNA engineering techniques. The introduction of abnormal DNA of the invention into the fertilized oocyte stage can be managed in such a way as to ensure its presence in all germinal cells and somatic cells of the target mammal. The presence of abnormal DNA of the invention in the germinal cells of the transgenic animal means that all offspring of the transgenic animal will have the abnormal DNA of the invention in all their germinal cells and somatic cells. The offspring of animals of this line inheriting the exogenous DNA of the invention will have the abnormal DNA of the present invention in all their germinal cells and somatic cells. Homozygous animals of both sexes having the DNA in both homologous chromosomes can be mated and bred in such a way as to ensure all offspring have the DNA.

Non-human mammals with abnormal DNA of the present invention are characterized by high expression of the abnormal DNA, and may ultimately develop disorders involving functional inactivation of polypeptides of the present invention as a result of the inhibition of the function of normal endogenous DNA, making them useful as disease model animals. For example, transgenic animals with abnormal DNA of the present invention can be used to elucidate the mechanisms of disorders involving functional inactivation of the polypeptide of the invention, and to study methods for treating such disorders.

As one specific potential use, animals with high expression of the abnormal DNA of the present invention can be used as a model for elucidating the functional inhibition of the normal polypeptide by an abnormal polypeptide of the present invention (dominant negative effect) in disorders involving functional inactivation of polypeptides of the present invention.

Mammals with abnormal exogenous DNA of the invention may also have exacerbated symptoms associated with free polypeptides of the invention, and can thus be used to screen drugs for the treatment of disorders involving functional inactivation of polypeptides of the invention.

Examples of other potential uses of the above two types of transgenic animals include:

(1) their use as sources of cells for tissue culture;

(2) analysis of the relationship to polypeptides which are specifically expressed or activated by polypeptides of the invention, based on direct analysis of DNA or RNA in tissue of transgenic mammals, or analysis of the composition of polypeptides expressed by the DNA;

(3) culture of cells from tissue containing the DNA by standard tissue culturing techniques for use in research on the function of tissue cells not generally amenable to culture;

(4) Screening of drugs which enhance cell function by using cells described in (3) above; and (5) the isolation and purification of variant polypeptides in the present invention, and the preparation of their antibodies.

Transgenic animals of the present invention can also be used to study the clinical symptoms of diseases associated with polypeptides of the invention, including disorders involving functional inactivation of polypeptides of the invention, in order to obtain more detailed pathological findings in various organs in models of diseases associated with polypeptides of the invention, with the potential for contributing to the development of novel methods of treatment, as well as research on and treatment of secondary diseases caused by such diseases.

Furthermore, various organs can be excised from transgenic animals of the invention, homogenized, and treated with a proteolytic enzyme such as trypsin to obtain free transgenic cells which can be cultured or used to establish a cell line of cultured cells. Such materials make useful research materials for studying polypeptides of the invention and elucidating their activity, such as the characterization of cells producing polypeptides of the invention, and the study of their relationship to apoptosis, differentiation, and proliferation, as well as the mechanism of their signal transduction and abnormalities thereof.

The aforementioned testing methods, quantification methods, and the like can also be used to provide a method for efficient and rapid screening of drugs for such diseases in order to develop drugs for the treatment of diseases associated with polypeptides of the invention, including disorders involving functional inactivation of polypeptides of the invention, using transgenic animals of the invention. Transgenic animals of the invention or exogenous DNA expression vectors of the present invention can also be used to study and develop DNA therapy for diseases associated with polypeptides of the invention.

(8) Knockout Animals

The present invention is also intended to provide non-human mammal embryonic stem cells in which DNA of the present invention has been inactivated, and non-human mammals with deficient expression of DNA in the invention.

Specifically, the invention is intended to provide:

(1) non-human mammal embryonic stem cells in which DNA of the present invention has been inactivated;

(2) embryonic stem cells according to (1) above, wherein the DNA is inactivated through the introduction of a reporter gene (such as the E. coli β-galactosidase gene);

(3) embryonic stem cells according to (1) above, which are neomycin-resistant;

(4) embryonic stem cells according to (1) above, wherein the non-human mammal is a rodent;

(5) embryonic stem cells according to (4) above, wherein the rodent is a mouse;

(6) non-human mammals with deficient expression of DNA in the invention, wherein the DNA of the invention has been inactivated;

(7) non-human mammals according to (6) above, wherein the DNA is inactivated through the introduction of a reporter gene (such as the E. coli β-galactosidase gene), and the reporter gene can be expressed under the control of a promoter for the DNA of the present invention;

(8) non-human mammals according to (6) above, wherein the non-human mammal is a rodent;

(9) non-human mammals according to (8) above, wherein the rodent is a mouse; and

(10) a method for screening compounds or their salts which promote or inhibit promoter activity on the DNA of the present invention, characterized by the administration of a test compound to an mammal according to (7) above to search for expression of the reporter gene.

Non-human mammal embryonic stem cells in which DNA of the invention has been inactivated refer to non-human mammal embryonic stem cells (ES cells) in which the DNA expression capacity has been inhibited through the artificial addition of mutations to DNA of the invention possessed by such non-human mammals, or such stem cells in which DNA is substantially deprived of the capacity to express polypeptides of the invention as a result of the substantial loss of the activity of polypeptides of the invention encoded by the DNA (sometimes referred to below as knockout DNA of the invention).

The same non-human mammals described above can be used.

Examples of methods for artificially introducing mutations to DNA of the present invention include the deletion of some or all of a DNA sequence, or the insertion or substitution of other DNA, by genetic engineering techniques. Such mutations should be used, for example, to shift the codon reading frame or disrupt promoter or exon functions in order to produce knockout DNA of the invention.

Specific examples of non-human mammal embryonic stem cells in which DNA of the invention has been inactivated (referred to below as DNA-inactivated ES cells of the invention or knockout ES cells of the invention) can be obtained by isolating target DNA of the invention possessed by non-human mammals, inserting a drug resistance gene, such as the neomycin resistance gene or hygromycin resistance gene, or a reporter gene, such as lacZ (β-galactosidase gene) or cat (chloramphenicol acetyl transferase gene), into the exon portions to disrupt the exon function, or inserting a DNA sequence that terminates gene transcription (such as a polyA linker signal) between exons to disable synthesis of complete mRNA, inserting the resulting DNA strand having the DNA sequence thus constructed to disrupt the gene (referred to below as targeting vector) into the chromosomes of an animal by homologous recombination, for example, and analyzing the resulting ES cells by Southern hybridization using probe comprising a DNA sequence on or near the DNA of the invention or by PCR using primers comprising the DNA sequence on the targeting vector and the DNA sequence of another region near the DNA of the invention used to produce the targeting vector, so as to screen for knockout ES cells of the invention.

Examples of original ES cells in which the DNA of the invention is to be inactivated by homologous recombination or the like include those which have already been established such as the above and new lines established according to the known method of Evans and Kaufman. For example, ES cells of the 129 line are generally used at present in the case of mouse ES cells, but since the immunological background is not very well known, it can be more beneficial to use lines which have been established using C57BL/6 or $BDF_1$ mice ($F_1$ of C57BL/6 and DBA/2), a strain obtained by improving the low fertility of the C57BL/6 breed through hybridization with DBA/2, for example, in order to obtain ES cells which are from a pure line and have a known immunological background. In addition to the advantages of fertility and healthy eggs, $BDF_1$ mice have the background of C57/BL/6 mice, so a benefit of ES cells obtained using them is that the immunological background can be converted to that of C57BL/6 mice by being back-crossed with C57BL/6 mice when producing disease model mice.

Blastocysts are commonly used 3.5 days after fertilization when establishing an ES cell line, but large numbers of early embryos can otherwise be efficiently obtained by culturing 8-cell stage embryos until the blastocyst stage.

Although ES cells of either sex may be used, male ES cells are usually more convenient for producing germ line chimeras. The sexes should also be distinguished as soon as possible in order to minimize the complexity of the culture procedures.

An example of a method for sexing ES cells is to amplify and detect the sex-determining region on the Y chromosome by PCR. Approximately $10^6$ cells are required in conventional karyotype analysis, whereas only about 1 colony of ES cells (about 50) is needed in this method. This sexing method thus permits the primary selection of ES cells in the initial stages of culture, and also allows male cells to be selected at an early stage, considerably simplifying the early stages of culture.

Secondary selection can be carried out through the verification of the number of chromosomes by G-banding, for example. The number of chromosomes of the resulting ES cells should be 100% of the normal number, but in cases where this is complicated by the physical operations or the like involved in establishing a line, the gene of the ES cell should be knocked out and recloned to normal cells (such as cells with a chromosome number 2n=40 in mice).

The embryonic stem cell line thus established is generally characterized by extremely good growth, but must be subcultured with extreme care because the ontogenic capacity tends to be lost. For example, the cell line should be cultured on suitable feeder cells such as STO fibroblasts in the presence of LIF (1 to 10,000 U/ml) in a carbon dioxide culture vessel (preferably 5% $CO_2$ and 95% air, or 5% oxygen, 5% $CO_2$, and 90% air) at about 37° C. During subculture, the cells should be treated, for example, with trypsin/EDTA solution (usually 0.001 to 0.5% trypsin/0.1 to 5 mM EDTA, and preferably about 0.1% trypsin/1 mM EDTA) to produce single cells, which are then inoculated onto fresh feeder cells. Such subculture is usually performed every 1 to 3 days, but the cells should be monitored in the meantime, and any morphologically abnormal cells that are discovered should be discarded.

ES cells can be allowed to differentiate into various types of cells, such as those of the longus capitis muscle, visceral muscles, or cardiac muscle, through monolayer culture to high density under suitable conditions, or through suspension culture until the formation of a cell mass (M. J. Evans & M. H. Kaufman, *Nature*, Vol. 292, 154 (1981); G. R. Martin, *Proc. Natl. Acad. Sci. USA*, Vol. 78, 7634 (1981); and T. C. Doetschman et al., *Journal of Embryology and Experimental Morphology*, Vol. 87, 27 (1985)). Cells with deficient expression of DNA of the present invention obtained upon the differentiation of the ES cells of the invention are useful for in vitro cytobiological analysis of polypeptides of the present invention and receptor proteins of the invention.

Non-human mammals with deficient expression of DNA of the present invention can be distinguished from normal animals by assaying the levels of mRNA in the animals in the usual manner and by indirectly comparing the levels of expression.

Examples of such non-human mammals include those noted above.

Non-human mammals with deficient expression of DNA of the present invention can be produced by knocking out DNA of the invention through homologous recombination, where a targeting vector prepared as described above is introduced to mouse embryonic stem cells or mouse oocytes, and as a result of its introduction, the DNA sequence of the targeting vector with inactivated DNA of the invention replaces DNA of the invention on the chromosomes of the mouse embryonic stem cells or mouse oocytes through genetic homologous recombination.

Cells in which DNA of the invention has been knocked out can be determined by Southern hybridization analysis with probe comprising a DNA sequence on or near DNA of the invention, or by PCR with primers comprising the DNA sequence on the targeting vector and a DNA sequence in a nearby region other than the mouse DNA of the invention used in the targeting vector. When non-human mammal embryonic stem cells are used, a cell line in which DNA of the present invention has been inactivated by homologous recombination can be cloned, the cells can be injected into non-human mammal embryos or blastocysts at a suitable stage, such as the 8-cell stage, and the resulting chimeric embryos can be transplanted to the uterus of a surrogate non-human mammal. The resulting animal will be a chimeric animal comprising both cells with the normal DNA locus of the present invention and cells with the artificially mutated DNA locus of the present invention.

When some germ cells of the chimeric animal have the mutated DNA locus of the present invention, chimeric individuals can be mated with normal individuals, and individuals in which all tissue comprises cells with the artificially mutated DNA locus of the invention can be selected from the group of individuals resulting from the above mating, on the basis of coat color, for example. The resulting individuals are usually characterized by deficient heterogeneous expression of polypeptides of the invention. The mating of individuals with deficient heterogeneous expression of polypeptides of the invention or receptor proteins of the invention can produce individuals with deficient homogeneous expression of the polypeptides of the invention or receptor proteins of the invention.

When oocytes are used, DNA solution can be injected by microinjection into the nucleus of the oocytes to produce transgenic non-human mammals with the targeting vector introduced into the chromosomes, and those animals with mutations in the DNA locus of the present invention resulting from homologous recombination can be selected in comparison to the above transgenic non-human mammals.

Individuals in which DNA of the present invention has been knocked out can be mated to verify that the resulting individuals also have the DNA knocked out, and can be bred and raised under the usual breeding conditions.

The germ line should be obtained and maintained in the usual manner. Specifically, animals of both sexes conserving the inactivated DNA can be mated to obtain homozygous animals with the inactivated DNA in both chromosomes. The resulting homozygous animals can be efficiently obtained when bred under conditions giving 1 normal individual and several homozygotes per dam. Heterozygous animals of both sexes can be mated to breed and raise heterozygous and homozygous animals with the inactivated DNA.

Non-human mammal embryonic stem cells in which DNA of the invention has been inactivated are extremely useful for producing non-human mammals with deficient expression of DNA of the invention.

Because non-human mammals with deficient expression of DNA of the invention lack various types of physiological activity which can be induced by polypeptides of the invention or receptor proteins of the invention, such animals can serve as models of disease caused by inactivation of the physiological activity of polypeptides of the invention or receptor proteins of the invention, and can thus be useful to research the causes of such diseases and to study therapies for them.

The abbreviations for bases, amino acids, and the like in the Specification and drawings are based on the abbreviations authorized by the IUPAC-IUB Commission on Biochemical Nomenclature, or other abbreviations commonly used in the art, examples of which are given below. Unless otherwise indicated, amino acid optical isomers are the L form.

DNA: deoxyribonucleic acid
cDNA: complementary deoxyribonucleic acid
A: adenine
T: thymine
G: guanine
C: cytosine
I: inosine
R: adenine (A) or guanine (G)
Y: thymine (T) or cytosine (C)
M: adenine (A) or cytosine (C)
K: guanine (G) or thymine (T)
S: guanine (G) or cytosine (C)
W: adenine (A) or thymine (T)
B: guanine (G), guanine (G) or thymine (T)
D: adenine (A), guanine (G) or thymine (T)
V: adenine (A), guanine (G) or cytosine (C)
N: adenine (A), guanine (G) , cytosine (C), or thymine (T) or another unknown base
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetracetic acid
SDS: sodium dodecylsulfate
BHA: benzhydrylamine
pMBHA: p-methylbenzhydrylamine
Tos: p-toluenesulfonyl
Bzl: benzyl
Bom: benzyloxymethyl
Boc: t-butyloxycarbonyl
DCM: dichloromethane
HOBt: 1-hydroxybenztriazole
DCC: N,N'-dicyclohexylcarbodiimide
TFA: trifluoroacetic acid
DIEA: diisopropylethylamine
Gly or G: glycine
Ala or A: alanine
Val or V: valine
Leu or L: leucine
Ile or I: isoleucine
Ser or S: serine
Thr or T: threonine
Cys or C: cystine
Met or M: methionine
Glu or E: glutamic acid
Asp or D: aspartic acid
Lys or K: lysine
Arg or R: arginine
His or H: histidine
Phe or F: phenylalanine
Tyr or Y: tyrosine
Trp or W: tryptophan
Pro or P: proline
Asn or N: asparagine
Gin or Q: glutamine
pGlu: pyroglutamic acid
NMP: N-methyl pyrrolidone
Cl-Z: 2-chlorobenzyloxycarbonyl
Br-Z: 2-bromobenzyloxycarbonyl
OcHex: cyclohexyl ester
OBzl: benzyl ester
Tos: p-toluenesulfonyl
HOBt: 1-hydroxybenztriazole
MeBzl: 4-methyl benzyl
Bom: benzyloxymethyl
DCC: N,N'-dichlorohexylcarbodiimide
BHA: benzhydrylamine
pMBHA: p-methylbenzhydrylamine
CHO: formyl The SEQ ID NOS. in the Sequence Listing of the present application indicate the following sequences.

[SEQ ID NO. 1]
base sequence of primer used in Example 1 below to clone ATTα
[SEQ ID NO. 2]
base sequence of primer used in Example 1 below to clone ATTα
[SEQ ID NO. 3]
amino acid sequence coding for ATTα
[SEQ ID NO. 4]
base sequence of DNA coding for ATTα
[SEQ ID NO. 5]
base sequence of DNA including base sequence of DNA coding for ATTα cloned in Example 1
[SEQ ID NO. 6]
amino acid sequence of secretion signal sequence of ATTα
[SEQ ID NO. 7]
amino acid sequence coding for ATT
[SEQ ID NO. 8]
base sequence of primer used in Example 2 below to clone ATTβ
[SEQ ID NO. 9]
base sequence of primer used in Examples 2 and 5 below to clone ATTβ
[SEQ ID NO. 10]
base sequence of primer used in Example 2 below to clone ATTβ
[SEQ ID NO. 11]
base sequence of primer used in Examples 2 and 5 below to clone ATTβ
[SEQ ID NO. 12]
base sequence of DNA including base sequence of DNA coding for ATTβ cloned in Example 2
[SEQ ID NO. 13]
amino acid sequence coding for ATTβ
[SEQ ID NO. 14]
base sequence of DNA coding for ATTβ
[SEQ ID NO. 15]
base sequence of primer used in Example 2 below to clone ATTβ
[SEQ ID NO. 16]
base sequence of DNA including base sequence of DNA coding for ATTη cloned in Example 2
[SEQ ID NO. 17]
amino acid sequence coding for ATTshort1
[SEQ ID NO. 18]
base sequence of DNA including base sequence of DNA coding for ATT#21F cloned in Example 5
[SEQ ID NO. 19]
insert sequence described in Example 5
[SEQ ID NO. 20]
amino acid sequence coding for ATT#21F
[SEQ ID NO. 21]
base sequence of DNA coding for ATT#21F
[SEQ ID NO. 22]
amino acid sequence coding for ATTshort2
[SEQ ID NO. 23]
amino acid sequence coding for 1 amino acid deletion at N terminal of ATTshort2 (C terminal amide synthesized in Example 8)
[SEQ ID NO. 24]
amino acid sequence coding for 2 amino acid deletion at N terminal of ATTshort2 (C terminal amide synthesized in Example 9)

[SEQ ID NO. 25]
amino acid sequence coding for 3 amino acid deletion at N terminal of ATTshort2 (C terminal amide synthesized in Example 10)
[SEQ ID NO. 26]
amino acid sequence coding for 4 amino acid deletion at N terminal of ATTshort2 (C terminal amide synthesized in Example 11)
[SEQ ID NO. 27]
amino acid sequence coding for peptide with N terminal Gln of peptide represented by SEQ ID NO. 26 converted to pyroglutamate (C terminal amide synthesized in Example 12)
[SEQ ID NO. 28]
amino acid sequence coding for peptide with Arg added to N terminal of ATTshort2 (C terminal amide synthesized in Example 13)
[SEQ ID NO. 29]
base sequence of DNA coding for ATT
[SEQ ID NO. 30]
base sequence of DNA coding for ATTshort1
[SEQ ID NO. 31]
base sequence of DNA coding for ATTshort2
[SEQ ID NO. 32]
amino acid sequence of novel motif present on C terminal of ATTshort2
[SEQ ID NO. 33]
base sequence of DNA coding for novel motif present on C terminal of ATTshort2
[SEQ ID NO. 34]
amino acid sequence coding for 1 amino acid deletion at N terminal of ATTshort1
[SEQ ID NO. 35]
amino acid sequence coding for 2 amino acid deletion at N terminal of ATTshort1
[SEQ ID NO. 36]
amino acid sequence coding for 3 amino acid deletion at N terminal of ATTshort1
[SEQ ID NO. 37]
amino acid sequence coding for 4 amino acid deletion at N terminal of ATTshort1
[SEQ ID NO. 38]
amino acid sequence coding for 5 amino acid deletion at N terminal of ATTshort1
[SEQ ID NO. 39]
amino acid sequence of 5 amino acids at C terminal of ATTshort2
[SEQ ID NO. 40]
base sequence of DNA coding for peptide with amino acid sequence represented by SEQ ID NO. 23
[SEQ ID NO. 41]
base sequence of DNA coding for peptide with amino acid sequence represented by SEQ ID NO. 24
[SEQ ID NO. 42]
base sequence of DNA coding for peptide with amino acid sequence represented by SEQ ID NO. 25
[SEQ ID NO. 43]
base sequence of DNA coding for peptide with amino acid sequence represented by SEQ ID NO. 26
[SEQ ID NO. 44]
base sequence of DNA coding for peptide with amino acid sequence represented by SEQ ID NO. 27
[SEQ ID NO. 45]
base sequence of DNA coding for peptide with amino acid sequence represented by SEQ ID NO. 28
[SEQ ID NO. 46]
base sequence of DNA coding for peptide with amino acid sequence represented by SEQ ID NO. 34
[SEQ ID NO. 47]
base sequence of DNA coding for peptide with amino acid sequence represented by SEQ ID NO. 35
[SEQ ID NO. 48]
base sequence of DNA coding for peptide with amino acid sequence represented by SEQ ID NO. 36
[SEQ ID NO. 49]
base sequence of DNA coding for peptide with amino acid sequence represented by SEQ ID NO. 37
[SEQ ID NO. 50]
base sequence of DNA coding for peptide with amino acid sequence represented by SEQ ID NO. 38
[SEQ ID NO. 51]
base sequence of DNA coding for peptide with amino acid sequence represented by SEQ ID NO. 39
[SEQ ID NO. 52]
partial base sequence of DNA coding for ATTα specifically amplified in Example 6
[SEQ ID NO. 53]
base sequence of sense strand primer used to obtain human ATTβ in Example 14
[SEQ ID NO. 54]
base sequence of antisense strand primer used to obtain human ATTβ in Example 14
[SEQ ID NO. 55]
base sequence of DNA fragment containing DNA sequence coding for human ATTβ obtained in Example 14
[SEQ ID NO. 56]
base sequence of sense strand primer used to obtain ATT#21F in Example 14
[SEQ ID NO. 57]
base sequence of antisense strand primer used to obtain ATT#21F in Example 14
[SEQ ID NO. 58]
base sequence of DNA fragment containing DNA sequence coding for human ATT#21F obtained in Example 14
[SEQ ID NO. 59]
base sequence of sense strand primer used to obtain human PPT-A in Example 14
[SEQ ID NO. 60]
base sequence of antisense strand primer used to obtain human PPT-A in Example 14
[SEQ ID NO. 61]
base sequence of sense strand primer used to obtain human PPT-A in Example 14
[SEQ ID NO. 62]
base sequence of antisense strand primer used to obtain human PPT-A in Example 14
[SEQ ID NO. 63]
amino acid sequence coding for human PPT-A obtained in Example 14
[SEQ ID NO. 64]
base sequence coding for amino acid sequence represented by SEQ ID NO. 63

The transformant *Escherichia coli* DH5α/pTBN1 obtained in Example 1 is on deposit under the accession number FERM BP-6959 at the National Institute of Bioscience and Human Technology (NIBH), Agency of Industrial Science and Technology, Ministry of International Trade and Industry, 1-1-3 Higashi, Tsukuba-shi, Ibaraki-ken, Japan as of Dec. 6, 1999, and is also on deposit under the accession number IFO 16337 at the Institute of Fermentation, Osaka (IFO), 2-17-85 Juso-honmachi, Yodogawa-ku, Osaka-shi, Japan as of Nov. 16, 1999.

The transformant *Escherichia coli* DH5α/pTBN2 obtained in Example 2 is on deposit under the accession number FERM BP-6960 at the National Institute of Bioscience and Human Technology (NIBH), Agency of Industrial Science and Technology, Ministry of International Trade and Industry, 1-1-3 Higashi, Tsukuba-shi, Ibaraki-ken, Japan (Postal No. 305-8566) as of Dec. 6, 1999, and is also on deposit under the accession number IFO 16338 at the Institute of Fermentation, Osaka (IFO), 2-17-85 Juso-honmachi, Yodogawa-ku, Osaka-shi, Japan as of Nov. 16, 1999.

The transformant *Escherichia coli* DH5α/pTBN6 obtained in Example 5 is on deposit under the accession number FERM BP-7094 at the National Institute of Bioscience and Human Technology (NIBH), Agency of Industrial Science and Technology, Ministry of International Trade and Industry, 1-1-3 Higashi, Tsukuba-shi, Ibaraki-ken, Japan as of Mar. 16, 2000, and is also on deposit under the accession number IFO 16382 at the Institute of Fermentation, Osaka (IFO), 2-17-85 Juso-honmachi, Yodogawa-ku, Osaka-shi, Japan as of Feb. 24, 2000.

EXAMPLES

Working Examples and Experimental Examples are given below to illustrate the invention in further detail, but the present invention is not limited by these examples. Gene manipulation using *Escherichia coli* was managed in accordance with the procedures noted in *Molecular Cloning* by Sambrook et al. as noted above.

Example 1

Cloning of cDNA Coding for Human ATT Precursor Protein (ATTα)

cDNA coding for ATTα was obtained by PCR in the following manner. A 20 µL mixture was prepared, containing 25 pmol each of the oligo DNA represented by SEQ ID NO. 1 as sense strand primer and the oligo DNA represented by SEQ ID NO. 2 as antisense strand primer, 10 µL of Premix Tagq™ (Ex Taq™ Version) (by Takara Shuzo) as template DNA, and 1 µL cDNA solution per tissue from human fetal multiple tissue cDNA panels (Clontech). A thermal cycler (GeneAmp (registered trademark) PCR system model 9700 (Perkin Elmer)) was used to run PCR by a program consisting of 1 minute at 94° C., followed by 5 cycles alternating between 10 seconds at 94° C. and 3 minutes at 72° C., 5 cycles alternating between 10 seconds at 94° C. and 3 minutes at 70° C., and 25 cycles alternating between 10 seconds at 94° C. and 3 minutes at 68° C., and then extension for 5 minutes at 68° C. The reaction liquid was electrophoresed on 2.0% agarose gel, and subsequent ethidium bromide staining revealed a band corresponding to DNA amplified by PCR around the 0.4 kb position, as determined on the basis of the molecular marker in a reaction system using human fetal skeletal muscle cDNA as template DNA. A QIAquick Gel Extraction kit (Qiagen) was used to collect the DNA fragments, pCR (registered trademark) 2.1-TOPO (Invitrogen) was used to sequence the base sequence for TA cloning, and the above plasmid was introduced into *E. coli* DH5α competent cells. Clones with plasmids having the exogenous DNA were selected from clones of ampicillin resistant transformants appearing on LB agar medium containing ampicillin, and pTBN1 plasmid DNA was prepared.

To sequence the base sequence of the DNA insert, the pTBN1 was used as template DNA, and two types (PRM-007 and PRM-008) of commercially available primer DNA (Toyo Boseki) were used as sequence primers. The sequencing reaction was run with the aid of an ABI Prism (registered trademark) BigDye Terminator Cycle Sequencing FS Ready Reaction Kit (Perkin Elmer) according to the conditions in the accompanying protocol, and with the use of the thermal cycler (GeneAmp (registered trademark) PCR system model 9700 (Perkin Elmer)), and the reaction material was analyzed with a DNA Sequencer ABI Prism (registered trademark) 377 (Perkin Elmer).

The pTBN1 contained a 373 base pair DNA fragment represented by SEQ ID NO. 5, which contained an open reading frame consisting of the base sequence of 204 bases represented by SEQ ID NO. 4, coding for a novel polypeptide consisting of the 68 amino acids represented by SEQ ID NO. 3 having no homology with any known proteins (FIG. 1). Sequences present in the encoded polypeptide included a typical 16 amino acid residue secretion signal represented by SEQ ID NO. 6, and a consensus sequence (Gly-Lys-Arg) which had undergone carboxyl terminal amidation by carboxypeptidase and restriction cleavage by a processing enzyme (endoprotease) from the amino acid residue at position 62 to that at position 64. In vivo, this restriction cleavage results in the production of the mature 45 amino acid residue peptide having the amidated carboxyl terminal sequence represented by SEQ ID NO. 7, for example. Although this peptide had the amidated carboxyl terminal sequence Phe-Xaa-Gly-Leu-Met-$NH_2$ motif found in tachykinins, the primary structure of the amino terminal side was completely different from known tachykinins, and it was therefore designated ATT (atypical tachykinin). The precursor ATTα represented by SEQ ID NO. 3 was referred to as ATTα.

The transformant *E. coli* DH5α/pTBN1 was obtained when the plasmid pTBN1 with the DNA coding for the ATTα precursor of the human ATT obtained in this example was introduced into *E. coli* DH5α.

Example 2

Analysis of Full Length cDNA Coding for Human ATT Precursor Protein (ATTβ)

The following is a summary of the analysis of the full length cDNA coding for ATTβ by 5' RACE (rapid amplification of cDNA end) and 3' RACE. The template DNA for the RACE PCR was Marathon™-Ready cDNA human heart (Clontech) or Marathon™-Ready cDNA human fetal lung (Clontech). 5'RACE was run using the oligo DNA represented by SEQ ID NO. 8 as the antisense strand primer, and 3' RACE was run using the oligo DNA represented by SEQ ID NO. 9 as the sense strand primer during the primary PCR reaction based on the DNA sequence coding for ATTα; then, during nested PCR, 5' RACE was run using the oligo DNA represented by SEQ ID NO. 10 as the antisense strand primer, and 3' RACE was run using the oligo DNA represented by SEQ ID NO. 11 as the sense strand primer, giving the 5' upstream sequence and 3' downstream sequence, with the nested primers as starting points. Sequencing of the base sequences of the resulting double-stranded DNA revealed that both sequences of the 5' upstream and 3' downstream sides were the same regardless of the template DNA used. The full length 720 base pairs represented by SEQ ID NO. 12, including the poly(A)$^+$ chain, were thus assumed to be the base sequence of the full length cDNA of the ATT precursor protein. The base sequence of this DNA includes an open reading frame, consisting of the 228 bases represented by SEQ ID NO. 14, coding for the novel polypeptide consisting of the 76 amino acids represented by SEQ ID NO. 13, with no homology to any known proteins (FIG. 2). The encoded polypeptide shared the sequence from the amino acid terminal to the Gly at position 67 in common with the ATTα obtained in Example 1. This protein was designated ATTβ because it had a precursor structure producing the mature peptide ATT in the body in the same manner as ATTα. PCR cloning was done in the same manner as in Example 1 to obtain the actual cDNA fragment coding for ATTβ. Specifically, a 25 µL mixture was prepared, containing 25 pmol each of the oligo DNA represented by SEQ ID NO. 1 as sense strand primer and the oligo DNA represented by SEQ ID NO. 15 as antisense strand primer, 12.5 µL of Premix Taq™ (Ex Taq™ Version) (by Takara Shuzo) as template DNA, and 1 µL cDNA solution per tissue from human fetal multiple tissue cDNA panels (Clontech). A thermal cycler (GeneAmp (registered trademark) PCR system model 9700 (Perkin Elmer)) was used to run PCR by a program consisting of 3 minutes at 94° C., followed by 5 cycles alternating between 10 seconds at 94° C. and 3 minutes at 72° C., 5 cycles alternating between 10 seconds at 94° C. and 3 minutes at 70° C., and 25 cycles alternating between 10 seconds at 94° C. and 3 minutes at 68° C., and then extension for 5 minutes at 68° C. pTBN2 plasmid DNA was obtained upon the same TA cloning procedure as in Example 1 for PCR products of a reaction system using template DNA comprising human fetal heart cDNA, where a DNA band had been detected from around the 0.4 kb to 0.5 kb positions, as determined on the basis of the molecular marker, upon 2.0% agarose gel electrophoresis of the reaction liquid and subsequent ethidium bromide staining. Sequencing of the base sequence of the DNA insert in the pTBN2 in the same manner as in Example 1 revealed the predicted 469 base pair DNA fragment represented by SEQ ID NO. 16, which included the base sequence represented by SEQ ID NO. 14 coding for ATTβ. cDNA fragments sharing the sequence coding for ATTβ were amplified from human heart or human fetal skeletal muscle as well as human fetal lung cDNA by PCR under the same conditions. In PCR tests intended to amplify partial cDNA fragments of the coding region of ATTβ, the DNA was amplified when using human adipose tissue and human pituitary cDNA as template.

cDNA was thus found to code for both ATTα and ATTβ, which are precursors of the aforementioned ATT peptide, and comparison of the base sequences indicated they were splice variants from the same gene.

The plasmid pTBN2 with DNA coding for the human ATT precursor protein ATTβ obtained in the example was introduced into E. coli DH5α, giving the transformant E. coli DH5α/pTBN2.

Example 3

Preparation of Thr-Gly-Lys-Ala-Ser-Gln-Phe-Phe-Gly-Leu-Met-NH$_2$

ATT was synthesized according to the following procedure (amidated carboxyl group of the C terminal methionine in SEQ ID NO. 17, referred to as "ATT(35-45)").

A 0.5 mmol portion of commercially available p-methyl BHA resin (0.57 mmole/g-resin) was introduced into the reaction tank of an ABI 430A peptide synthesizer, and Boc-Met, Boc-Leu, Boc-Gly, Boc-Phe, Boc-Phe, Boc-Gln, Boc-Ser(Bzl), Boc-Ala, Boc-Lys(Cl-Z), Boc-Gly, and Boc-Thr(Bzl) were introduced, in that sequence, by Boc-strategy (NMP-HOBt) peptide synthesis, giving a protected peptide resin. 0.14 g of this resin was stirred for 60 minutes at 0° C. along with 1.5 mL p-cresol in 10 mL anhydrous hydrogen fluoride, the hydrogen fluoride was then distilled off at reduced pressure, diethyl ether was added to the residue for filtration, and the residue was extracted with aqueous acetic acid. The extract was thoroughly concentrated, loaded on a Sephadex (registered trademark) G-25 column (2.0×80 cm) packed with 50% aqueous acetic acid, and eluted with the same solvent to collect the primary fractions, which were loaded on a reverse phase chromatogram (2.6×8.0 cm) packed with LiChroprep (registered trademark) RP-18, washed with 200 mL of 0.1% aqueous TFA, and eluted with a linear gradient using 300 mL of 10% aqueous acetonitrile containing 0.1% TFA and 300 mL of 40% aqueous acetonitrile containing 0.1% TFA, and the primary fractions were collected and lyophilized, giving 26 mg white powder.

Mass analysis $(M+H)^+$ 1185.6 (theoretical 1185.6); HPLC elution time: 17.3 min;
Column Conditions
column: Wakosil 5C18T 4.6×100 mm
eluant: Liquid A: 0.1% aqueous TFA and Liquid B: acetonitrile containing 0.1% TFA used for elution (25 min) with a linear gradient A/B: 95/5 to 45/55
flow rate: 1.0 mL/min Example 4

Thr-Val-Ala-Gly-Asp-Gly-Gly-Glu-Glu-Gln-Thr-Leu-Ser-Thr-Glu-Ala-Glu-Thr-Trp-Glu-Gly-Ala-Gly-Pro-Ser-Ile-Gln-Leu-Gln-Leu-Gln-Glu-Val -Lys-Thr-Gly-Lys-Ala-Ser-Gln-Phe-Phe-Gly-Leu-Met-NH$_2$

ATT was synthesized according to the following procedure (amidated carboxyl group of the C terminal methionine in SEQ ID NO. 7, referred to as "ATT(1-45)").

Protected peptide resin with the amino acid sequence of ATT(1-45) was obtained by further adding Boc amino acids according to the desired sequence to the amino terminal side of the protected peptide resin prepared up to Boc-Thr(Blz) in Example 1. This resin was treated with hydrogen fluoride and purified by column chromatography in the same manner as in Example 1 to obtain ATT(1-45).

Mass analysis $(M+H)^+$ 4727.6 (theoretical 4728.2); HPLC elution time: 20.4 min.
Column Conditions
column: Wakosil 5C18T 4.6×100 mm
eluant: Liquid A: 0.1% aqueous TFA and Liquid B: acetonitrile containing 0.1% TFA used for elution with a linear gradient (25 min) A/B: 95/5 to 45/55
flow rate: 1.0 mL/min Example 5

3'-RACE Analysis Using Human Fetal Skeletal Muscle cDNA

After Example 2, 3'-RACE analysis was performed using human fetal skeletal muscle cDNA. Marathon™-Ready cDNA human fetal skeletal muscle (Clontech) was used as the template DNA for RACE PCR. The reaction was carried out in the same manner as in Example 2 using the oligo DNA represented by SEQ ID NO. 9 as the sense strand primer in primary PCR and then the oligo DNA represented by SEQ ID NO. 11 as the sense strand primer in nested PCR. The reaction liquid was electrophoresed on 2.0% agarose gel, and ethidium bromide staining revealed other RACE PCR products of a size greater than that of the DNA fragment of a length corresponding to the reaction product obtained in Example 2. The PCR products were collected in the same manner as in Example 1 and TA cloned, and plasmids were then introduced into E. coli DH5α competent cells. Several clones with plasmids having the exogenous DNA fragments incorporated therein were selected from clones of ampicillin resistant transformants appearing on LB agar medium containing ampicillin, plasmid DNA was prepared, and the base sequences of the inserted DNA fragments were sequenced. Plasmid pTBN6 corresponding to clone #21 was found to include the 539 bases represented by SEQ ID NO. 18, starting at the nested primer represented by SEQ ID NO. 11, as well as a DNA fragment with the polyA sequence added to the 3' side. Comparison of this base sequence with that of the 3'-RACE PCR product obtained in Example 2 revealed that this base sequence included the 93 base insert sequence represented by SEQ ID NO. 19, but the two base sequences were otherwise completely consistent with each other except for the length of the 3' end polyA sequence. In conjunction with the results of Example 2, it was thus concluded that the gene for the ATT precursor protein included a novel splice variant producing the base sequence represented by SEQ ID NO. 21 coding for a novel polypeptide (ATT#21F) consisting of the 107 amino acids represented by SEQ ID NO. 20. This novel polypeptide not only had the precursor structure producing a peptide similar to the mature peptide ATT produced by ATTα and ATTβ above, but the carboxyl terminal side also included a consensus sequence (Gly-Lys-Arg) which had undergone carboxyl terminal amidation by carboxypeptidase and restriction cleavage by a processing enzyme (endopeptidase) from the amino acid residue at position 90 to that at position 92 in SEQ ID NO. 20, and the sequence from positions 74 to 77 of SEQ ID NO. 20 (Arg-Arg-Lys-Lys) was also a restriction cleavage motif resulting from a processing enzyme (endoprotease). In vivo, this restriction cleavage results in the production of a novel sequence of 14 amino acid residues with the amidated carboxyl terminal sequence represented by SEQ ID NO. 22. The amidated carboxyl terminal motif of the peptide is Phe-Xaa-Gly-Leu-Leu-NH$_2$. One terminal amino acid (Leu/Met) is different from the Phe-Xaa-Gly-Leu-Met-NH$_2$ motif of conventional tachykinin family. This structure has not been found in any known naturally occurring proteins or peptides.

The pTBN6 plasmid analyzed in this example was introduced into E. coli DH5α, giving the transformant E. coli DH5α/pTBN6.

Example 6

Chromosome Mapping of Gene Coding for Human ATT Precursor Proteins

Radiation Hybrid analysis was employed in the following manner for chromosomal mapping of the gene coding for human ATT precursor proteins. PCR using the oligo DNA represented by SEQ ID NO. 11 as the sense strand primer, the oligo DNA represented by SEQ ID NO. 2 as the antisense strand primer, and human chromosomal DNA as template resulted in the specific amplification of the 160 base pair DNA fragment represented by SEQ ID NO. 52, corresponding to a portion of the base sequence of the ATTα above. PCR was carried out with the same combination of primers for a total of 83 DNA clones in Stanford G3 Radiation Hybrid Panels (Research Genetics), the reaction solutions were electrophoresed on 2% agarose gel, and the gels were stained with ethidium bromide to check for the presence or absence of amplified PCR reaction products of the same size as above. The resulting patterns which appeared for the amplified products of each clone were sent to the SHGC RH Server at the Stanford Human Genome Center to search for markers. Based on the resulting information, such as SHGC-52587, SHGC-2255, and SHGC-828 which showed up as hits in terms of neighboring markers, the locus of the gene coding for the polypeptide of the invention was mapped to the long arm (17q21) of human chromosome 17.

Example 7

Preparation of Lys-Lys-Ala-Tyr-Gln-Leu-Glu-His-Thr-Phe-Gln-Gly-Leu-Leu-NH$_2$ (SEQ ID NO: 22)

The following procedure was used to synthesize the polypeptide represented by SEQ ID NO. 22 obtained in Example 5, in which the carboxyl group of the C terminal leucine was amidated.

A 0.5 mmole portion of commercially available p-methyl BHA resin (0.57 mmole/g-resin) was introduced into the reaction tank of an ABI 430A peptide synthesizer, and Boc-Leu, Boc-Leu, Boc-Gly, Boc-Gln, Boc-Phe, Boc-Thr (Bzl), Boc-His(Bom), Boc-Glu(OcHex), Boc-Leu, Boc-Gln, Boc-Tyr(Br-z), Boc-Ala, Boc-Lys(Cl-z), Boc-Lys(Cl-Z) were introduced, in that sequence, by Boc-strategy (NMP-HOBt) peptide synthesis, giving a protected peptide resin. The resin was stirred for 60 minutes at 0° C. along with p-cresol in anhydrous hydrogen fluoride, and the hydrogen fluoride was then distilled off at reduced pressure. Diethyl ether was added to the residue for filtration, the residue was extracted with aqueous acetic acid, the extract was thoroughly concentrated, loaded on a Sephadex™ G-25 column (2.0×80 cm) packed with 50% aqueous acetic acid, and eluted with the same solvent to collect the primary fractions, which were lyophilized. These were dissolved in 0.1% TFA aqueous solution and loaded on a reverse phase chromatogram (2.6×8.0 cm) packed with LiChroprep™ RP-18, washed with 200 mL of 0.1% aqueous TFA, and eluted with a linear gradient using 300 mL of 10% aqueous acetonitrile containing 0.1% TFA and 300 mL of 40% aqueous acetonitrile containing 0.1% TFA, and the primary fractions were collected and lyophilized, giving a white powder.

Mass analysis (M+H)$^+$ 1674.9 theoretical 1674.9; HPLC elution time: 17.0 min.

Column Conditions column: Wakosil 5C18T 4.6×100 mm eluant: Liquid A: 0.1% aqueous TFA and Liquid B: acetonitrile containing 0.1% TFA used for elution (25 min) with a linear gradient A/B: 95/5 to 45/55 flow rate: 1.0 mL/min

Example 8

Preparation of Lys-Ala-Tyr-Gln-Leu-Glu-His-Thr-Phe-Gln-Gly-Leu-Leu-NH$_2$ (Amide of Peptide Consisting of Amino Acid Sequence Represented by SEQ ID NO. 23)

The target white powder was obtained when resin was purified in the same manner as in Example 7 before the introduction of the final Boc-Lys(Cl-Z) in Example 7.

Mass analysis (M+H)$^+$ theoretical 1546.8.

Example 9

Preparation of Ala-Tyr-Gln-Leu-Glu-His-Thr-Phe-Gln-Gly-Leu-Leu-NH$_2$ (Amide of Peptide Consisting of Amino Acid Sequence Represented by SEQ ID NO. 24)

The target white powder was obtained when resin was purified in the same manner as in Example 8 up to the introduction of the Boc-Ala in Example 7.

Mass analysis (M+H)$^+$ theoretical 1418.7.

Example 10

Preparation of Tyr-Gln-Leu-Glu-His-Thr-Phe-Gln-Gly-Leu-Leu-NH$_2$ (Amide of Peptide Consisting of Amino Acid Sequence Represented by SEQ ID NO. 25)

The target white powder was obtained when resin was purified in the same manner as in Example 8 up to the introduction of the Boc-Tyr(Br-Z) in Example 7.

Mass analysis (M+H)$^+$ theoretical 1347.7.

Example 11

Preparation of Gln-Leu-Glu-His-Thr-Phe-Gln-Gly-Leu-Leu-NH$_2$ (Amide of Peptide Consisting of Amino Acid Sequence Represented by SEQ ID NO. 26)

The target white powder was obtained when resin was purified in the same manner as in Example 8 before the introduction of the Boc-Tyr(Br-Z) in Example 7.

Mass analysis (M+H)$^+$ theoretical 1184.6; HPLC elution time: 16.3 min.

Column Conditions column: Wakosil 5C18T 4.6×100 mm eluant: Liquid A: 0.1% aqueous TFA and Liquid B: acetonitrile containing 0.1% TFA used for elution (25 min) with a linear gradient A/B: 95/5 to 45/55 flow rate: 1.0 mL/min

Example 12

Preparation of pGlu-Leu-Glu-His-Thr-Phe-Gln-Gly-Leu-Leu-NH$_2$ (Amide of Peptide Consisting of Amino Acid Sequence Represented by SEQ ID NO. 27)

The target white powder was obtained when the same resin used in Example 11 was treated with anhydrous hydrogen fluoride and then set aside for 20 hours at a pH of 7.5, the conversion of the N terminal Gln to pGlu was checked by HPLC, and the product was purified, giving the target white powder.

Mass analysis (M+H)$^+$ theoretical 1167.6; HPLC elution time: 18.1 min.

Column Conditions column: Wakosil 5C18T 4.6×100 mm eluant: Liquid A: 0.1% aqueous TFA and Liquid B: acetonitrile containing 0.1% TFA used for elution (25 min) with a linear gradient A/B: 95/5 to 45/55 flow rate: 1.0 mL/min

Example 13

Preparation of Arg-Lys-Lys-Ala-Tyr-Gln-Leu-Glu-His-Thr-Phe-Gln-Gly-Leu-Leu-NH$_2$ (Amide of Peptide Consisting of Amino Acid Sequence Represented by SEQ ID NO. 28)

The target white powder was obtained when resin was purified in the same manner as in Example 7 after Boc-Arg (Tos) had also been introduced into the protected peptide resin prepared in Example 7.

Mass analysis (M+H)$^+$ theoretical 1831.0.

Experimental Example 1

Activity of ATT(35-45) (Polypeptide C Terminal Amide Consisting of Amino Acid Sequence Represented by SEQ ID NO. 17) on Blood Pressure in Anesthetized Rats The activity of ATT(35-45) on blood pressure in anesthetized rats was determined in the following manner. Male Wistar rats (weighing 300 to 400 g, by CLEA Japan Inc.) were anesthetized with thiobutabarbital sodium (100 mg/kg i.p.), a catheter (SP-55) for measuring blood pressure connected to a transducer was inserted into the left carotid artery, and a catheter (SP-35) for intravenous administration was inserted into the left femoral vein. The peptide was dissolved in physiological saline containing 0.05% BSA, and doses of 0.01, 0.1, and 1 nmol/kg were administered through the left femoral vein. The blood pressure was continuously recorded on a polygraph (NEC Sanei).

Results: The administration of ATT(35-45) in doses of 0.01, 0.1, and 1 nmol/kg resulted in dose-dependent decreases in blood pressure in the anesthetized rats. The decrease in blood pressure by dose was 12.3±0.8 mmHg (n=4), 21.5±1.8 mmHg (n=4), and 33.8±6.6 mmHg (n=4), respectively (mean±standard deviation).

Experimental Example 2

Contracting Activity of ATT(35-45) on Ginea Pig Ileum Specimens

The contracting activity of ATT(35-45) on guinea pig ileum specimens was determined in the following manner. 13 to 15-week old male guinea pigs (std: Hartley) were exsanguinated, and the ileum was excised. The ileum was cut to a length of 1.5 cm to prepare specimens. The specimens were aerated with a gas mixture (95% O$^2$-5% CO$_2$) while suspended in Tyrode's solution (137.9 mM NaCl, 2.7 mM KCl, 1.8 mM CaCl$_2$, 0.5 mM MgCl$_2$, 1.1 mM NaH$_2$PO$_4$, 11.9 mM NaHCO$_3$, and 5.6 mM glucose) maintained at 37° C., and the isotonic contractions under a 0.5 g load were recorded. The peptide was administered cumulatively in the organ bath.

Results: The administration of $10^{-10}$ M to $3\times10^{-7}$ M ATT(35-45) resulted in concentration-dependent contraction of the guinea pig ileum specimens. The maximum concentration was about 90% of the contraction induced with $10^{-6}$ M acetylcholine. The EC$_{50}$ of the ATT(35-45) was 3.5 nM (n=6) (FIG. 3).

Example 14

Construction of Expression Vector

DNA fragments coding for the human ATT precursor protein (ATTβ) obtained in Example 2 were obtained by PCR in the following manner. That is, a 50 µL mixture was prepared, containing 20 pmol each of the synthetic oligo DNA represented by SEQ ID NO. 53 as the sense strand primer and the synthetic oligo DNA represented by SEQ ID NO. 54 as the antisense strand primer, 5 µL of 10× Advantage (registered trademark) 2×PCR buffer (Clontech), 1 µL 50×dNTP mix (Clontech), 1 µL of 50× Advantage 2 Polymerase Mix (Clontech), and 1 ng of the pTBN2 plasmid obtained in Example 2 as the template DNA. A thermal cycler (GeneAmp (registered trademark) PCR system model 9700 (Applied Biosystems) was used to run PCR by a program consisting of 1 minute at 95° C., followed by 25 cycles alternating between 10 seconds at 95° C. and 1 minute at 74° C., and then extension for 7 minutes at 74° C. The resulting 0.25 kb fragments were subcloned to the pCR2.1-TOPO (Invitrogen) vector, and the plasmid was introduced to *E. coli* JM109 (Takara Shuzo) competent cells. Clones with the plasmid having the exogenous DNA fragment incorporated therein were selected from colonies of ampicillin resistant transformants which appeared on LB agar medium containing ampicillin to prepare pCR2.1-TOPO/ATTβ plasmid DNA. The plasmid was double digested with the restriction enzymes EcoRI and SalI (Takara Shuzo). Then, 0.25 kb gene fragments containing the ATTβ were separated and collected by electrophoresis on agarose gel, and were purified using a QIAquick Gel Extraction kit (Qiagen). The resulting fragments were subcloned to the pCAN618 vector, and the plasmid was introduced into *E. coli* JM109 (Takara Shuzo) competent cells. Clones with the plasmid having the exogenous DNA fragment incorporated therein were selected from colonies of ampicillin resistant transformants which appeared on LB agar medium containing ampicillin to prepare pCAN-ATTβ plasmid DNA. The pCAN-ATTβ contained the 250 base pair DNA fragment represented by SEQ ID NO. 55 coding for human ATTβ consisting of the 76 amino acids represented by SEQ ID NO. 13.

The DNA fragment coding for human ATT#21F determined in Example 5 was obtained by PCR in the following manner. That is, a 50 µL mixture was prepared, containing 20 pmol each of the synthetic oligo DNA represented by SEQ ID NO. 56 as the sense strand primer and the synthetic oligo DNA represented by SEQ ID NO. 57 as the antisense strand primer, 5 µL of 10×Advantage (registered trademark) 2×PCR buffer (Clontech), 1 µL 50×dNTP mix (Clontech), 1 µL of 50× Advantage 2 Polymerase Mix (Clontech), and 5 µL DNA solution containing the sequence coding for human ATT#21F represented by SEQ ID NO. 21 as the template DNA. A thermal cycler (GeneAmp (registered trademark) PCR system model 9700 (Applied Biosystems) was used to run PCR by a program consisting of 1 minute at 95° C., followed by 20 cycles alternating between 5 seconds at 95° C. and 10 seconds at 68° C., and then extension for 1 minute at 68° C. The reaction solution was double digested with the restriction enzymes EcoRI and SalI (Takara Shuzo), and the short DNA fragments produced by digestion with the restriction enzymes and unreacted primers were removed using a QIAquick PCR Purification kit (Qiagen). The resulting 0.34 kb fragments were subcloned to the pCAN618 vector, and the plasmid was introduced into *E. coli* Epicurian Coli (registered trademark) XL10-Gold (registered trademark) line (Stratagene) competent cells. Clones with the plasmid having the exogenous DNA fragment incorporated therein were selected from colonies of ampicillin resistant transformants which appeared on LB agar medium containing ampicillin to prepare pCAN-ATT#21F plasmid DNA. The pCAN-ATT#21F contained a 340 base pair DNA fragment represented by SEQ ID NO. 58 coding for human ATT#21F consisting of the 107 amino acids represented by SEQ ID NO. 20.

A human PPT-A (substance P/neurokinin A precursor) expression vector was prepared in the following manner for use in a comparative test. Human PPT-A cDNA fragments were first isolated. That is, a 50 µL mixture was prepared, containing 20 pmol each of the synthetic oligo DNA represented by SEQ ID NO. 59 as the sense strand primer and the synthetic oligo DNA represented by SEQ ID NO. 60 as the antisense strand primer, 5 µL of 10× Advantage (registered trademark) 2×PCR buffer (Clontech), 1 µL 50×dNTP mix (Clontech), 1 µL of 50× Advantage 2 Polymerase Mix (Clontech), and 5 µL Human MTC panel Brain solution as the template DNA. A thermal cycler (GeneAmp (registered trademark) PCR system model 9700 (Applied Biosystems) was used to run PCR by a program consisting of 1 minute at 96° C., followed by 25 cycles alternating between 10 seconds at 96° C., 5 seconds at 54° C., and 30 seconds at 72° C., and then extension for 2 minutes at 72° C. The unreacted primers were removed from the reaction solution using a QIAquick PCR Purification kit (Qiagen). The resulting DNA fragments were subcloned to the pCR2.1-TOPO (Invitrogen) vector, and the plasmid was introduced into *E. coli* Epicurian Coli (registered trademark) XL10-Gold (registered trademark) line (Stratagene) competent cells. Clones with the plasmid having the exogenous DNA fragment incorporated therein were selected from colonies of ampicillin resistant transformants which appeared on LB agar medium containing ampicillin to prepare pCR2.1-TOPO/PPT-A plasmid DNA.

The DNA fragment coding for human PPT-A was then obtained by PCR in the following manner. That is, a 50 µL mixture was prepared, containing 20 pmol each of the synthetic oligo DNA represented by SEQ ID NO. 61 as the sense strand primer and the synthetic oligo DNA represented by SEQ ID NO. 62 as the antisense strand primer, 5 µL of 10× Advantage (registered trademark) 2×PCR buffer (Clontech), 1 µL 50×dNTP mix (Clontech), 1 µL of 50× Advantage 2 Polymerase Mix (Clontech), and 1 ng pCR2.1-TOPO/PPT-A plasmid as the template DNA. A thermal cycler (GeneAmp (registered trademark) PCR system model 9700 (Applied Biosystems) was used to run PCR by a program consisting of 1 minute at 96° C., followed by 20 cycles alternating between 5 seconds at 96° C., 5 seconds at 66° C., and 30 seconds at 72° C., and then extension for 1 minute at 72° C. The reaction solution was double digested with the restriction enzymes EcoRI and SalI (Takara Shuzo), and the short DNA fragments produced by digestion with the restriction enzymes and unreacted primers were removed using a QIAquick PCR Purification kit (Qiagen). The resulting 0.4 kb fragments were subcloned to the pCAN618 vector, and the plasmid was introduced into *E. coli* Epicurian Coli (registered trademark) XL10-Gold (registered trademark) line (Stratagene) competent cells. Clones with the plasmid having the exogenous DNA fragment incorporated therein were selected from colonies of ampicillin resistant transformants which appeared on LB agar medium containing ampicillin to prepare PCAN-PPTA plasmid DNA. The PCAN-PPTA contained a 409 base pair DNA fragment represented by SEQ ID NO. 64 coding for human PPT-A consisting of the 129 amino acids represented by SEQ ID NO. 63.

Example 15

Introduction of Expression Vector to AtT-20 Cells and Secretion of Gene Product

To check the biosynthesis of the peptide from the ATT polypeptide precursors, mouse pituitary AtT-20 cells were used to express the ATT polypeptide precursors, and the following method was used to determine whether or not the polypeptide was secreted in culture media. Petri dishes 6 cm in diameter were inoculated with AtT-20 cells in a proportion of $2.5 \times 10^6$ cells/dish on the day before transfection of the expression vector, and were incubated for 24 hours in $CO_2$ in DMEM medium supplemented with 10% FBS (JRH) (by GibcoBRL). The pCAN-ATTβ, pCAN-ATT#21F, and pCAN-PPTA vectors expressing ATTβ, ATT#21F, and PPT-A, respectively, were transfected using Effectene (Qiagen) in a proportion of 1 μg/dish, respectively. After 24 hours, the medium was replaced with selection medium containing 500 μg/mL Geneticin. The medium was replaced about every 5 days during 3 weeks of continuous culture, giving transformants. After continued culture on selection medium, the cells were replaced with serum-free medium, and the culture supernatant was recovered after another 2 days. The polypeptide in the resulting supernatant was detected using a commercially available EIA kit, Substance P Enzyme Immunoassay Kit (Cayman Cat #583751). It was previously ascertained that the peptides obtained in Examples 3 and 4 could be detected with the same degree of high sensitivity as Substance P when using the Substance P Enzyme Immunoassay Kit. The Substance P Enzyme Immunoassay Kit detected the secretion of peptides in the culture supernatant of AtT-20 cells having expression vectors pCAN-ATTβ, pCAN-ATT#21F, and pCAN-PPTA. The biosynthesis of the peptide through processing from ATT polypeptide precursors was thus confirmed.

Example 16

Preparation of Immunogen Containing Peptide Represented by SEQ ID NO. 22 in Example 5, and Immunization Conjugates of hemocyanin (KLH) and the novel peptide obtained in Example 7 were prepared for use as immunogen. That is, 10 mg KLH and 4.5 mg of the aforementioned peptide were dissolved and mixed in phosphate buffer (pH 6.5); glutaraldehyde was added; and a reaction was conducted for 1 hour at ambient temperature. Following the reaction, the product was dialyzed for 2 days at 4° C. against PBS, and the glutaraldehyde-free product was used as immunogen (antigen protein).

For primary immunization, the antigen protein was subcutaneously administered to rabbits (Japanese White) in an amount of 1 mg per animal in the form of an emulsion with FCA (Freund's Complete Adjuvant). Boosters were given every 2 weeks for a total of 4 times. For the second and subsequent times, the dosage of antigen protein was 0.5 mg per animal, given by subcutaneous injection in the form of an emulsion with FICA (Freund's Incomplete Adjuvant). One week following the final booster, blood was drawn from the auricular vein, and serum fractions were obtained in the usual manner.

Example 17

Preparation of Western Horseradish Peroxidase (HRP) Labeled Peptide

The novel peptide obtained in Example 7 was cross-linked with HRP (for enzyme immunoassay, by Boehringer Mannheim) to produce labels for enzyme immunoassay (EIA). That is, 8 mg HRP was dissolved in 0.95 mL of 0.02 M phosphate buffer (pH 6.8), which was mixed with 0.05 mL DMF solution containing 30-fold (molar) SPDP relative to the HRP, a reaction was brought about for 60 minutes at ambient temperature, 0.3 mL of 0.1 M acetic acid buffer (pH 4.5) containing 40 mM DTT was then added, and a reaction was brought about for another 30 minutes at ambient temperature. Fractions were obtained on a Sephadex G-25 column equilibrated with 0.1 M phosphate buffer (pH 6.0) containing 2 mM EDTA, giving HRP with SH groups.

1.5 mg of the aforementioned peptide was meanwhile dissolved in 0.5 mL of 0.1 M phosphate buffer (pH 6.8) and mixed with 0.05 mL of DMF solution containing GMBS in an equimolar amount relative to the peptide. A reaction was conducted for 60 minutes at ambient temperature, and fractions were then obtained on a Sephadex G-25 column equilibrated with 0.1 M phosphate buffer (pH 6.8), giving peptides having maleimide groups incorporated therein.

The HRP having the SH groups and the peptide having the maleimide groups were then mixed in a molar ratio of 1:3 and allowed to react overnight at 4° C., and fractions were obtained on an Ultrogel AcA44 column equilibrated with 0.1 M phosphate buffer (pH 6.5), giving HRP-labeled peptides. The resulting labeled peptides were suitable as labels for enzyme immunoassay (EIA).

INDUSTRIAL APPLICABILITY

The present invention provides novel tachykinin polypeptides (referred to as ATT, ATT polypeptides, ATTshort1, or ATTshort2), their precursors (designated ATTα, ATTβ, or ATT#21F), and polynucleotides coding for them. The invention also provides recombinant vectors containing such polynucleotides, transformants containing such vectors, and transgenic animals having genes containing such polynucleotides. The invention furthermore provides methods for producing such polypeptides, antibodies against such polypeptides, agonists and antagonists, and methods for identifying them. The invention additionally provides pharmaceutical compositions comprising such polypeptides, polynucleotides, antagonists, antibodies, and receptors, and methods for treating or preventing disease.

What is claimed is:

1. An isolated polypeptide, or amide or ester, or salts thereof, wherein the polypeptide comprises the amino acid sequence of SEQ ID NO: 17.

2. The amide or salt thereof, of the polypeptide of claim 1.

3. An isolated polypeptide according to claim 1, wherein the C terminal carboxyl group is amidated.

4. A kit comprising the polypeptide, or amide or ester, or salts thereof, according to claim 1.

5. A pharmaceutical composition comprising the polypeptide, or amide or ester thereof, or salts thereof, according to claim 1, and a pharmaceutically acceptable carrier, excipient or diluent.

6. A method of making a pharmaceutical composition comprising adding a pharmaceutically acceptable carrier, excipient or diluent to the polypeptide of claim 1.

7. A method for treating hypertension, said method comprising administering the polypeptide or amide or ester thereof, or their salts according to claim 1 to mammals in need thereof.

* * * * *

SEQUENCE LISTING

<160> NUMBER OF SEQ ID NOS: 64

<210> SEQ ID NO 1

```
<211> LENGTH: 29
<212> TYPE: DNA
<213> ORGANISM: Artificial Sequence
<220> FEATURE:
<223> OTHER INFORMATION: Designed oligonucleotide primer to amplify ATT
      alpha or ATT beta cDNA fragment

<400> SEQUENCE: 1
tcaaggagcc aaagagcaaa ccaaagcct                                         29

<210> SEQ ID NO 2
<211> LENGTH: 32
<212> TYPE: DNA
<213> ORGANISM: Artificial Sequence
<220> FEATURE:
<223> OTHER INFORMATION: Designed oligonucleotide primer to amplify ATT
      alpha cDNA fragment

<400> SEQUENCE: 2
ggctttgact tagggcctct gctttatgtt gc                                     32

<210> SEQ ID NO 3
<211> LENGTH: 68
<212> TYPE: PRT
<213> ORGANISM: human

<400> SEQUENCE: 3

Met Leu Pro Cys Leu Ala Leu Leu Leu Met Glu Leu Ser Val Cys
  1               5                  10                  15

Thr Val Ala Gly Asp Gly Gly Glu Gln Thr Leu Ser Thr Glu Ala
                 20                  25                  30

Glu Thr Trp Glu Gly Ala Gly Pro Ser Ile Gln Leu Gln Leu Gln Glu
             35                  40                  45

Val Lys Thr Gly Lys Ala Ser Gln Phe Phe Gly Leu Met Gly Lys Arg
     50                  55                  60

Val Gly Gly Glu
 65

<210> SEQ ID NO 4
<211> LENGTH: 204
<212> TYPE: DNA
<213> ORGANISM: human

<400> SEQUENCE: 4
atgctgcctt gcctcgccct gcttctcctg atggagctgt ccgtgtgcac tgtggcaggt      60
gatggtggag aggaacagac actcagcact gaagcagaga cctgggaagg cgctggcccc     120
agcattcagc tccagctgca ggaggtgaag acgggcaagg caagccagtt ctttgggctg     180
atggggaagc gagtgggagg tgag                                             204

<210> SEQ ID NO 5
<211> LENGTH: 373
<212> TYPE: DNA
<213> ORGANISM: human

<400> SEQUENCE: 5
tcaaggagcc aaagagcaaa ccaaagcctg caggaggcat cttcaagctg agagggctc       60 ccagagattc aggacagtg caggctcacc atgctgcctt gcctcgccct gcttctcctg      120
atggagctgt ccgtgtgcac tgtggcaggt gatggtggag aggaacagac actcagcact     180
gaagcagaga cctgggaagg cgctggcccc agcattcagc tccagctgca ggaggtgaag     240
acgggcaagg caagccagtt ctttgggctg atggggaagc gagtgggagg tgagtgacaa     300
```

```
tgacaatgga gcccagcaag caggggttct gagtgggttc tgcaacataa agcagaggcc    360
ctaagtcaaa gcc                                                      373
```

<210> SEQ ID NO 6
<211> LENGTH: 16
<212> TYPE: PRT
<213> ORGANISM: human

<400> SEQUENCE: 6

```
Met Leu Pro Cys Leu Ala Leu Leu Leu Met Glu Leu Ser Val Cys
 1               5                  10                  15
```

<210> SEQ ID NO 7
<211> LENGTH: 45
<212> TYPE: PRT
<213> ORGANISM: human

<400> SEQUENCE: 7

```
Thr Val Ala Gly Asp Gly Gly Glu Glu Gln Thr Leu Ser Thr Glu Ala
 1               5                  10                  15

Glu Thr Trp Glu Gly Ala Gly Pro Ser Ile Gln Leu Gln Leu Gln Glu
            20                  25                  30

Val Lys Thr Gly Lys Ala Ser Gln Phe Phe Gly Leu Met
        35                  40                  45
```

<210> SEQ ID NO 8
<211> LENGTH: 27
<212> TYPE: DNA
<213> ORGANISM: Artificial Sequence
<220> FEATURE:
<223> OTHER INFORMATION: Designed oligonucleotide primer to amplify ATT
      beta cDNA fragment

<400> SEQUENCE: 8

```
ccagcgcctt cccaggtctc tgcttca                                        27
```

<210> SEQ ID NO 9
<211> LENGTH: 30
<212> TYPE: DNA
<213> ORGANISM: Artificial Sequence
<220> FEATURE:
<223> OTHER INFORMATION: primer/probe

<400> SEQUENCE: 9

```
gtggcaggtg atggtggaga ggaacagaca                                     30
```

<210> SEQ ID NO 10
<211> LENGTH: 22
<212> TYPE: DNA
<213> ORGANISM: Artificial Sequence
<220> FEATURE:
<223> OTHER INFORMATION: Designed oligonucleotide primer to amplify ATT
      beta cDNA fragment

<400> SEQUENCE: 10

```
tgttcctctc caccatcacc tg                                             22
```

<210> SEQ ID NO 11
<211> LENGTH: 30
<212> TYPE: DNA
<213> ORGANISM: Artificial Sequence
<220> FEATURE:
<223> OTHER INFORMATION: Designed oligonucleotide primer to amplify ATT
      beta cDNA fragment -continued

<400> SEQUENCE: 11
attcagctcc agctgcagga ggtgaagacg                                    30

<210> SEQ ID NO 12
<211> LENGTH: 720
<212> TYPE: DNA
<213> ORGANISM: human

<400> SEQUENCE: 12
cagctggaag gaccagaaaa caggggagt ttcccctatc tacactcaag gagccaaaga    60
gcaaaccaaa gcctgcagga ggcatcttca agctgagagg ggctcccaga gattccagga  120
cagtgcaggc tcaccatgct gccttgcctc gccctgcttc tcctgatgga gctgtccgtg  180
tgcactgtgg caggtgatgg tggagaggaa cagacactca gcactgaagc agagacctgg  240
gaaggcgctg gccccagcat tcagctccag ctgcaggagg tgaagacggg caaggcaagc  300
cagttctttg gctgatggg gaagcgagtg ggaggcagag aggatgaggc ccaaggttca  360
gagtaaaagc ccccaccaca gacttcccag aggacacggt gccgcttctt cctacctgga  420
tgtcacagct gacaagccgg caggccaact ctcttctctg tgtctcctgt cctcatcgct  480
ggcacttcac acaaggccca cactgaaccc actgggcttc ttcctggact ctcagtgtca  540
agcagcagtc ctgcataaat gcacagcttc gccgtagcaa gctgcactga ctctgccctc  600
cctcacactc agagttggca tctcactgca cagcagtgag gagactcgca cactctgtat  660
cctgtgccta gcacacagta ggcactcaat aaatgagtga ccagaaaaaa aaaaaaaaaa  720

<210> SEQ ID NO 13
<211> LENGTH: 76
<212> TYPE: PRT
<213> ORGANISM: human

<400> SEQUENCE: 13

Met Leu Pro Cys Leu Ala Leu Leu Leu Met Glu Leu Ser Val Cys
  1               5                  10                  15

Thr Val Ala Gly Asp Gly Gly Glu Glu Gln Thr Leu Ser Thr Glu Ala
             20                  25                  30

Glu Thr Trp Glu Gly Ala Gly Pro Ser Ile Gln Leu Gln Leu Gln Glu
         35                  40                  45

Val Lys Thr Gly Lys Ala Ser Gln Phe Phe Gly Leu Met Gly Lys Arg
     50                  55                  60

Val Gly Gly Arg Glu Asp Glu Ala Gln Gly Ser Glu
 65                  70                  75

<210> SEQ ID NO 14
<211> LENGTH: 228
<212> TYPE: DNA
<213> ORGANISM: human

<400> SEQUENCE: 14
atgctgcctt gcctcgccct gcttctcctg atggagctgt ccgtgtgcac tgtggcaggt    60
gatggtggag aggaacagac actcagcact gaagcagaga cctggaaggg cgctggcccc   120
agcattcagc tccagctgca ggaggtgaag acgggcaagg caagccagtt ctttgggctg   180
atggggaagc gagtgggagg cagagaggat gaggcccaag gttcagag               228

<210> SEQ ID NO 15
<211> LENGTH: 28
<212> TYPE: DNA
<213> ORGANISM: Artificial Sequence

```
<220> FEATURE:
<223> OTHER INFORMATION: Designed oligonucleotide primer to amplify ATT
      beta cDNA fragment

<400> SEQUENCE: 15 cagtgggttcagtgtgggccttgtgtga                                              28

<210> SEQ ID NO 16
<211> LENGTH: 469
<212> TYPE: DNA
<213> ORGANISM: human

<400> SEQUENCE: 16
tcaaggagcc aaagagcaaa ccaaagcctg caggaggcat cttcaagctg agagggctc         60 ccagagattc caggacagtg caggctcacc atgctgcctt gcctcgccct gcttctcctg       120
atggagctgt ccgtgtgcac tgtggcaggt gatggtggag aggaacagac actcagcact       180
gaagcagaga cctgggaagg cgctggcccc agcattcagc tccagctgca ggaggtgaag       240
acgggcaagg caagccagtt cttgggctg atggggaagc gagtgggagg cagagaggat         300
gaggcccaag gttcagagta aaagccccca ccacagactt cccagaggac acggtgccgc       360
ttcttcctac ctggatgtca cagctgacaa gccggcaggc caactctctt ctctgtgtct       420
cctgtcctca tcgctggcac ttcacacaag gcccacactg aacccactg                   469

<210> SEQ ID NO 17
<211> LENGTH: 11
<212> TYPE: PRT
<213> ORGANISM: human

<400> SEQUENCE: 17

Thr Gly Lys Ala Ser Gln Phe Phe Gly Leu Met
     1               5                  10

<210> SEQ ID NO 18
<211> LENGTH: 539
<212> TYPE: DNA
<213> ORGANISM: human

<400> SEQUENCE: 18
attcagctcc agctgcagga ggtgaagacg ggcaaggcaa gccagttctt tgggctgatg         60
gggaagcgag tgggaggaag acctctgatc cagccaagga gaaaaaagc atatcagctg        120 gaacacacgt tccagggcct cctgggcaag agaagcctgt tcacagaagg cagagaggat       180
gaggcccaag gttcagagta aaagccccca ccacagactt cccagaggac acggtgccgc       240
ttcttcctac ctggatgtca cagctgacaa gccggcaggc caactctctt ctctgtgtct       300
cctgtcctca tcgctggcac ttcacacaag gcccacactg aacccactgg gcttcttcct       360
ggactctcag tgtcaagcag cagtcctgca taaatgcaca gcttcgccgt agcaagctgc       420
actgactctg ccctccctca cactcagagt tggcatctca ctgcacagca gtgaggagac       480
tcgcacactc tgtatcctgt gcctagcaca cagtaggcac tcaataaatg agtgaccag        539

<210> SEQ ID NO 19
<211> LENGTH: 93
<212> TYPE: DNA
<213> ORGANISM: human

<400> SEQUENCE: 19
gaagacctct gatccagcca aggagaaaaa agcatatca gctggaacac acgttccagg         60
gcctcctggg caagagaagc ctgttcacag aag                                    93
```

<210> SEQ ID NO 20
<211> LENGTH: 107
<212> TYPE: PRT
<213> ORGANISM: human

<400> SEQUENCE: 20

Met Leu Pro Cys Leu Ala Leu Leu Leu Met Glu Leu Ser Val Cys
1               5                   10                  15

Thr Val Ala Gly Asp Gly Gly Glu Glu Gln Thr Leu Ser Thr Glu Ala
            20                  25                  30

Glu Thr Trp Glu Gly Ala Gly Pro Ser Ile Gln Leu Gln Leu Gln Glu
        35                  40                  45

Val Lys Thr Gly Lys Ala Ser Gln Phe Phe Gly Leu Met Gly Lys Arg
50                  55                  60

Val Gly Gly Arg Pro Leu Ile Gln Pro Arg Arg Lys Lys Ala Tyr Gln
65                  70                  75                  80

Leu Glu His Thr Phe Gln Gly Leu Leu Gly Lys Arg Ser Leu Phe Thr
            85                  90                  95

Glu Gly Arg Glu Asp Glu Ala Gln Gly Ser Glu
        100                 105     107

<210> SEQ ID NO 21
<211> LENGTH: 321
<212> TYPE: DNA
<213> ORGANISM: human

<400> SEQUENCE: 21
atgctgcctt gcctcgccct gcttctcctg atggagctgt ccgtgtgcac tgtggcaggt    60
gatggtggag aggaacagac actcagcact gaagcagaga cctgggaagg cgctggcccc   120
agcattcagc tccagctgca ggaggtgaag acgggcaagg caagccagtt ctttgggctg   180
atggggaagc gagtgggagg aagacctctg atccagccaa ggagaaaaaa agcatatcag   240
ctggaacaca cgttccaggg cctcctgggc aagagaagcc tgttcacaga aggcagagag   300
gatgaggccc aaggttcaga g                                              321

<210> SEQ ID NO 22
<211> LENGTH: 14
<212> TYPE: PRT
<213> ORGANISM: human

<400> SEQUENCE: 22

Lys Lys Ala Tyr Gln Leu Glu His Thr Phe Gln Gly Leu Leu
1               5                   10          14

<210> SEQ ID NO 23
<211> LENGTH: 13
<212> TYPE: PRT
<213> ORGANISM: Artificial Sequence
<220> FEATURE:
<223> OTHER INFORMATION: peptide

<400> SEQUENCE: 23

Lys Ala Tyr Gln Leu Glu His Thr Phe Gln Gly Leu Leu
1               5                   10      13

<210> SEQ ID NO 24
<211> LENGTH: 12
<212> TYPE: PRT
<213> ORGANISM: Artificial Sequence
<220> FEATURE:

<223> OTHER INFORMATION: peptide

<400> SEQUENCE: 24

Ala Tyr Gln Leu Glu His Thr Phe Gln Gly Leu Leu
 1               5                  10      12

<210> SEQ ID NO 25
<211> LENGTH: 11
<212> TYPE: PRT
<213> ORGANISM: Artificial Sequence
<220> FEATURE:
<223> OTHER INFORMATION: peptide

<400> SEQUENCE: 25

Tyr Gln Leu Glu His Thr Phe Gln Gly Leu Leu
 1               5                  10  11

<210> SEQ ID NO 26
<211> LENGTH: 10
<212> TYPE: PRT
<213> ORGANISM: Artificial Sequence
<220> FEATURE:
<223> OTHER INFORMATION: peptide

<400> SEQUENCE: 26

Gln Leu Glu His Thr Phe Gln Gly Leu Leu
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: Artificial Polypeptide
<220> FEATURE:
<221> NAME/KEY: PEPTIDE
<222> LOCATION: (01)..(01)
<223> OTHER INFORMATION: Xaa means pyroglutamic acid

<400> SEQUENCE: 27

Xaa Leu Glu His Thr Phe Gln Gly Leu Leu
 1               5                  10

<210> SEQ ID NO 28
<211> LENGTH: 15
<212> TYPE: PRT
<213> ORGANISM: Artificial Sequence
<220> FEATURE:
<223> OTHER INFORMATION: peptide

<400> SEQUENCE: 28

Arg Lys Lys Ala Tyr Gln Leu Glu His Thr Phe Gln Gly Leu Leu
 1               5                  10                  15

<210> SEQ ID NO 29
<211> LENGTH: 135
<212> TYPE: DNA
<213> ORGANISM: human

<400> SEQUENCE: 29
actgtggcag gtgatggtgg agaggaacag acactcagca ctgaagcaga gacctgggaa      60
ggcgctggcc ccagcattca gctccagctg caggaggtga agacgggcaa ggcaagccag     120
ttctttgggc tgatg                                                      135

<210> SEQ ID NO 30
<211> LENGTH: 33

```
<212> TYPE: DNA
<213> ORGANISM: human

<400> SEQUENCE: 30
acgggcaagg caagccagtt ctttgggctg atg                                    33

<210> SEQ ID NO 31
<211> LENGTH: 42
<212> TYPE: DNA
<213> ORGANISM: human

<400> SEQUENCE: 31
aaaaaagcat atcagctgga acacacgttc cagggcctcc tg                          42

<210> SEQ ID NO 32
<211> LENGTH: 5
<212> TYPE: PRT
<213> ORGANISM: Artificial Sequence
<220> FEATURE:
<223> OTHER INFORMATION: Artificial Polypeptide
<220> FEATURE:
<221> NAME/KEY: PEPTIDE
<222> LOCATION: (02)..(02)
<223> OTHER INFORMATION: Xaa is any amino acid

<400> SEQUENCE: 32

Phe Xaa Gly Leu Leu
 1               5

<210> SEQ ID NO 33
<211> LENGTH: 15
<212> TYPE: DNA
<213> ORGANISM: Artificial Sequence
<220> FEATURE:
<223> OTHER INFORMATION: primer/probe
<220> FEATURE:
<221> NAME/KEY: misc_feature
<222> LOCATION: (04)..(06)
<223> OTHER INFORMATION: NNN is any nucleic acid codon

<400> SEQUENCE: 33
ttcnnnggcc tcctg                                                        15

<210> SEQ ID NO 34
<211> LENGTH: 10
<212> TYPE: PRT
<213> ORGANISM: Artificial Sequence
<220> FEATURE:
<223> OTHER INFORMATION: peptide

<400> SEQUENCE: 34

Gly Lys Ala Ser Gln Phe Phe Gly Leu Met
 1               5                  10

<210> SEQ ID NO 35
<211> LENGTH: 9
<212> TYPE: PRT
<213> ORGANISM: Artificial Sequence
<220> FEATURE:
<223> OTHER INFORMATION: peptide

<400> SEQUENCE: 35

Lys Ala Ser Gln Phe Phe Gly Leu Met
 1               5               9

<210> SEQ ID NO 36
<211> LENGTH: 8
<212> TYPE: PRT
```

<213> ORGANISM: Artificial Sequence
<220> FEATURE:
<223> OTHER INFORMATION: peptide

<400> SEQUENCE: 36

Ala Ser Gln Phe Phe Gly Leu Met
1               5           8

<210> SEQ ID NO 37
<211> LENGTH: 7
<212> TYPE: PRT
<213> ORGANISM: Artificial Sequence
<220> FEATURE:
<223> OTHER INFORMATION: peptide

<400> SEQUENCE: 37

Ser Gln Phe Phe Gly Leu Met
1               5       7

<210> SEQ ID NO 38
<211> LENGTH: 6
<212> TYPE: PRT
<213> ORGANISM: Artificial Sequence
<220> FEATURE:
<223> OTHER INFORMATION: peptide

<400> SEQUENCE: 38

Gln Phe Phe Gly Leu Met
1               5   6

<210> SEQ ID NO 39
<211> LENGTH: 5
<212> TYPE: PRT
<213> ORGANISM: Artificial Sequence
<220> FEATURE:
<223> OTHER INFORMATION: peptide

<400> SEQUENCE: 39

Phe Gln Gly Leu Leu
1               5

<210> SEQ ID NO 40
<211> LENGTH: 39
<212> TYPE: DNA
<213> ORGANISM: Artificial Sequence
<220> FEATURE:
<223> OTHER INFORMATION: primer/probe

<400> SEQUENCE: 40
aaagcatatc agctggaaca cacgttccag ggcctcctg                    39

<210> SEQ ID NO 41
<211> LENGTH: 36
<212> TYPE: DNA
<213> ORGANISM: Artificial Sequence
<220> FEATURE:
<223> OTHER INFORMATION: primer/probe

<400> SEQUENCE: 41
gcatatcagc tggaacacac gttccagggc ctcctg                       36

<210> SEQ ID NO 42
<211> LENGTH: 33
<212> TYPE: DNA
<213> ORGANISM: Artificial Sequence
<220> FEATURE:
<223> OTHER INFORMATION: primer/probe

```
<400> SEQUENCE: 42
tatcagctgg aacacacgtt ccagggcctc ctg                          33

<210> SEQ ID NO 43
<211> LENGTH: 30
<212> TYPE: DNA
<213> ORGANISM: Artificial Sequence
<220> FEATURE:
<223> OTHER INFORMATION: primer/probe

<400> SEQUENCE: 43
cagctggaac acacgttcca gggcctcctg                              30

<210> SEQ ID NO 44
<211> LENGTH: 30
<212> TYPE: DNA
<213> ORGANISM: Artificial Sequence
<220> FEATURE:
<223> OTHER INFORMATION: primer/probe
<220> FEATURE:
<221> NAME/KEY: misc_feature
<222> LOCATION: (01)..(03)
<223> OTHER INFORMATION: NNN is any nucleic acid codon

<400> SEQUENCE: 44
nnnctggaac acacgttcca gggcctcctg                              30

<210> SEQ ID NO 45
<211> LENGTH: 45
<212> TYPE: DNA
<213> ORGANISM: Artificial Sequence
<220> FEATURE:
<223> OTHER INFORMATION: primer/probe

<400> SEQUENCE: 45
agaaaaaaag catatcagct ggaacacacg ttccagggcc tcctg             45

<210> SEQ ID NO 46
<211> LENGTH: 30
<212> TYPE: DNA
<213> ORGANISM: Artificial Sequence
<220> FEATURE:
<223> OTHER INFORMATION: primer/probe

<400> SEQUENCE: 46
ggcaaggcaa gccagttctt tgggctgatg                              30

<210> SEQ ID NO 47
<211> LENGTH: 27
<212> TYPE: DNA
<213> ORGANISM: Artificial Sequence
<220> FEATURE:
<223> OTHER INFORMATION: primer/probe

<400> SEQUENCE: 47
aaggcaagcc agttctttgg gctgatg                                 27

<210> SEQ ID NO 48
<211> LENGTH: 24
<212> TYPE: DNA
<213> ORGANISM: Artificial Sequence
<220> FEATURE:
<223> OTHER INFORMATION: primer/probe

<400> SEQUENCE: 48
gcaagccagt tctttgggct gatg                                    24
```

<210> SEQ ID NO 49
<211> LENGTH: 21
<212> TYPE: DNA
<213> ORGANISM: Artificial Sequence
<220> FEATURE:
<223> OTHER INFORMATION: primer/probe

<400> SEQUENCE: 49
agccagttct ttgggctgat g                                      21

<210> SEQ ID NO 50
<211> LENGTH: 18
<212> TYPE: DNA
<213> ORGANISM: Artificial Sequence
<220> FEATURE:
<223> OTHER INFORMATION: primer/probe

<400> SEQUENCE: 50
cagttctttg ggctgatg                                          18

<210> SEQ ID NO 51
<211> LENGTH: 15
<212> TYPE: DNA
<213> ORGANISM: Artificial Sequence
<220> FEATURE:
<223> OTHER INFORMATION: primer/probe

<400> SEQUENCE: 51
ttccagggcc tcctg                                             15

<210> SEQ ID NO 52
<211> LENGTH: 160
<212> TYPE: DNA
<213> ORGANISM: Human

<400> SEQUENCE: 52
attcagctcc agctgcagga ggtgaagacg ggcaaggcaa gccagttctt tgggctgatg      60
gggaagcgag tgggaggtga gtgacaatga caatggagcc cagcaagcag gggttctgag     120
tgggttctgc aacataaagc agaggcccta agtcaaagcc                          160

<210> SEQ ID NO 53
<211> LENGTH: 40
<212> TYPE: DNA
<213> ORGANISM: Artificial Sequence
<220> FEATURE:
<223> OTHER INFORMATION: Designed oligonucleotide primer to amplify ATT
      beta cDNA fragment

<400> SEQUENCE: 53
cgaattccca ccatgctgcc ttgcctcgcc ctgcttctcc                           40

<210> SEQ ID NO 54
<211> LENGTH: 44
<212> TYPE: DNA
<213> ORGANISM: Artificial Sequence
<220> FEATURE:
<223> OTHER INFORMATION: Designed oligonucleotide primer to amplify ATT
      beta cDNA fragment

<400> SEQUENCE: 54
gtacagtcga cttattactc tgaaccttgg gcctcatcct ctct                      44

<210> SEQ ID NO 55
<211> LENGTH: 250
<212> TYPE: DNA

<213> ORGANISM: Human

<400> SEQUENCE: 55

```
gaattccacc atgctgcctt gcctcgccct gcttctcctg atggagctgt ccgtgtgcac      60
tgtggcaggt gatggtggag aggaacagac actcagcact gaagcagaga cctgggaagg    120
cgctggcccc agcattcagc tccagctgca ggaggtgaag acgggcaagg caagccagtt    180
ctttgggctg atggggaagc gagtgggagg cagagaggat gaggcccaag gttcagagta    240
ataagtcgac                                                           250
```

<210> SEQ ID NO 56
<211> LENGTH: 39
<212> TYPE: DNA
<213> ORGANISM: Artificial Sequence
<220> FEATURE:
<223> OTHER INFORMATION: Designed oligonucleotide primer to amplify ATT
    #21 cDNA fragment

<400> SEQUENCE: 56

```
cagtggaatt ccaccatgct gccttgcctc gccctgctt                            39
```

<210> SEQ ID NO 57
<211> LENGTH: 38
<212> TYPE: DNA
<213> ORGANISM: Artificial Sequence
<220> FEATURE:
<223> OTHER INFORMATION: Designed oligonucleotide primer to amplify ATT
    #21 cDNA fragment

<400> SEQUENCE: 57

```
ggtgggtcga cttactctga accttgggcc tcatcctc                             38
```

<210> SEQ ID NO 58
<211> LENGTH: 340
<212> TYPE: DNA
<213> ORGANISM: Human

<400> SEQUENCE: 58

```
gaattccacc atgctgcctt gcctcgccct gcttctcctg atggagctgt ccgtgtgcac      60
tgtggcaggt gatggtggag aggaacagac actcagcact gaagcagaga cctgggaagg    120
cgctggcccc agcattcagc tccagctgca ggaggtgaag acgggcaagg caagccagtt    180
ctttgggctg atggggaagc gagtgggagg aagacctctg atccagccaa ggagaaaaaa    240
agcatatcag ctggaacaca cgttccaggg cctcctgggc aagagaagcc tgttcacaga    300
aggcagagag gatgaggccc aaggttcaga gtaagtcgac                          340
```

<210> SEQ ID NO 59
<211> LENGTH: 24
<212> TYPE: DNA
<213> ORGANISM: Artificial Sequence
<220> FEATURE:
<223> OTHER INFORMATION: Designed oligonucleotide primer to amplify
    PPT-A cDNA fragment

<400> SEQUENCE: 59

```
ggactgtccg tcgcaaaatc caac                                            24
```

<210> SEQ ID NO 60
<211> LENGTH: 24
<212> TYPE: DNA
<213> ORGANISM: Artificial Sequence
<220> FEATURE:
<223> OTHER INFORMATION: Designed oligonucleotide primer to amplify PPT-A cDNA fragment

<400> SEQUENCE: 60
ttctttaggg actgtatcat tgac         24

<210> SEQ ID NO 61
<211> LENGTH: 43
<212> TYPE: DNA
<213> ORGANISM: Artificial Sequence
<220> FEATURE:
<223> OTHER INFORMATION: Designed oligonucleotide primer to amplify
    PPT-A cDNA fragment

<400> SEQUENCE: 61
gtccgaattc caccatgaaa atcctcgtgg ccttggcagt ctt         43

<210> SEQ ID NO 62
<211> LENGTH: 38
<212> TYPE: DNA
<213> ORGANISM: Artificial Sequence
<220> FEATURE:
<223> OTHER INFORMATION: Designed oligonucleotide primer to amplify
    PPT-A cDNA fragment

<400> SEQUENCE: 62
tgttagtcga cttattaacg tcttctttca taattctg         38

<210> SEQ ID NO 63
<211> LENGTH: 129
<212> TYPE: PRT
<213> ORGANISM: Human

<400> SEQUENCE: 63

Met Lys Ile Leu Val Ala Leu Ala Val Phe Phe Leu Val Ser Thr Gln
1               5                   10                  15

Leu Phe Ala Glu Glu Ile Gly Ala Asn Asp Asp Leu Asn Tyr Trp Ser
            20                  25                  30

Asp Trp Tyr Asp Ser Asp Gln Ile Lys Glu Glu Leu Pro Glu Pro Phe
        35                  40                  45

Glu His Leu Leu Gln Arg Ile Ala Arg Arg Pro Lys Pro Gln Gln Phe
    50                  55                  60

Phe Gly Leu Met Gly Lys Arg Asp Ala Asp Ser Ser Ile Glu Lys Gln
65                  70                  75                  80

Val Ala Leu Leu Lys Ala Leu Tyr Gly His Gly Gln Ile Ser His Lys
                85                  90                  95

Arg His Lys Thr Asp Ser Phe Val Gly Leu Met Gly Lys Arg Ala Leu
            100                 105                 110

Asn Ser Val Ala Tyr Glu Arg Ser Ala Met Gln Asn Tyr Glu Arg Arg
        115                 120                 125

Arg
129

<210> SEQ ID NO 64
<211> LENGTH: 409
<212> TYPE: DNA
<213> ORGANISM: Human

<400> SEQUENCE: 64
gaattccacc atgaaaatcc tcgtggcctt ggcagtcttt tttcttgtct ccactcagct   60
gtttgcagaa gaaataggag ccaatgatga tctgaattac tggtccgact ggtacgacag  120
cgaccagatc aaggaggaac tgccggagcc ctttgagcat cttctgcaga gaatcgcccg  180

```
gagacccaag cctcagcagt tctttggatt aatgggcaaa cgggatgctg attcctcaat    240
tgaaaaacaa gtggccctgt taaaggctct ttatggacat ggccagatct ctcacaaaag    300
acataaaaca gattcctttg ttggactaat gggcaaaaga gctttaaatt ctgtggctta    360
tgaaaggagt gcaatgcaga attatgaaag aagacgttaa taagtcgac                409
```